US012680101B2

(12) United States Patent
Ui-Tei et al.

(10) Patent No.: US 12,680,101 B2
(45) Date of Patent: Jul. 14, 2026

(54) RNA MOLECULE, CHIMERIC NA MOLECULE, DOUBLE-STRANDED RNA MOLECULE, AND DOUBLE-STRANDED CHIMERIC NA MOLECULE

(71) Applicant: The University of Tokyo, Tokyo (JP)

(72) Inventors: Kumiko Ui-Tei, Tokyo (JP); Yoshiaki Kobayashi, Tokyo (JP); Kaoru Saigo, Tokyo (JP); Yukikazu Natori, Kanagawa (JP); Atsushi Sato, Tokyo (JP); Yoshimasa Asano, Tokyo (JP)

(73) Assignee: The University of Tokyo, Tokyo (JP)

( * ) Notice: Subject to any disclaimer, the term of this patent is extended or adjusted under 35 U.S.C. 154(b) by 1172 days.

(21) Appl. No.: 17/626,867

(22) PCT Filed: Jul. 16, 2020

(86) PCT No.: PCT/JP2020/027738
§ 371 (c)(1),
(2) Date: Jul. 11, 2022

(87) PCT Pub. No.: WO2021/010449
PCT Pub. Date: Jan. 21, 2021

(65) Prior Publication Data
US 2022/0411800 A1      Dec. 29, 2022

(30) Foreign Application Priority Data

Jul. 16, 2019    (JP) ................................. 2019-130966

(51) Int. Cl.
*C12N 15/113*          (2010.01)
(52) U.S. Cl.
CPC ...... *C12N 15/1135* (2013.01); *C12N 2310/14* (2013.01); *C12N 2310/321* (2013.01); *C12N 2310/322* (2013.01); *C12N 2310/3231* (2013.01)

(58) Field of Classification Search
None
See application file for complete search history.

(56) References Cited

U.S. PATENT DOCUMENTS

| | | | |
|---|---|---|---|
| 2010/0222414 A1 | 9/2010 | Puri et al. | |
| 2012/0136039 A1* | 5/2012 | Aronin ................. | A61K 31/713 |
| | | | 536/24.5 |
| 2016/0304878 A1 | 10/2016 | Chi et al. | |
| 2023/0295624 A1* | 9/2023 | Ui-Tei ................... | C12N 15/10 |
| | | | 514/44 A |
| 2024/0141337 A1* | 5/2024 | Ui-Tei ................... | C12N 15/113 |

FOREIGN PATENT DOCUMENTS

| | | |
|---|---|---|
| EP | 2 583 692 A1 | 4/2013 |
| JP | 2010-538677 A | 12/2010 |
| JP | 2017-502665 A | 1/2017 |
| JP | 2019-88196 A | 6/2019 |
| WO | 2018/098328 A1 | 5/2018 |

OTHER PUBLICATIONS

Huang et al. Nucleic Acid Research, vol. 37, pp. 7560-7569 (Year: 2009).*
Muller et al. FASEB J 26:6689-677 (Year: 2012).*
Manoharan, et al., "Unique Gene-Silencing and Structural Properties of 2'-Fluor••Modified siRNAs", Angew. Chem. Int. Ed., 2011, vol. 50, No. 10, pp. 2284-2288, 2011 (5 pages).
Rao, et al., "KRAS mutant allele-specific expression knockdown in pancreatic cancer model with systemically delivered bi-shRNA KRAS lipoplex", Plos One, vol. 13, No. 5, p. 0193644, May 31, 2018 (20 pages).
Geng, et al., "Double-mismatched siRNAs enhance selective gene silencing of a mutant ALS-causing allele" Acta Pharmacol. Sin., vol. 29, No. 2, pp. 211-216, Feb. 2008 (6 pages).
Ohnishi, et al., "Enhancement of Allele Discrimination by Introduction of Nucleotide Mismatches into siRNA in Allele-Specific Gene Silencing by RNAi", Plos One, vol. 3, No. 5, pp. E2248-1, May 21, 2008 (9 pages).
Sholefield, et al., "Design of RNAi Hairpins for Mutation-Specific Silencing of Ataxin-7 and Correction of a SCA7 Phenotype", Pios One, vol. 4, No. 9, e7232, Sep. 30, 2009 (11 pages).
Feng, et al., "Allele-specific silencing of Alzheimer's disease genes The amyloid precursor protein genes with Swedish or London mutations", Gene, vol. 371, No. 1, pp. 68-74, Apr. 12, 2006 (7 pages).
Takahashi, et al., "Disease-causing allele-specific silencing against the ALK2 mutants, R206H and G356D, in fibrodysplasia ossificans progressiva", Gene Therapy, vol. 19, No. 7, pp. 781-785, 2012 (5 pages).
Pfister, et al., "Five siRNAs Targeting Three SNPs May Provide Therapy for Three-Quarters of Huntington's Disease Patients", Current Biology, vol. 19, No. 9, pp. 774-778, May 12, 2009 (5 pages).

(Continued)

*Primary Examiner* — Brian Whiteman
(74) *Attorney, Agent, or Firm* — Rothwell, Figg, Ernst & Manbeck, P.C.

(57) ABSTRACT

The present invention is directed to provide novel RNA molecules, chimeric NA molecules, double-stranded RNA molecules, and double-stranded chimeric NA molecules. Specifically, an embodiment of the present invention is an RNA molecule for RNA interference to target a mutant allele with a point mutation, in which (1) the molecule has a nucleotide sequence complementary to a nucleotide sequence of a coding region of the mutant allele; and (2) when counted from the base at the 5'-end in a nucleotide sequence complementary to a nucleotide sequence of the mutant allele, (2-1) a base at position 5 or 6 is mismatched to a base in the mutant allele; (2-2) a position 10 or 11 corresponds to the position of the point mutation; and (2-3) a group at the 2'-position of a pentose at positions 6-8 or positions 7 and 8 is modified with, e.g., $OCH_3$. In this RNA molecule, one or more ribonucleotides may be replaced by, e.g., a deoxyribonucleotide. The molecule may form a double-stranded RNA with a complementary strand.

13 Claims, 20 Drawing Sheets

Specification includes a Sequence Listing.

(56)                    References Cited

OTHER PUBLICATIONS

Extended European Search Report in EP20840283.4 dated Nov. 27, 2023 (15 pages).

Iribe et al., "Chemical Modification of the siRNA Seed Region Suppresses Off-Target Effects by Steric Hindrance to Base-Pairing with Targets", ACS Omega, vol. 2, No. 5, 2017, pp. 2055-2064, XP055788985 (15 pages).

Jackson et al., "Expression profiling reveals off-target gene regulation by RNAi," Nat Biotechnol. 21(6):635-7 (2003).

Ui-Tei et al., "Thermodynamic stability and Watson-Crick base pairing in the seed duplex are major determinants of the efficiency of the siRNA-based off-target effect," Nucleic Acid Res. 36(22):7100-9 (2008).

Inoue, H. et al., "Synthesis and hybridization studies on two complementary nona(2'-O-methyl)ribonucleotides", Nucleic Acids Research, 1987, vol. 15, No. 15, pp. 6131-6148.

Vester, B., and Wengel, J., "LNA (Locked Nucleic Acid): High-Affinity Targeting of Complementary RNA and DNA", Biochemistry, Oct. 26, 2004, vol. 43, No. 42, pp. 13233-13241.

An, S., et al., "An siRMSD parameter of structural distortion induced by chemical mpdification is predictive of the off-target effect of siRNA", Molecular Therapy: Nucleic Acids, 2025, Issue 102693.

Nicolau, C., et al., "Halogenation of nucleic acid structures: from chemical biology to supramolecular chemistry", RSC Chemical Biology, 2025, vol. 6, pp. 1007-1018.

* cited by examiner

AsPC-1 (KRAS mut: G12A)

······ siCont (n=6)
—— siKRAS-WT (n=5)
—— siKRAS-A (n=5)

Tumor volume (mm³)

Time after implantation (day)

(siRNA treatment: Day 11, 18 and 25; *p < 0.05 by Student's
t test *versus* siKRAS-WT; all data are presented as mean ± SEM)

RNA MOLECULE, CHIMERIC NA MOLECULE, DOUBLE-STRANDED RNA MOLECULE, AND DOUBLE-STRANDED CHIMERIC NA MOLECULE

CROSS-REFERENCE TO RELATED APPLICATIONS

The present application claims priority to Japanese patent application No. 2019-130966, filed on Jul. 16, 2019, which is hereby incorporated by reference.

SEQUENCE LISTING

The instant application contains a Sequence Listing which has been submitted electronically in ASCII format and is hereby incorporated by reference in its entirety. Said ASCII copy, created on Jul. 8, 2022 is named 51650-002001 Sequence Listing 7 8 22 ST25 and is 28,238 bytes in size.

TECHNICAL FIELD

The present invention relates to RNA molecules, chimeric NA molecules, double-stranded RNA molecules, and double-stranded chimeric NA molecules, for use in RNA interference.

RELATED ART

RNA interference is a simple and efficient way to specifically suppress the expression of given target genes in cells.

It is, however, becoming understood to suppress the expression of unintended targets (off-targeted genes) more than expected at the beginning (Jackson, A. L. et al., (2003) Nature Biotechnology vol. 21, pp. 635-637). Particularly, it has been revealed that the stronger the affinity of siRNA to mRNA of the target gene, the greater off-target effects are induced (Ui-Tei, K. et al. (2008) Nucleic Acids Res. vol. 36, pp. 7100-7109).

SUMMARY OF THE INVENTION

Problem to be Solved by the Invention

An object of the present invention is to provide novel RNA molecules, novel chimeric NA molecules, novel double-stranded RNA molecules, and novel double-stranded chimeric NA molecules.

Means to Solve the Problem

During the intensive efforts directed toward the identification of RNA sequences with reduced off-target effects, the present inventors found that contribution of a mismatch of nucleotide at position 10 or 11 in RNA molecules to off-target effects is reduced when the molecules have a mismatch at position 5 or 6 and are modified at the 2'-position of a pentose in each of their ribonucleotides at positions 6-8 or positions 7 and 8. Thus, in RNA interference in which the target gene is a mutant allele having a point mutation compared to its wild-type allele of a gene, the present inventors succeeded in mainly suppressing the expression of the mutant allele but not substantially suppressing the expression of the wild-type allele, by designing an RNA molecule whose base at position 10 or 11 corresponds to the position of the point mutation and is identical to the one in the mutant allele, by using a double-stranded RNA molecule with the aforementioned RNA molecule as a guide strand for RNA interference. The present invention was thus completed.

[1] Genes in General

[1-1] An aspect of the present invention is an RNA molecule for use in RNA interference to target a mutant allele of a gene, the mutant allele having a point mutation relative to a wild-type allele of the gene, the RNA molecule satisfying the following conditions:

(1) the molecule has a nucleotide sequence complementary to a nucleotide sequence of a coding region of the mutant allele except for a base specified in (2-1) below; and (2) when counted from the base at the 5'-end in a nucleotide sequence complementary to the nucleotide sequence of the mutant allele, (2-1) a base at position 5 or 6 is mismatched to a base in the mutant allele;

(2-2) a position 10 or 11 corresponds to the position of the point mutation, and the base at position 10 or 11 is complementary to the base at the position of the point mutation in the mutant allele; and (2-3) a group at the 2'-position of a pentose in each of ribonucleotides at positions 6-8 or positions 7 and 8 is modified with $OCH_3$, halogen, or LNA. The halogen may be fluorine. When a base at the 5'-end of the nucleotide sequence specified in (1) above is not adenine or uracil, it may be replaced by adenine or uracil. When a base at the 3'-end of the nucleotide sequence specified in (1) above is not cytosine or guanine, it may be replaced by cytosine or guanine. Any of the aforementioned RNA molecules may contain 13-28 nucleotides. Any of the aforementioned RNA molecules may be a chimeric NA molecule wherein one or more ribonucleotides are replaced by a deoxyribonucleotide, an artificial nucleic acid, or a nucleic acid analog.

[1-2] A further aspect of the present invention is a double-stranded RNA molecule including a guide strand and a passenger strand, the guide strand being any one of the aforementioned RNA molecules, and the passenger strand being an RNA molecule with a sequence complementary to that of the RNA molecule of the guide strand. An overhang may be present at the 3'-end of the guide strand and/or at the 3'-end of the passenger strand. The overhang(s) may be 1-3 nucleotide(s) long. Any of the aforementioned double-stranded RNA molecules may be a double-stranded chimeric NA molecule in which one or more ribonucleotides are replaced by a deoxyribonucleotide, an artificial nucleic acid, or a nucleic acid analog.

[1-3] A further aspect of the present invention is a method for producing an RNA molecule for use as a guide strand in RNA interference, including the step of producing any one of the aforementioned RNA molecules. The RNA molecule may be a chimeric NA molecule wherein one or more ribonucleotides are replaced by a deoxyribonucleotide, an artificial nucleic acid, or a nucleic acid analog.

[1-4] A further aspect of the present invention is a method for performing RNA interference in a cell containing a wild-type allele of a gene and the mutant allele of the gene to target the mutant allele, the mutant allele having a point mutation, wherein the method includes the step of introducing any one of the aforementioned RNA molecules, chimeric NA molecules, double-stranded RNA molecules, or any one of the aforementioned double-stranded chimeric NA molecules into the cell.

[1-5] A further aspect of the present invention is a therapeutic agent for a patient with a tumor including a tumor cell having a wild-type allele of an oncogene and a mutant allele of the oncogene, the mutant allele having a point mutation, the point mutation being responsible for malignant transformation, wherein the therapeutic agent includes, as an active ingredient, any one of the aforementioned RNA molecules, chimeric NA molecules, double-stranded RNA molecules, or any one of the aforementioned double-stranded chimeric NA molecules.

[1-6] A further aspect of the present invention is a selection method for selecting an RNA molecule, a chimeric NA molecule, a double-stranded RNA molecule, or a double-stranded chimeric NA molecule for use in RNA interference to silence a target gene, the selection method including the steps of, by performing the aforementioned RNAi-based method in vitro using each of a plurality of any one of the aforementioned RNA molecules, chimeric NA molecules, double-stranded RNA molecules, or any one of the aforementioned double-stranded chimeric NA molecules, evaluating gene-specific silencing abilities of the plurality of the RNA molecules, the chimeric NA molecules, the double-stranded RNA molecules, or the double-stranded chimeric NA molecules, to the target gene; and selecting an RNA molecule, a chimeric NA molecule, a double-stranded RNA molecule, or a double-stranded chimeric NA molecule having a gene-specific silencing ability of equal to or higher than a predetermined level.

[2] K-Ras Genes

[2-1] According to a further aspect of the present invention, in any one of the RNA molecules described in [1-1], the gene is a K-ms gene, the wild-type allele is a K-ms (wt) allele, and the mutant allele is a K-ms (c. 35G>A) allele, a K-ms (c. 35G>T) allele, or a K-ms (c. 35G>C) allele. A nucleotide sequence complementary to that of the coding region of the mutant allele, containing the base specified in (2-1) above, may have any one of:

```
                                         (SEQ ID NO. 1)
    5'-UCCUACGCCAUCAGCUCCA-3', (SEQ ID NO. 2)
    5'-UCCUACGCCAACAGCUCCA-3',
    and (SEQ ID NO. 3)
    5'-UCCUACGCCAGCAGCUCCA-3'.
```

One or more ribonucleotides in the aforementioned RNA molecule(s) may be replaced by a deoxyribonucleotide, an artificial nucleic acid, or a nucleic acid analog.

[2-2] According to a further aspect of the present invention, in any one of the double-stranded RNA molecules described in [1-2], the gene is a K-ms gene, the wild-type allele is a K-ms (wt) allele, and the mutant allele is a K-ms (c. 35G>A) allele, a K-ras (c. 35G>T) allele, or a K-ms (c. 35G>C) allele. In the aforementioned guide strand(s), a nucleotide sequence complementary to that of the coding region of the mutant allele, containing the base specified in (2-1) above, may have any one of:

```
                                         (SEQ ID NO. 1)
    5'-UCCUACGCCAUCAGCUCCA-3', (SEQ ID NO. 2)
    5'-UCCUACGCCAACAGCUCCA-3',
    and (SEQ ID NO. 3)
    5'-UCCUACGCCAGCAGCUCCA-3'.
```

One or more ribonucleotides in the aforementioned double-stranded RNA molecule(s) may be replaced by a deoxyribonucleotide, an artificial nucleic acid, or a nucleic acid analog.

[2-3] According to a further aspect of the present invention, in any one of the production methods described in [1-3], the gene is a K-ms gene, the wild-type allele is a K-ms (wt) allele, and the mutant allele is a K-ms (c. 35G>A) allele, a K-ms (c. 35G>T) allele, or a K-ms (c. 35G>C) allele. A nucleotide sequence complementary to that of the coding region of the mutant allele, containing the base specified in (2-1) above, may have any one of:

```
                                         (SEQ ID NO. 1)
    5'-UCCUACGCCAUCAGCUCCA-3', (SEQ ID NO. 2)
    5'-UCCUACGCCAACAGCUCCA-3',
    and (SEQ ID NO. 3)
    5'-UCCUACGCCAGCAGCUCCA-3'.
```

One or more ribonucleotides in the aforementioned RNA molecule(s) may be replaced by a deoxyribonucleotide, an artificial nucleic acid, or a nucleic acid analog.

[2-4] According to a further aspect of the present invention, in any one of the methods for performing RNA interference described in [1-4], the gene is a K-ms gene, the wild-type allele is a K-ms (wt) allele, and the mutant allele is a K-ms (c. 35G>A) allele, a K-ms (c. 35G>T) allele, or a K-ms (c. 35G>C) allele. In the aforementioned guide strand(s), a nucleotide sequence complementary to that of the coding region of the mutant allele, containing the base specified in (2-1) above, may have any one of:

```
                                         (SEQ ID NO. 1)
    5'-UCCUACGCCAUCAGCUCCA-3', (SEQ ID NO. 2)
    5'-UCCUACGCCAACAGCUCCA-3',
    and (SEQ ID NO. 3)
    5'-UCCUACGCCAGCAGCUCCA-3'.
```

One or more ribonucleotides in the aforementioned double-stranded RNA molecule(s) may be replaced by a deoxyribonucleotide, an artificial nucleic acid, or a nucleic acid analog.

[2-5] According to a further aspect of the present invention, in any one of the therapeutic agents described in [1-5], the oncogene is a K-ms gene, the wild-type allele is a K-ms (wt) allele, and the mutant allele is a K-ms (c. 35G>A) allele, a K-ms (c. 35G>T) allele, or a K-ms (c. 35G>C) allele. In the aforementioned guide strand(s), a nucleotide sequence complementary to that of the coding region of the mutant allele, containing the base specified in (2-1) above, may have any one of:

```
                                         (SEQ ID NO. 1)
    5'-UCCUACGCCAUCAGCUCCA-3', (SEQ ID NO. 2)
    5'-UCCUACGCCAACAGCUCCA-3',
    and (SEQ ID NO. 3)
    5'-UCCUACGCCAGCAGCUCCA-3'.
```

5

One or more ribonucleotides in the aforementioned double-stranded RNA molecule(s) may be replaced by a deoxyribonucleotide, an artificial nucleic acid, or a nucleic acid analog.

[2-6] According to a further aspect of the present invention, in any one of the selection methods described in [1-6], the gene is a K-ms gene, the wild-type allele is a K-ms (wt) allele, and the mutant allele is a K-ms (c. 35G>A) allele, a K-ms (c. 35G>T) allele, or a K-ms (c. 35G>C) allele.

[3] N-Ras Genes

[3-1] According to a further aspect of the present invention, in any one of the RNA molecules described in [1-1], the gene is an N-ms gene, the wild-type allele is an N-ms (wt) allele, and the mutant allele is an N-ms (c. 35G>A) allele or an N-ms (c. 182A>G) allele. A nucleotide sequence complementary to that of the coding region of the mutant allele, containing the base specified in (2-1) above, may have any one of:

```
                                    (SEQ ID NO. 146)
5'-CCCAACACCACCUGCUCCA-3'
and (SEQ ID NO. 147)
5'-GUACUCUUCUUGUCCAGCU-3'.
```

One or more ribonucleotides in the aforementioned RNA molecule(s) may be replaced by a deoxyribonucleotide, an artificial nucleic acid, or a nucleic acid analog.

[3-2] According to a further aspect of the present invention, in any one of the double-stranded RNA molecules described in [1-2], the gene is an N-ms gene, the wild-type allele is an N-ms (wt) allele, and the mutant allele is an N-ms (c. 35G>A) allele or an N-ms (c. 182A>G) allele. In the aforementioned guide strand(s), a nucleotide sequence complementary to that of the coding region of the mutant allele, containing the base specified in (2-1) above, may have any one of:

```
                                    (SEQ ID NO. 146)
5'-CCCAACACCACCUGCUCCA-3'
and (SEQ ID NO. 147)
5'-GUACUCUUCUUGUCCAGCU-3'.
```

One or more ribonucleotides in the aforementioned double-stranded RNA molecule(s) may be replaced by a deoxyribonucleotide, an artificial nucleic acid, or a nucleic acid analog.

[3-3] According to a further aspect of the present invention, in any one of the production methods described in [1-3], the gene is an N-ms gene, the wild-type allele is an N-ms (wt) allele, and the mutant allele is an N-ms (c. 35G>A) allele or an N-ras (c. 182A>G) allele. A nucleotide sequence complementary to that of the coding region of the mutant allele, containing the base specified in (2-1) above, may have any one of:

```
                                    (SEQ ID NO. 146)
5'-CCCAACACCACCUGCUCCA-3'
and (SEQ ID NO. 147)
5'-GUACUCUUCUUGUCCAGCU-3'.
```

One or more ribonucleotides in the aforementioned RNA molecule(s) may be replaced by a deoxyribonucleotide, an artificial nucleic acid, or a nucleic acid analog. [3-4] According to a further aspect of the present invention, in any one of the methods for performing RNA interference described in [1-4], the gene is an N-ras gene, the wild-type allele is an N-ras (wt) allele, and the mutant allele is an N-ras (c. 35G>A) allele or an N-ms (c. 182A>G) allele. In the aforementioned guide strand(s), a nucleotide sequence complementary to that of the coding region of the mutant allele, containing the base specified in (2-1) above, may have any one of:

```
                                    (SEQ ID NO. 146)
5'-CCCAACACCACCUGCUCCA-3'
and (SEQ ID NO. 147)
5'-GUACUCUUCUUGUCCAGCU-3'.
```

One or more ribonucleotides in the aforementioned double-stranded RNA molecule(s) may be replaced by a deoxyribonucleotide, an artificial nucleic acid, or a nucleic acid analog.

[3-5] According to a further aspect of the present invention, in any one of the therapeutic agents described in [1-5], the oncogene is an N-ms gene, the wild-type allele is an N-ms (wt) allele, and the mutant allele is an N-ms (c. 35G>A) allele or an N-ms (c. 182A>G) allele. In the aforementioned guide strand(s), a nucleotide sequence complementary to that of the coding region of the mutant allele, containing the base specified in (2-1) above, may have any one of:

```
                                    (SEQ ID NO. 146)
5'-CCCAACACCACCUGCUCCA-3'
and (SEQ ID NO. 147)
5'-GUACUCUUCUUGUCCAGCU-3'.
```

One or more ribonucleotides in the aforementioned double-stranded RNA molecule(s) may be replaced by a deoxyribonucleotide, an artificial nucleic acid, or a nucleic acid analog.

[3-6] According to a further aspect of the present invention, in any one of the selection methods described in [1-6], the gene is an N-ms gene, the wild-type allele is an N-ms (wt) allele, and the mutant allele is an N-ms (c. 35G>A) allele or an N-ms (c. 182A>G) allele.

[4] Other Genes

[4-1] According to a further aspect of the present invention, in any one of the RNA molecules described in [1-1], the gene is a BRCA2 gene, the wild-type allele is BRCA2 (wt), and the mutant allele is an A1114C mutant allele; or in any one of the aforementioned RNA molecules, the gene is an STK11 gene, the wild-type allele is STK11 (wt) and the mutant allele is a C1062G mutant allele; or in any one of the aforementioned RNA molecules, the gene is a PTEN gene, the wild-type allele is PTEN (wt), and the mutant allele is a C388G mutant allele; or in any one of the aforementioned RNA molecules, the gene is an APC gene, the wild-type allele is APC (wt), and the mutant allele is a C4348T mutant allele; or in any one of the aforementioned RNA molecules, the gene is a GATA2 gene, the wild-type allele is GATA2 (wt), and the mutant allele is a C953T mutant allele; or in any one of the aforementioned RNA molecules, the gene is an MYD88 gene, the wild-type allele MYD88 (wt), and the mutant allele is a T818C mutant allele; or in any one of the aforementioned RNA molecules, the gene is a GNAQ gene, the wild-type allele is GNAQ (wt), and the mutant allele is an A626T mutant allele; or in any one of the aforementioned RNA molecules, the gene is an IDH1 gene, the wild-type allele is IDH1 (wt), and the mutant allele is a G395A mutant allele.

In the aforementioned guide strand(s), a nucleotide sequence complementary to that of the coding region of the mutant allele, containing the base specified in (2-1) above in the guide strand, may have any one of:

```
                                      (SEQ ID NO. 148)
        5'-GGCUUCUGAUUUGCUACAU-3'

(SEQ ID NO. 149)
        5'-CCUCGAUGUCGAAGAGGUC-3'

(SEQ ID NO. 150)
        5'-ACACCAGUUCGUCCCUUUC-3'

(SEQ ID NO. 151)
        5'-GGUACUUCUCGCUUGGUUU-3'

(SEQ ID NO. 152)
        5'-GAGGCCACAGGCAUUGCAC-3'

(SEQ ID NO. 153)
        5'-GAUGGGGAUCAGUCGCUUC-3'

(SEQ ID NO. 154)
        5'-CUCUGACCUUUGGCCCCCU-3'
        and (SEQ ID NO. 155)
        5'-AUAAGCAUGACGACCUAUG-3'.
```

In addition, one or more ribonucleotides in the aforementioned double-stranded RNA molecule(s) may be replaced by a deoxyribonucleotide, an artificial nucleic acid, or a nucleic acid analog.

[4-2] According to a further aspect of the present invention, in any one of the double-stranded RNA molecules described in [1-2], the gene is a BRCA2 gene, the wild-type allele is BRCA2 (wt), and the mutant allele is an A1114C mutant allele; or in any one of the aforementioned RNA molecules, the gene is an STK11 gene, the wild-type allele is STK11 (wt) and the mutant allele is a C1062G mutant allele; or in any one of the aforementioned RNA molecules, the gene is a PTEN gene, the wild-type allele is PTEN (wt), and the mutant allele is a C388G mutant allele; or in any one of the aforementioned RNA molecules, the gene is an APC gene, the wild-type allele is APC (wt), and the mutant allele is a C4348T mutant allele; or in any one of the aforementioned RNA molecules, the gene is a GATA2 gene, the wild-type allele is GATA2 (wt), and the mutant allele is a C953T mutant allele; or in any one of the aforementioned RNA molecules, the gene is an MYD88 gene, the wild-type allele MYD88 (wt), and the mutant allele is a T818C mutant allele; or in any one of the aforementioned RNA molecules, the gene is a GNAQ gene, the wild-type allele is GNAQ (wt), and the mutant allele is an A626T mutant allele; or in any one of the aforementioned RNA molecules, the gene is an IDH1 gene, the wild-type allele is IDH1 (wt), and the mutant allele is a G395A mutant allele.

In the aforementioned guide strand(s), a nucleotide sequence complementary to that of the coding region of the mutant allele, containing the base specified in (2-1) above in the guide strand, may have any one of:

```
                                      (SEQ ID NO. 148)
        5'-GGCUUCUGAUUUGCUACAU-3'

(SEQ ID NO. 149)
        5'-CCUCGAUGUCGAAGAGGUC-3'
```

-continued

```
                                      (SEQ ID NO. 150)
        5'-ACACCAGUUCGUCCCUUUC-3'

(SEQ ID NO. 151)
        5'-GGUACUUCUCGCUUGGUUU-3'

(SEQ ID NO. 152)
        5'-GAGGCCACAGGCAUUGCAC-3'

(SEQ ID NO. 153)
        5'-GAUGGGGAUCAGUCGCUUC-3'

(SEQ ID NO. 154)
        5'-CUCUGACCUUUGGCCCCCU-3'
        and (SEQ ID NO. 155)
        5'-AUAAGCAUGACGACCUAUG-3'.
```

In addition, one or more ribonucleotides in the aforementioned double-stranded RNA molecule(s) may be replaced by a deoxyribonucleotide, an artificial nucleic acid, or a nucleic acid analog.

[4-3] According to a further aspect of the present invention, in any one of the production methods described in [1-3], the gene is a BRCA2 gene, the wild-type allele is BRCA2 (wt), and the mutant allele is an A1114C mutant allele; or in any one of the aforementioned RNA molecules, the gene is an STK11 gene, the wild-type allele is STK11 (wt) and the mutant allele is a C1062G mutant allele; or in any one of the aforementioned RNA molecules, the gene is a PTEN gene, the wild-type allele is PTEN (wt), and the mutant allele is a C388G mutant allele; or in any one of the aforementioned RNA molecules, the gene is an APC gene, the wild-type allele is APC (wt), and the mutant allele is a C4348T mutant allele; or in any one of the aforementioned RNA molecules, the gene is a GATA2 gene, the wild-type allele is GATA2 (wt), and the mutant allele is a C953T mutant allele; or in any one of the aforementioned RNA molecules, the gene is an MYD88 gene, the wild-type allele MYD88 (wt), and the mutant allele is a T818C mutant allele; or in any one of the aforementioned RNA molecules, the gene is a GNAQ gene, the wild-type allele is GNAQ (wt), and the mutant allele is an A626T mutant allele; or in any one of the aforementioned RNA molecules, the gene is an IDH1 gene, the wild-type allele is IDH1 (wt), and the mutant allele is a G395A mutant allele.

In the aforementioned guide strand(s), a nucleotide sequence complementary to that of the coding region of the mutant allele, containing the base specified in (2-1) above in the guide strand, may have any one of:

```
                                      (SEQ ID NO. 148)
        5'-GGCUUCUGAUUUGCUACAU-3'

(SEQ ID NO. 149)
        5'-CCUCGAUGUCGAAGAGGUC-3'

(SEQ ID NO. 150)
        5'-ACACCAGUUCGUCCCUUUC-3'

(SEQ ID NO. 151)
        5'-GGUACUUCUCGCUUGGUUU-3'

(SEQ ID NO. 152)
        5'-GAGGCCACAGGCAUUGCAC-3'

(SEQ ID NO. 153)
        5'-GAUGGGGAUCAGUCGCUUC-3'
```

-continued (SEQ ID NO. 154)
```
5'-CUCUGACCUUUGGCCCCCU-3'
```
and (SEQ ID NO. 155)
```
5'-AUAAGCAUGACGACCUAUG-3'.
```

In addition, one or more ribonucleotides in the aforementioned double-stranded RNA molecule(s) may be replaced by a deoxyribonucleotide, an artificial nucleic acid, or a nucleic acid analog.

[4-4] According to a further aspect of the present invention, in any one of the methods for performing RNA interference described in [1-4], the gene is a BRCA2 gene, the wild-type allele is BRCA2 (wt), and the mutant allele is an A1114C mutant allele; or in any one of the aforementioned RNA molecules, the gene is an STK11 gene, the wild-type allele is STK11 (wt) and the mutant allele is a C1062G mutant allele; or in any one of the aforementioned RNA molecules, the gene is a PTEN gene, the wild-type allele is PTEN (wt), and the mutant allele is a C388G mutant allele; or in any one of the aforementioned RNA molecules, the gene is an APC gene, the wild-type allele is APC (wt), and the mutant allele is a C4348T mutant allele; or in any one of the aforementioned RNA molecules, the gene is a GATA2 gene, the wild-type allele is GATA2 (wt), and the mutant allele is a C953T mutant allele; or in any one of the aforementioned RNA molecules, the gene is an MYD88 gene, the wild-type allele MYD88 (wt), and the mutant allele is a T818C mutant allele; or in any one of the aforementioned RNA molecules, the gene is a GNAQ gene, the wild-type allele is GNAQ (wt), and the mutant allele is an A626T mutant allele; or in any one of the aforementioned RNA molecules, the gene is an IDH1 gene, the wild-type allele is IDH1 (wt), and the mutant allele is a G395A mutant allele.

In the aforementioned guide strand(s), a nucleotide sequence complementary to that of the coding region of the mutant allele, containing the base specified in (2-1) above in the guide strand, may have any one of:

(SEQ ID NO. 148)
```
5'-GGCUUCUGAUUUGCUACAU-3'
```
(SEQ ID NO. 149)
```
5'-CCUCGAUGUCGAAGAGGUC-3'
```
(SEQ ID NO. 150)
```
5'-ACACCAGUUCGUCCCUUUC-3'
```
(SEQ ID NO. 151)
```
5'-GGUACUUCUCGCUUGGUUU-3'
```
(SEQ ID NO. 152)
```
5'-GAGGCCACAGGCAUUGCAC-3'
```
(SEQ ID NO. 153)
```
5'-GAUGGGGAUCAGUCGCUUC-3'
```
(SEQ ID NO. 154)
```
5'-CUCUGACCUUUGGCCCCCU-3'
```
and
(SEQ ID NO. 155)
```
5'-AUAAGCAUGACGACCUAUG-3'.
```

In addition, one or more ribonucleotides in the aforementioned double-stranded RNA molecule(s) may be replaced by a deoxyribonucleotide, an artificial nucleic acid, or a nucleic acid analog.

[4-5] According to a further aspect of the present invention, in any one of the therapeutic agents described in [1-5], the oncogene is a BRCA2 gene, the wild-type allele is BRCA2 (wt), and the mutant allele is an A1114C mutant allele; or in any one of the aforementioned RNA molecules, the gene is an STK11 gene, the wild-type allele is STK11 (wt) and the mutant allele is a C1062G mutant allele; or in any one of the aforementioned RNA molecules, the gene is a PTEN gene, the wild-type allele is PTEN (wt), and the mutant allele is a C388G mutant allele; or in any one of the aforementioned RNA molecules, the gene is an APC gene, the wild-type allele is APC (wt), and the mutant allele is a C4348T mutant allele; or in any one of the aforementioned RNA molecules, the gene is a GATA2 gene, the wild-type allele is GATA2 (wt), and the mutant allele is a C953T mutant allele; or in any one of the aforementioned RNA molecules, the gene is an MYD88 gene, the wild-type allele MYD88 (wt), and the mutant allele is a T818C mutant allele; or in any one of the aforementioned RNA molecules, the gene is a GNAQ gene, the wild-type allele is GNAQ (wt), and the mutant allele is an A626T mutant allele; or in any one of the aforementioned RNA molecules, the gene is an IDH1 gene, the wild-type allele is IDH1 (wt), and the mutant allele is a G395A mutant allele.

In the aforementioned guide strand(s), a nucleotide sequence complementary to that of the coding region of the mutant allele, containing the base specified in (2-1) above in the guide strand, may have any one of:

(SEQ ID NO. 148)
```
5'-GGCUUCUGAUUUGCUACAU-3'
```
(SEQ ID NO. 149)
```
5'-CCUCGAUGUCGAAGAGGUC-3'
```
(SEQ ID NO. 150)
```
5'-ACACCAGUUCGUCCCUUUC-3'
```
(SEQ ID NO. 151)
```
5'-GGUACUUCUCGCUUGGUUU-3'
```
(SEQ ID NO. 152)
```
5'-GAGGCCACAGGCAUUGCAC-3'
```
(SEQ ID NO. 153)
```
5'-GAUGGGGAUCAGUCGCUUC-3'
```
(SEQ ID NO. 154)
```
5'-CUCUGACCUUUGGCCCCCU-3'
```
and
(SEQ ID NO. 155)
```
5'-AUAAGCAUGACGACCUAUG-3'.
```

In addition, one or more ribonucleotides in the aforementioned double-stranded RNA molecule(s) may be replaced by a deoxyribonucleotide, an artificial nucleic acid, or a nucleic acid analog.

[4-6] According to a further aspect of the present invention, in any one of the selection methods described in [1-6], the gene is a BRCA2 gene, the wild-type allele is BRCA2 (wt), and the mutant allele is an A1114C mutant allele; or in any one of the aforementioned RNA molecules, the gene is an STK11 gene, the wild-type allele is STK11 (wt) and the mutant allele is a C1062G mutant allele; or in any one of the aforementioned RNA molecules, the gene is a PTEN gene, the wild-type allele is PTEN (wt), and the mutant allele is a C388G mutant allele; or in any one of the aforementioned RNA molecules, the gene is an APC gene, the wild-type allele is APC (wt), and the mutant allele is a C4348T mutant allele; or in any one of the aforementioned RNA molecules, the gene is a GATA2 gene, the wild-type allele is GATA2 (wt), and the mutant allele is a C953T mutant allele; or in any one of the aforementioned RNA molecules, the gene is an MYD88 gene, the wild-type allele MYD88 (wt), and the mutant allele is a T818C mutant allele; or in any one of the aforementioned RNA molecules, the gene is a GNAQ gene, the wild-type allele is GNAQ (wt), and the mutant allele is an A626T mutant allele; or in any one of the aforementioned RNA molecules, the gene is an IDH1 gene, the wild-type allele is IDH1 (wt), and the mutant allele is a G395A mutant allele.

EMBODIMENTS OF THE INVENTION

Figure 1:
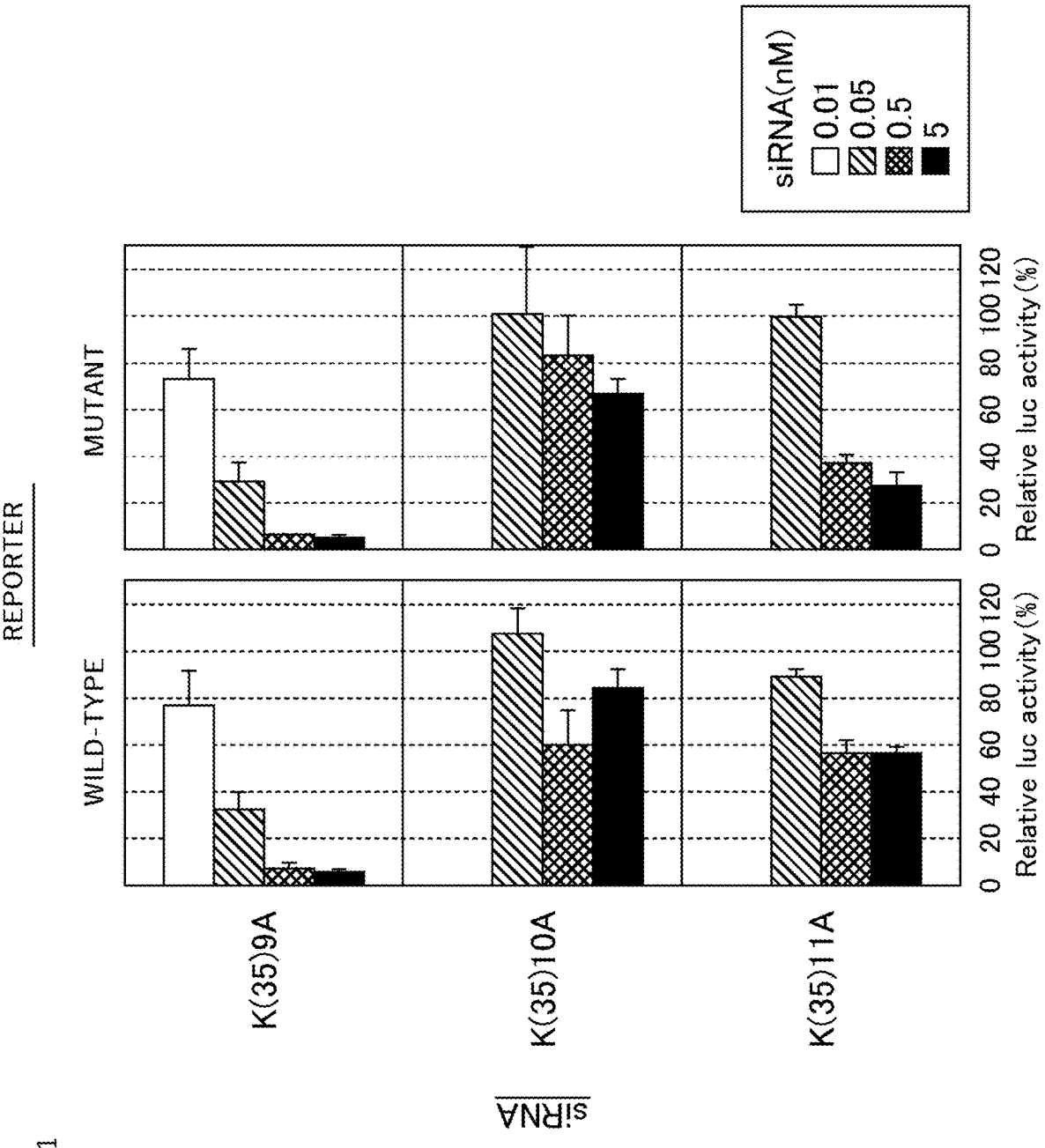
FIG. 1 shows graphs of results for silencing abilities of siRNAs designed to target K-ms gene, in each of which either one of positions 9-11 corresponded to the position of the point mutation, in one example of the present invention.

Objects, characteristics, advantages, and ideas of the present invention are apparent to a person skilled in the art from the description of the present specification, and the person skilled in the art can easily reproduce the present invention from the description of the present specification. Modes for carrying out the invention, specific examples thereof and so forth, which are described below, provide preferable embodiments of the present invention. They are described for the purpose of illustration or explanation, and thus the present invention is not limited thereto. It is apparent to a person skilled in the art that various alterations and modifications can be made on the basis of the description of the present specification within the spirit and the scope of the present invention disclosed in the present specification.

==RNA Molecules==

An embodiment of the present invention is RNA molecules for use in RNA interference intended to target a mutant allele with a point mutation of a single base relative to its wild-type allele of a gene. Any gene may be targeted as long as the RNA molecules according to the present disclosure can be designed for. Still, the target gene is preferably an oncogene that can transform normal cells by a point mutation. The RNA molecules herein may consist of any number of nucleotides, and the number may be 13 or more and 100 or less, 13 or more and 50 or less, 13 or more and 28 or less, 15 or more and 25 or less, or 17 or more and 21 or less. More preferably, the number is 19 or more and 21 or less. One or more (which may be 2 or more and 18 or less, 2 or more and 15 or less, 2 or more and 12 or less, 2 or more and 9 or less, 2 or more and 6 or less, or 2 or 3) ribonucleotides may be replaced by a deoxyribonucleotide, an artificial nucleic acid, or a nucleic acid analog such as inosine or morpholino. Such RNA molecules are herein called "chimeric NA molecules," and the RNA molecules are described as including chimeric NA molecules in the present disclosure.

In the RNA molecules, a base at position 5 or 6, counted from the base at the 5'-end of a nucleotide sequence complementary to that of the mutant allele, is mismatched with the base of the mutant allele, while the RNA molecules have a nucleotide sequence complementary to that of a coding region of the mutant allele in the rest of the sequence. The RNA molecules may also have a sequence other than the nucleotide sequence complementary to that of the coding region of the mutant allele, such as a sequence complementary to the complementary nucleotide sequence, with which the molecules may be self-annealed to function as siRNA. Bonac nucleic acid is an example of such a single-stranded RNA. Moreover, 1-3 nucleotide(s) may be added to the 3'-end, whose nucleotide sequences are not limited. In the case that the base at the 5'-end of the complementary nucleotide sequence is not adenine or uracil, it may be replaced by adenine or uracil or thymine. In the case that the base at the 3'-end of the complementary nucleotide sequence is not cytosine or guanine, it may be replaced by cytosine or guanine. These modifications enhance the ability of the RNA molecules to suppress gene expression when they work as siRNA guide strands. The RNA molecules may also contain chemical substances in addition to the nucleic acids for delivery, for increasing membrane permeability, or for improving retention in the blood. For example, the RNA molecules may be conjugated to GalNAc or PEG. The RNA molecules may be composed of a sequence other than the nucleotide sequence complementary to that of the coding region of the mutant allele except for the base at position 5 or 6. It should be noted that the RNA molecules have a nucleotide sequence complementary to that of the mutant allele except for the base at position 5 or 6, and their sequence complementarity is preferably 90% or more, more preferably 95% or more, yet more preferably 98% or more, and most preferably 100%. The base at position 5 or 6 may be any base as long as it is mismatched with that of the mutant allele. The base may be A, U, C, G, T, I, or any other artificial nucleic acid or nucleic acid analog, as long as the base is not identical to the base in the corresponding location of the mutant allele.

Moreover, in the RNA molecules, a base at position 10 or 11, when counted from the base at the 5'-end of the nucleotide sequence complementary to that of the mutant allele, corresponds to the position of the point mutation. The base at position 10 or 11 is identical to the base in the corresponding location of the mutant allele. In the case that the mutated base in the mutant allele is adenine, cytosine, guanine, or thymine, the base at position 10 or 11 of the RNA molecules is adenine, cytosine, guanine, or uracil (or thymine), respectively.

In the RNA molecules, a group at the 2'-position of a pentose in each of their nucleotides at positions 6-8 or positions 7 and 8, counted from the base at the 5'-end of the nucleotide sequence complementary to that of the mutant allele, is modified with (i.e., replaced by) $OCH_3$, halogen, or LNA. For example, RNA in which the 2'-position of a pentose is replaced by —$OCH_3$ (hereinafter referred to as 2'-O-methyl RNA) has a structure represented by the following general formula:

[Chemical 1]

Any halogen may be used, but fluorine is preferred because of its small molecular size. For nucleotides at locations other than those mentioned, some or all of them may be modified; however, it is preferable that none of them is modified. Modifications of nucleotides are not particularly limited, and exemplified that a group at the 2'-position of a pentose in the nucleotides is replaced by a group selected from the group consisting of H, OR, R, halogen, SH, SR, $NH_2$, NHR, $NR_2$, CN, COOR, and LNA (wherein R is $C_1$-$C_6$ alkyl, alkenyl, alkynyl, or aryl; and halogen is F, Cl, Br, or I).

The $IC_{50}$ of the RNA molecules for the target gene is preferably 1 nM or less, more preferably 500 pM or less, and yet more preferably 200 pM or less.

When the RNA molecules are used for RNA interference as a single strand, it is preferable that their 5'-end is phosphorylated or can be phosphorylated in situ or in vivo.

A method of designing the RNA molecules includes the following steps.

First, a nucleotide sequence of a given length containing a sequence complementary to that of a mutant allele is determined, with a mutated base in the mutant allele being placed at tenth or eleventh position, counted from the base at the 5'-end. The next step is to place a mismatched base at position 5 or 6, counted from the base at the 5'-end. Then, the group at the 2'-position of the pentose in each of nucleotides at positions 6-8 or positions 7 and 8, counted from the base at the 5'-end, is modified with $OCH_3$, halogen, or LNA. In the case that the base at the 5'-end of the complementary nucleotide sequence is not adenine or uracil, the step of replacing it by adenine or uracil or thymine may be performed. Likewise, in the case that the base at the 3'-end of the complementary nucleotide sequence is not cytosine or guanine, the step of replacing it by cytosine or guanine may be performed. Finally, 1-3 base(s) may be added to the 3'-end. In this way, a nucleotide sequence can be designed. A program for causing a computer to perform this design method may be prepared, and the program may be stored in a computer-readable recording medium. Nucleotides having a sequence designed in this manner can be chemically synthesized according to a routine method.

==Double-Stranded RNA Molecules==

An embodiment of the present invention is double-stranded RNA molecules in which an RNA molecule described above (hereinafter referred to as a "first RNA molecule) serves as a guide strand and a second RNA molecule with a sequence complementary to that of the first RNA molecule serves as a passenger strand. The second RNA molecule has a sequence complementary to that of the first RNA molecule and forms a duplex with the first RNA molecule under physiological conditions. Their sequence complementarity is preferably 90% or more, more preferably 95% or more, yet more preferably 98% or more, and most preferably 100%.

The passenger strand may have any length and may be considerably shorter than the first RNA molecule. For example, the length of the passenger strand may be equal to or less than half the length of the first RNA molecule. It is, however, preferable that they have the same length. When the passenger strand is shorter than the first RNA molecule, the latter will have a single-stranded portion. This portion may be left single-stranded, or alternatively, a third RNA molecule complementary to the first RNA molecule may be annealed to the single-stranded portion. In the case that the second and third RNA molecules occupy the entire length of the first RNA molecule, the resulting double strand is identical to the one with a nick present on a single passenger strand to divide it into two.

The double-stranded RNA molecules may have two blunt ends, or alternatively, they may have an overhang at the 3'-end of either or both first and second RNA molecules serving as the guide and passenger strands, respectively. The overhang(s) may have any number of nucleotides, but is/are preferably of 1-3 nucleotide(s) long.

The nucleotide strands of the guide and passenger strands may be a double-stranded chimeric NA molecule in which one or more ribonucleotides are replaced by deoxyribo-nucleotides, artificial nucleic acids, or nucleic acid analogs.

The nucleotides in the passenger strand may be modified; however, it is preferable that they are not modified. Modifications of nucleotides are not particularly limited, and, for example, a group at the 2'-position of a pentose in the nucleotides may be replaced by a group selected from the group consisting of H, OR, R, halogen, SH, $SR_1$, $NH_2$, NHR, $NR_2$, CN, COOR, and LNA (wherein R is $C_1$-$C_6$ alkyl, alkenyl, alkynyl, or aryl; and halogen is F, Cl, Br, or I).

Passenger strands can also be easily designed and easily produced using known techniques. A guide strand and a passenger strand may be linked to each other by a linker. The linker may be formed of any material, and examples include peptides and PEG.

==RNA Interference==

An embodiment of the present invention is a method for performing RNA interference by which a mutant allele with a point mutation is targeted in cells containing the wild-type allele of a gene of interest and a mutant allele of the gene. This method includes the step of introducing a first RNA molecule including a chimeric NA molecule, or one of the aforementioned double-stranded RNA molecules including a double-stranded chimeric NA molecule, into the cells containing the wild-type allele and the mutant allele.

RNA interference can be readily performed using known techniques. The expression of a target gene can be reduced by introducing first RNA molecules or double-stranded RNA molecules into, for example, culture cells or a human or non-human individual organism expressing the target gene.

The use of the aforementioned first RNA molecules or double-stranded RNA molecules in RNA interference makes it possible to primarily suppress the expression of the mutant allele of the gene of interest, substantially without suppressing the expression of the wild-type allele. Here, the expression of the wild-type allele may be suppressed up to the extent that the wild-type allele is functional and a normal phenotype is exhibited. The expression of the mutant allele should be inhibited at least to the extent that the mutant allele is not functional and an abnormal phenotype is not exhibited. This enables, for example, cells to become functional normally without developing a phenotype due to a mutation even when the mutant allele carries a dominant mutation.

==Therapeutic Agents==

When the siRNAs of the present disclosure are used as a therapeutic agent, the target disease is not limited. An embodiment of the present invention is therapeutic agents for patients with a tumor including tumor cells each having a wild-type allele of an oncogene (sometimes also referred to as a proto-oncogene, tumor suppressor gene, cancer suppressor gene, etc.) and a mutant allele of the oncogene, the mutant allele having a point mutation, the point mutation being responsible for tumorigenesis, and the therapeutic agents include, as an active ingredient, the aforementioned RNA molecules including the chimeric NA molecules, or the aforementioned double-stranded RNA molecules including the double-stranded chimeric NA molecules.

Any method can be used for administration; however, injection is preferable, and intravenous injection is more preferable. In such cases, in addition to the active ingredient, other ingredients such as pH adjusters, buffers, stabilizers, tonicity adjusting agents, or local anesthetics may be added to the therapeutic agents.

The dosage of the therapeutic agents is not limited and is selected as appropriate based on, for example, the efficacy of the ingredients contained, the mode of administration, the route of administration, the type of disease, attributes of a subject (e.g., weight, age, medical conditions, and history of use of other medicaments), and the discretion of a physician in charge.

==Target Diseases of the Therapeutic Agents==

The diseases for which siRNAs of the present disclosure are used as a therapeutic agent are not limited as long as they are caused by expression of a mutant gene, but are preferably tumors as described above. In the examples described below, the K-ras, N-ras, BRCA, STK11, PTEN, APC, GATA2, MYD8, GNAQ, and IDH1 genes were subject to suppression. It is known that mutations in the K-ras gene can cause, for example, colon, lung, and pancreatic cancers, and leukemia; mutations in the N-ras gene can cause, for example, colon, thyroid, and skin cancers; mutations in the BRCA gene can cause, for example, breast and ovarian cancers; mutations in the STK11 gene can cause, for example, adenoma malignum of the cervix, Peutz-Jeghers syndrome, and gastric, breast, and ovarian cancers; mutations in the PTEN gene can cause, for example, PTEN hamartoma tumor syndrome such as Cowden syndrome, Lhermitte-Duclos disease, Bannayan-Riley-Ruvalcaba syndrome, and Proteus syndrome; mutations in the APC gene can cause, for example, familial adenomatous polyposis (FAP) and liver cancer; mutations in the GATA2 gene can cause, for example, MonoMAC syndrome and acute megakaryoblastic leukemia; mutations in the MYD88 gene can cause, for example, lymphoma; mutations in the GNAQ gene can cause, for example, uveal melanoma, Sturge-Weber syndrome, and GNAS- and BRCA-hemangioma; and mutations in the IDH1 gene can cause, for example, gliomas. The siRNAs can be used as therapeutic agents for at least these diseases.

==Selection Methods==

An embodiment of the present invention is a selection method for selecting RNA molecules, chimeric NA molecules, double-stranded RNA molecules, or double-stranded chimeric NA molecules for use in RNA interference to silence a target gene, and the selection method includes the steps of performing RNA interference in vitro using a plurality of the aforementioned RNA molecules, chimeric NA molecules, double-stranded RNA molecules, or double-stranded chimeric NA molecules and thereby evaluating their gene-specific silencing abilities; and selecting RNA molecules, chimeric NA molecules, double-stranded RNA molecules, or double-stranded chimeric NA molecules having a certain level or higher level of gene-specific silencing ability.

In performing RNA interference in vitro, a wild-type allele and a mutant allele with a point mutation, of a gene are used as a target gene, and a molecule is selected that does not suppress the expression of the wild-type allele over a given level but suppresses the expression of the mutant allele over a given level. By this procedure, one or more molecules that suppress the expression of the mutant allele without suppressing the expression of the wild-type allele can be obtained. Here, the given level may have any numerical value, but is preferably 50%, more preferably 70%, and even more preferably 90%.

Methods for the assay using RNA interference in vitro are common knowledge in the art, and the selection of genes, selection of cells, and introduction of RNA molecules into cells, etc. are obvious to those skilled in the art.

EXAMPLES

Example 1

This example shows, using the expression of exogenous reporters in culture cells, that the siRNAs disclosed herein specifically suppress the expression of mutant alleles without suppressing the expression of the wild-type allele. (Methods)

HeLa cells cultured in DMEM supplemented with 10% FBS were seeded at $1 \times 10^5$ cells/mL on 24-well plates and co-transfected with each double-stranded siRNA with 100 ng of a reporter and 100 ng of plasmid (pGL3) as an internal standard, using 2 μL of lipofectamine 2000. The concentrations of the double-stranded siRNAs are given in the figures. siGY441 was introduced as control for siRNA. Cells were harvested after 24 hours, and firefly and *Renilla* luciferase activities were measured using the Dual-luciferase Reporter Assay System (Promega). *Renilla* luciferase activity was normalized by the firefly luciferase activity. The results obtained for the double-stranded siRNAs were presented in the graphs, relative to those for siGY441 which were set to 100%.

Example 1A

In this example, the K-ras gene was used as a target gene to be silenced.

Example 1A-1

This example shows that, by matching position 10 or 11 of each siRNA with the position of the point mutation in an A-mutant K-ras (c. 35G>A) allele (with a mutation from G to A at position 35 in the cDNA (GENE ID: 3845)) (hereinafter, referred to as an "A-mutant allele"), the RNA molecules exhibit an higher specificity for silencing abilities to the A-mutant K-ras (35G>A) allele than to the wild-type K-ras allele (hereinafter, referred to as a "wild-type allele").

First, as reporters for examining gene silencing effects, DNAs having the same nucleotide sequence as either of the wild-type K-ras (wt) allele and the A-mutant K-ms (c. 35G>A) allele were chemically synthesized and inserted into the 3'-UTR of the luciferase gene in an expression vector (psiCHECK) to construct wild-type and A-mutant K reporters. The sequences of the segments incorporated into the vectors are indicated below.

```
Wild-type K reporter:
                                   (SEQ ID NO. 4)
5'-TGGTAGTTGGAGCTG G TGGCGTAGGCAAGAGTG-3'

(SEQ ID NO. 5)
3'-ACCATCAACCTCGAC C ACCGCATCCGTTCTCAC-5'

A-mutant K reporter:
                                   (SEQ ID NO. 6)
5'-TGGTAGTTGGAGCTG A TGGCGTAGGCAAGAGTG-3'

(SEQ ID NO. 7)
3'-ACCATCAACCTCGAC T ACCGCATCCGTTCTCAC-5'
```

Next, double-stranded RNAs with the following sequence were chemically synthesized as siRNAs. The positions 9, 10, and 11 in siRNAs, K(35)9A, K(35)10A, and K(35)11A, respectively, correspond to the position of point mutation in the A-mutant K-ms (c. 35G>A) allele. In the following sequences, base pairs in the location corresponding to the position of the point mutation are enclosed in rectangles.

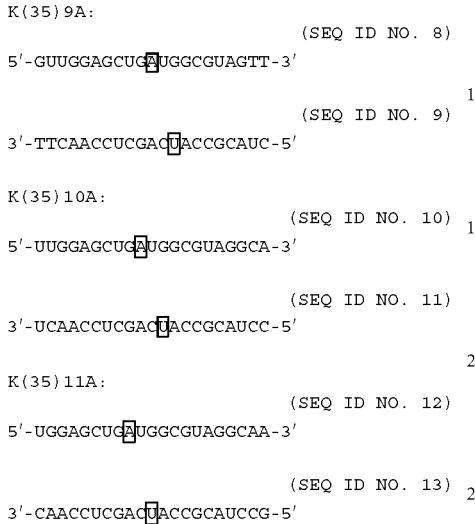

```
K(35)9A:
                            (SEQ ID NO. 8)
5'-GUUGGAGCUGAUGGCGUAGTT-3'

(SEQ ID NO. 9)
3'-TTCAACCUCGACUACCGCAUC-5'

K(35)10A:
                            (SEQ ID NO. 10)
5'-UUGGAGCUGAUGGCGUAGGCA-3'

(SEQ ID NO. 11)
3'-UCAACCUCGACUACCGCAUCC-5'

K(35)11A:
                            (SEQ ID NO. 12)
5'-UGGAGCUGAUGGCGUAGGCAA-3'

(SEQ ID NO. 13)
3'-CAACCUCGACUACCGCAUCCG-5'
```

FIG. 1 shows gene silencing effects of each siRNA.

K(35)9A had a strong silencing effect on both A-mutant and wild-type alleles. K(35)10A and K(35) 11A strongly suppress the expression of the A-mutant allele over the wild-type allele although their silencing effects were slightly reduced.

Example 1A-2

This example shows that by using an siRNA whose position 11 is matched with the position of the point mutation in the A-mutant allele, and in which the base at the 5'-end of the guide strand is replaced from guanine to uracil, and the base at the 5'-end of the passenger strand is replaced from uracil to guanine, the silencing abilities of the RNA molecules to the A-mutant allele become higher and their specificities become much higher.

The wild-type and A-mutant K reporters were used as reporters for examining gene silencing effects. An double-stranded RNA with the following sequence was chemically synthesized as siRNA, and K(35)11A was used as a control. In the following sequences, a base pair in the location corresponding to the position of the point mutation, and pairs of the replaced bases at the 5'-ends of the guide and passenger strands, respectively, and their counterparts are enclosed in rectangles.

```
K(35)11Arev:
                            (SEQ ID NO. 14)
5'-GGGAGCUGAUGGCGUAGGAAA-3'

(SEQ ID NO. 15)
3'-CACCCUCGACUACCGCAUCCU-5'
```

Figure 2:
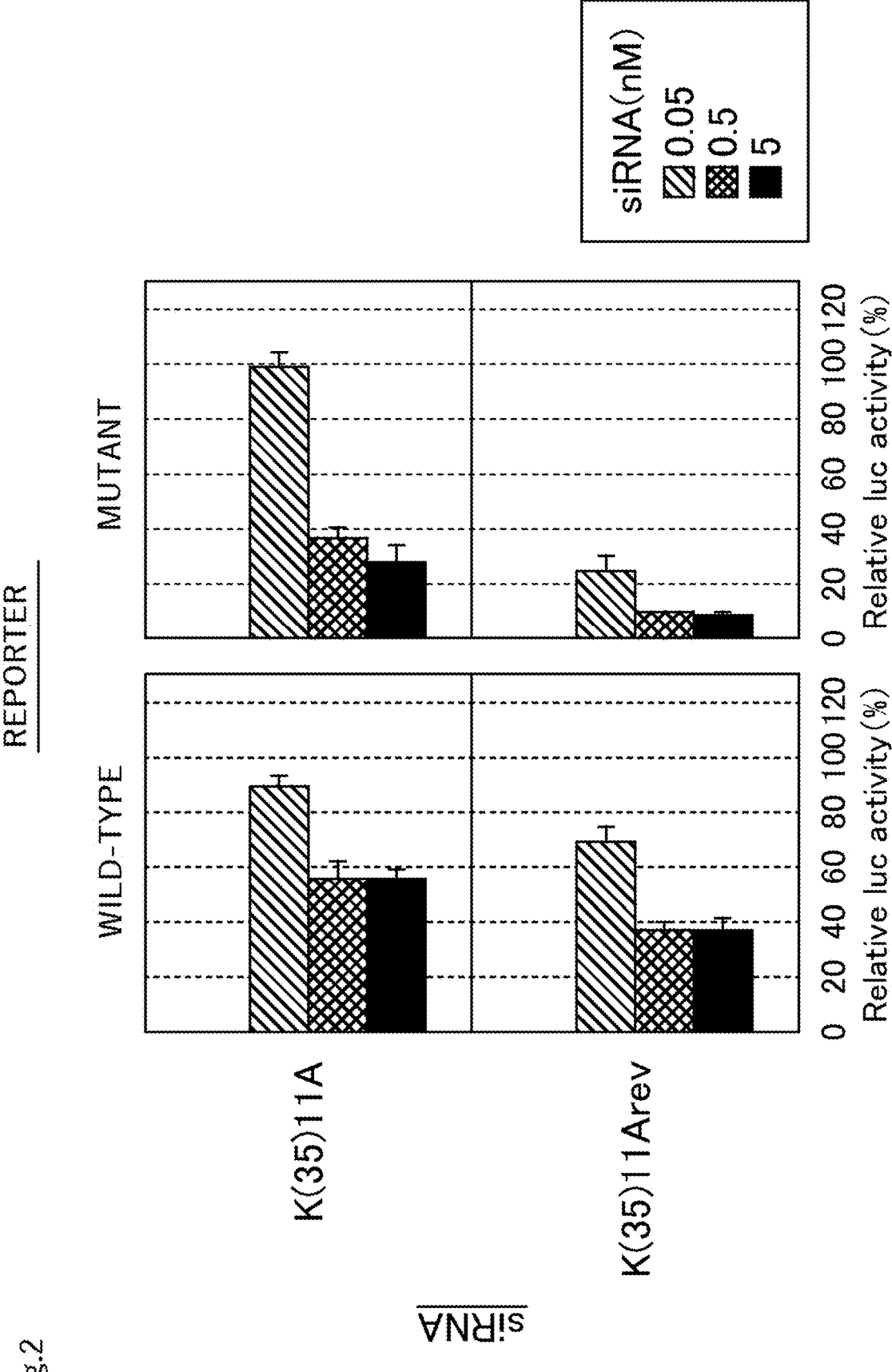
FIG. 2 shows graphs of results for silencing abilities of an siRNA designed to target K-ms gene, in which position 11 corresponded to the position of the point mutation, the base at the 5'-end of the guide strand was replaced from guanine to uracil, and the base at the 5'-end of the passenger strand was replaced from uracil to guanine, in one example of the present invention.

FIG. 2 shows gene silencing effects of each siRNA.

K(35)11A strongly suppressed the expression of the A-mutant allele over the wild-type allele, whereas K(35) 11Arev exerted a stronger silencing effect on both, with enhanced suppression of the expression of the A-mutant allele over the wild-type allele.

Example 1A-3

This example shows that by matching position 11 of the siRNA molecules with the position of the point mutation in the A-mutant allele, replacing the base at the 5'-end of the guide strand from guanine to uracil, replacing the base at the 5'-end of the passenger strand from uracil to guanine, and replacing the group at 2'-position of a pentose in each of ribonucleotides at positions 6-8 of the guide strand of the siRNA with OCH₃, silencing abilities of the RNA molecules to the A-mutant allele become stronger and their specificities become much higher.

The wild-type and A-mutant K reporters were used as reporters for examining gene silencing effects. Double-stranded RNAs with the following sequence were chemically synthesized as siRNAs, and K(35)11Arev was used as a control. In the following sequences, the base pairs corresponding to the position of the point mutation, and the replaced base pairs at the 5'-ends of the guide and passenger strands are enclosed in rectangles. The nucleotides in which the group at the 2'-position of the pentose was replaced by $OCH_3$ are hatched.

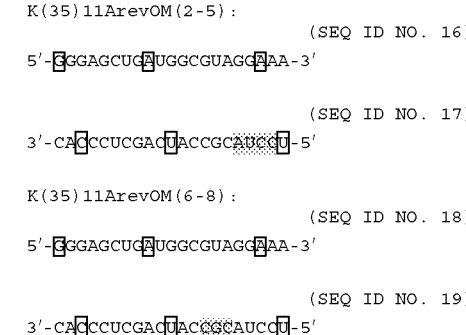

```
K(35)11ArevOM(2-5):
                            (SEQ ID NO. 16)
5'-GGGAGCUGAUGGCGUAGGAAA-3'

(SEQ ID NO. 17)
3'-CACCCUCGACUACCGCAUCCU-5'

K(35)11ArevOM(6-8):
                            (SEQ ID NO. 18)
5'-GGGAGCUGAUGGCGUAGGAAA-3'

(SEQ ID NO. 19)
3'-CACCCUCGACUACCGCAUCCU-5'
```

Figure 3:
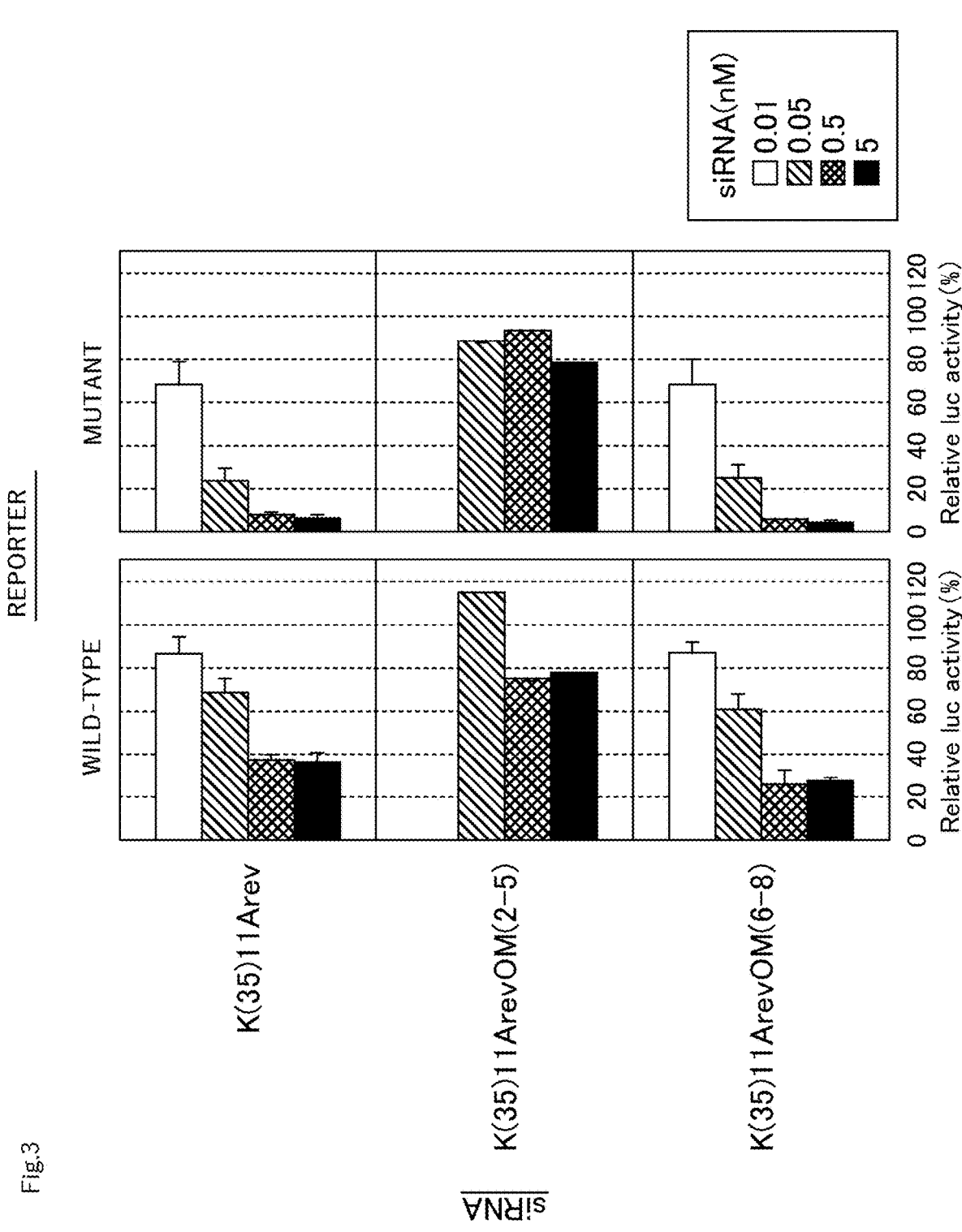
FIG. 3 shows graphs of results for silencing abilities of an siRNA designed to target K-ms gene, in which position 11 corresponded to the position of the point mutation, the base at the 5'-end of the guide strand was replaced from guanine to uracil, the base at the 5'-end of the passenger strand was replaced from uracil to guanine, and the group at the 2'-position of a pentose in each of ribonucleotides at positions 6-8 of the guide strand was replaced by $OCH_3$, in one example of the present invention.

FIG. 3 shows gene silencing effects of each siRNA.

K(35)1 1Arev strongly suppressed the expression of the A-mutant allele more than that of the wild-type allele, whereas K(35)11ArevOM(6-8) exerted a stronger silencing effect on both, with stronger suppression of the expression of the A-mutant allele than that of the wild-type allele. Another control, K(35)11ArevOM(2-5) (in which the group at the 2'-position of a pentose in each of ribonucleotides at positions 2-5 of the guide strand was replaced by $OCH_3$) exerted considerably weak silencing effect on both.

Example 1A-4

This example shows that by matching position 11 of the siRNAs with the position of the point mutation in the A-mutant allele, replacing the base at the 5'-end of the guide strand of the siRNAs from guanine to uracil, replacing the base at the 5'-end of the passenger strand thereof from uracil to guanine, and mismatching the base at position 5 or 6 of the guide strand of the siRNAs with that of the A-mutant allele, silencing abilities to the wild-type allele become weaker and, as a result, specificity to the A-mutant allele become much higher.

The wild-type and A-mutant K reporters were used as reporters for examining gene silencing effects. Double-stranded RNAs with the following sequences with a mismatched base at one of positions 3-7 based on K(35)1 1Arev were chemically synthesized as siRNAs. K(35)1 1Arev was used as a control. In the following sequences, the base pairs corresponding to the position of the point mutation, the replaced base pairs at the 5'-ends of the guide and passenger strands, and base pairs with the mismatched base are enclosed in rectangles.

```
K(35)11ArevM3:
                              (SEQ ID NO. 20)
5'-GGGAGCUGAUGGCGUACGAAA-3'

(SEQ ID NO. 21)
3'-CACCCUCGACUACCGCAUGCU-5'

K(35)11ArevM4:
                              (SEQ ID NO. 22)
5'-GGGAGCUGAUGGCGUUGGAAA-3'

(SEQ ID NO. 23)
3'-CACCCUCGACUACCGCAACCU-5'

K(35)11ArevM5:
                              (SEQ ID NO. 24)
5'-GGGAGCUGAUGGCGAAGGAAA-3'

(SEQ ID NO. 25)
3'-CACCCUCGACUACCGCUUCCU-5'

K(35)11ArevM6:
                              (SEQ ID NO. 26)
5'-GGGAGCUGAUGGCGUAGGAAA-3'

(SEQ ID NO. 27)
3'-CACCCUCGACUACCGGAUCCU-5'

K(35)11ArevM7:
                              (SEQ ID NO. 28)
5'-GGGAGCUGAUGGGGUAGGAAA-3'

(SEQ ID NO. 29)
3'-CACCCUCGACUACCGCAUCCU-5'
```

Figure 4:
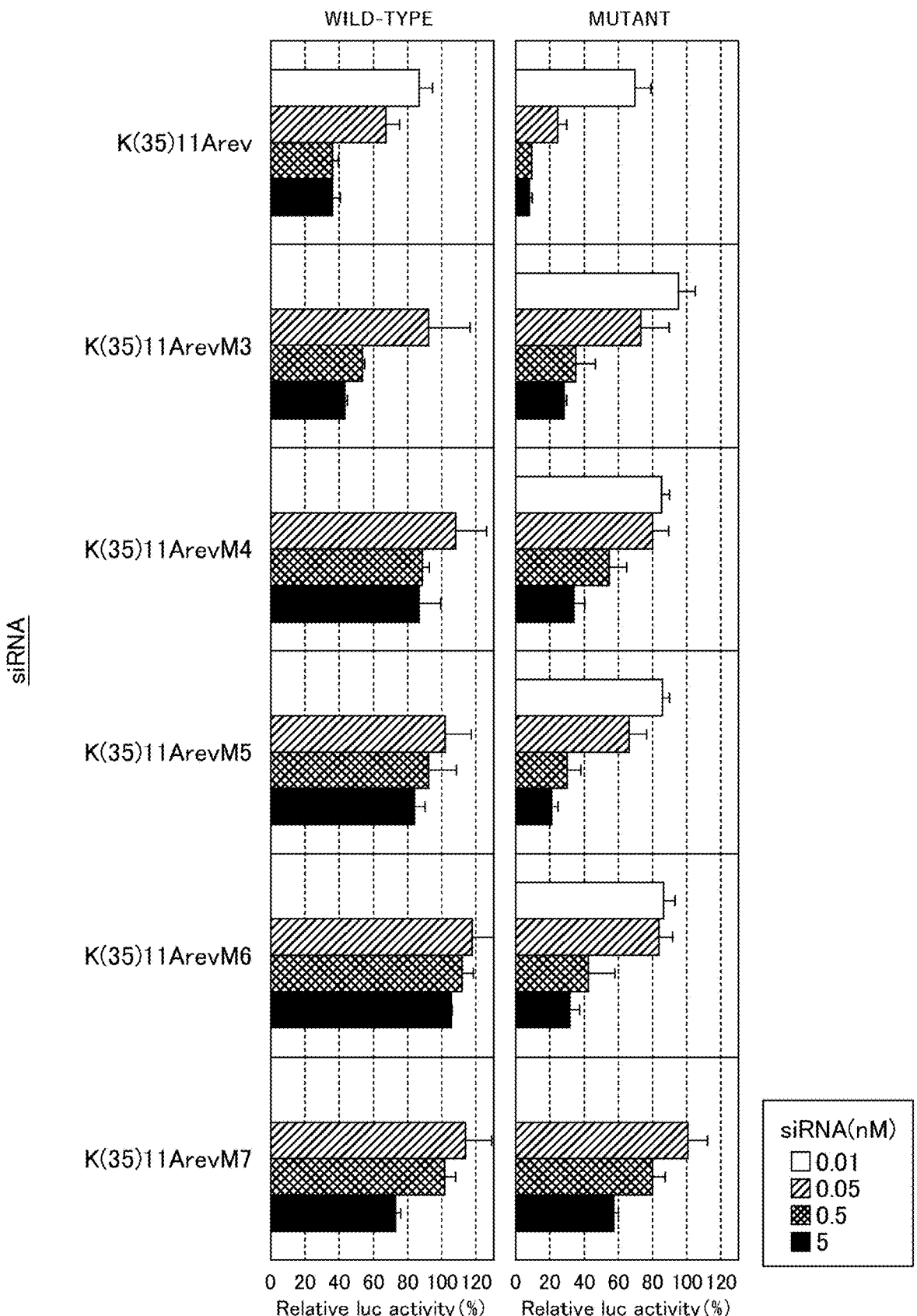
FIG. 4 shows graphs of results for silencing abilities of siRNAs designed to target K-ms gene, in each of which position 11 corresponded to the position of the point mutation, the base at the 5'-end of the guide strand was replaced from guanine to uracil, the base at the 5'-end of the passenger strand was replaced from uracil to guanine, and the base at either one of positions 3-7 is mismatched with that of the A-mutant allele, in one example of the present invention.

FIG. 4 shows gene silencing effects of each siRNA.

K(35)1 1Arev strongly suppressed the expression of the A-mutant allele over the wild-type allele, whereas RNA molecules K(35)11ArevM5 and K(35)11ArevM6 exhibited significantly poor silencing abilities to the wild-type allele, resulting in a much more enhanced specificity for the A-mutant allele.

Example 1A-5

This example shows that, by matching position 11 of the siRNAs with the position of the point mutation in the A-mutant allele, replacing the base at the 5'-end of the guide strand of the siRNAs from guanine to uracil, replacing the base at the 5'-end of the passenger strand thereof from uracil to guanine, replacing the group at the 2'-position of a pentose in each of ribonucleotides at positions 6-8 of the guide strand of the siRNAs with OCH₃, and mismatching the base at position 5 or 6 of the guide strand of the siRNA with the base of the A-mutant allele, the specificity to the A-mutant allele become much more higher.

The wild-type and A-mutant K reporters were used as reporters for examining gene silencing effects. Double-stranded RNAs with the following sequence with a mismatched base at one of positions 3-7 based on K(35)1 1Arev were chemically synthesized. K(35)1 1Arev was used as a control. In the following sequences, the base pairs corresponding to the position of the point mutation, the replaced base pairs at the 5'-ends of the guide and passenger strands, and base pairs with the mismatched base are enclosed in rectangles. The nucleotides in which the group at the 2'-position of the pentose was replaced with $OCH_3$ are hatched.

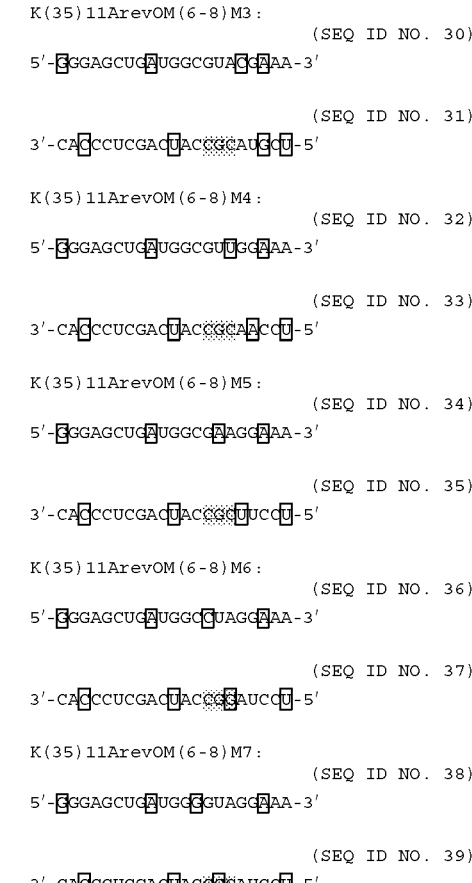

```
K(35)11ArevOM(6-8)M3:
                              (SEQ ID NO. 30)
5'-GGGAGCUGAUGGCGUACGAAA-3'

(SEQ ID NO. 31)
3'-CACCCUCGACUACCGCAUGCU-5'

K(35)11ArevOM(6-8)M4:
                              (SEQ ID NO. 32)
5'-GGGAGCUGAUGGCGUUGGAAA-3'

(SEQ ID NO. 33)
3'-CACCCUCGACUACCGCAACCU-5'

K(35)11ArevOM(6-8)M5:
                              (SEQ ID NO. 34)
5'-GGGAGCUGAUGGCGAAGGAAA-3'

(SEQ ID NO. 35)
3'-CACCCUCGACUACCGCUUCCU-5'

K(35)11ArevOM(6-8)M6:
                              (SEQ ID NO. 36)
5'-GGGAGCUGAUGGCGUAGGAAA-3'

(SEQ ID NO. 37)
3'-CACCCUCGACUACCGGAUCCU-5'

K(35)11ArevOM(6-8)M7:
                              (SEQ ID NO. 38)
5'-GGGAGCUGAUGGGGUAGGAAA-3'

(SEQ ID NO. 39)
3'-CACCCUCGACUACCGCAUCCU-5'
```

Figure 5:
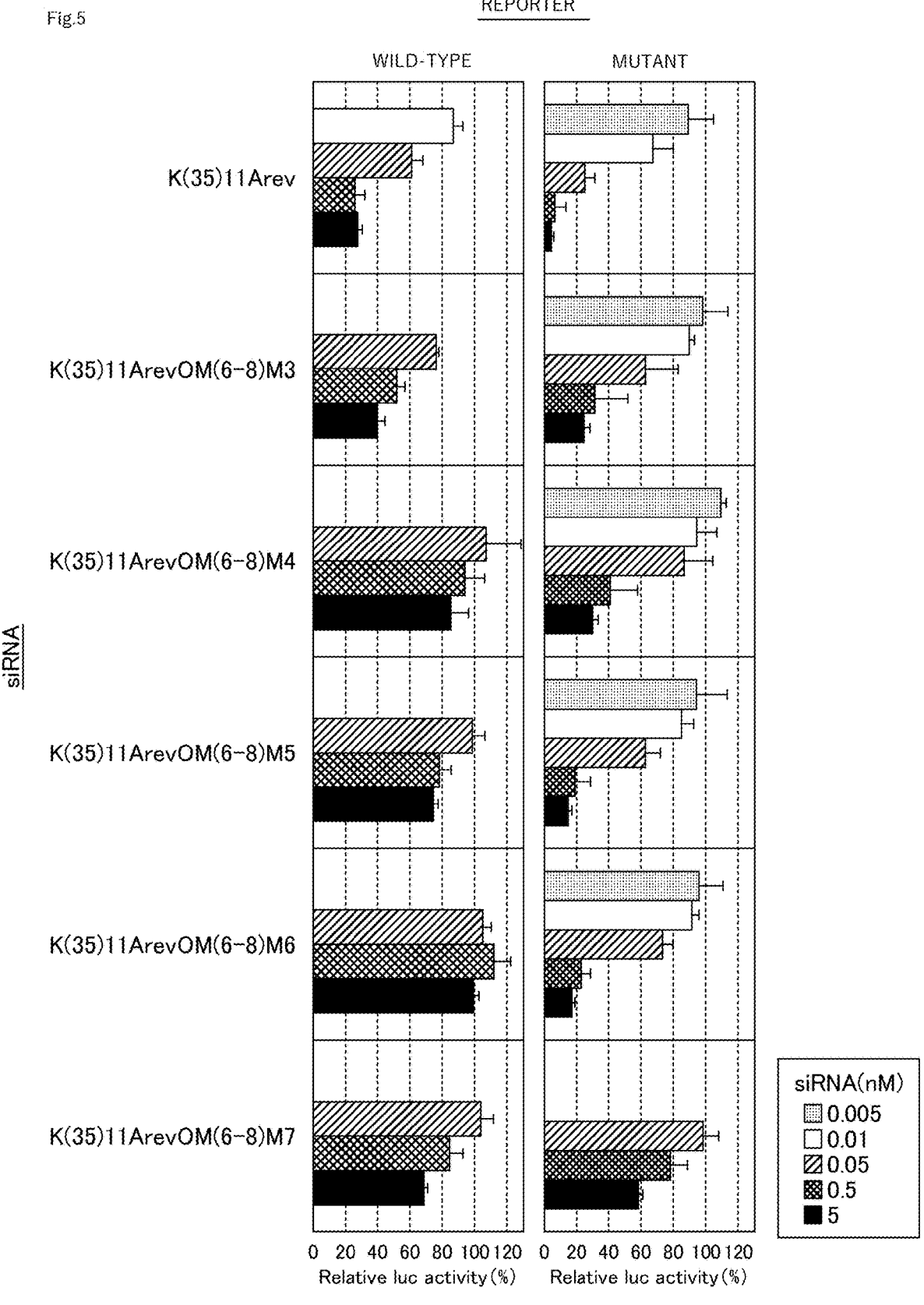
FIG. 5 shows graphs of results for silencing abilities of siRNAs designed to target K-ms gene, in each of which position 11 corresponded to the position of the point mutation, the base at the 5'-end of the guide strand was replaced from guanine to uracil, the base at the 5'-end of the passenger strand was replaced from uracil to guanine, the group at the 2'-position of a pentose in each of ribonucleotides at positions 6-8 of the guide strand was replaced by $OCH_3$, and the base at either one of positions 3-7 of the guide strand is mismached for the A-mutant allele, in one example of the present invention.

FIG. 5 shows gene silencing effects of each siRNA.

K(35)11ArevOM(6-8)M5 and K(35)11ArevOM(6-8)M6 exhibited very weak silencing abilities to the wild-type allele, resulting in a much higher specificity for the A-mutant allele.

Example 1A-6

This example shows that siRNAs specific for the A-mutant allele exhibit weak silencing abilities not only to the wild-type allele, but also a T-mutant K-ms (c. 35G>T) allele (with a mutation from G to T at position 35 in the cDNA) and a C-mutant K-ms (c. 35 G>C) allele (with a mutation from G to C at position 35 in the cDNA).

The wild-type and A-mutant K reporters as well as a T-mutant K-ms (c. 35G>T) reporter (hereinafter, referred to as a "T-mutant K reporter"), and a C-mutant K-ms (c. 35 G>C) reporter (hereinafter, referred to as a "C-mutant K reporter"), which are all K-ms reporters indicated below, were used as reporters for examining gene silencing effects. K(35)11ArevOM(6-8)M5 and K(35)11ArevOM(6-8)M6 were used as siRNAs, and K(35)11Arev was used as a control. In the following sequences, the base pairs corresponding to the position of the point mutation are enclosed in rectangles.

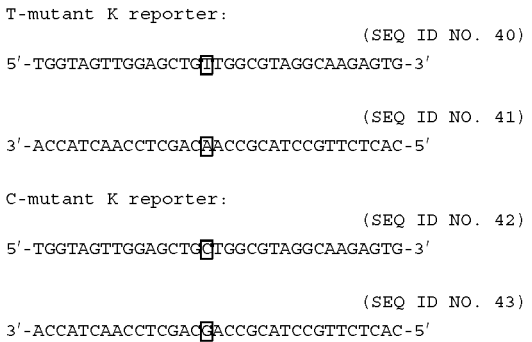

```
T-mutant K reporter:
                                    (SEQ ID NO. 40)
5'-TGGTAGTTGGAGCTGΔTGGCGTAGGCAAGAGTG-3'

(SEQ ID NO. 41)
3'-ACCATCAACCTCGACΔACCGCATCCGTTCTCAC-5'

C-mutant K reporter:
                                    (SEQ ID NO. 42)
5'-TGGTAGTTGGAGCTGΔTGGCGTAGGCAAGAGTG-3'

(SEQ ID NO. 43)
3'-ACCATCAACCTCGACΔACCGCATCCGTTCTCAC-5'
```

Figure 6:
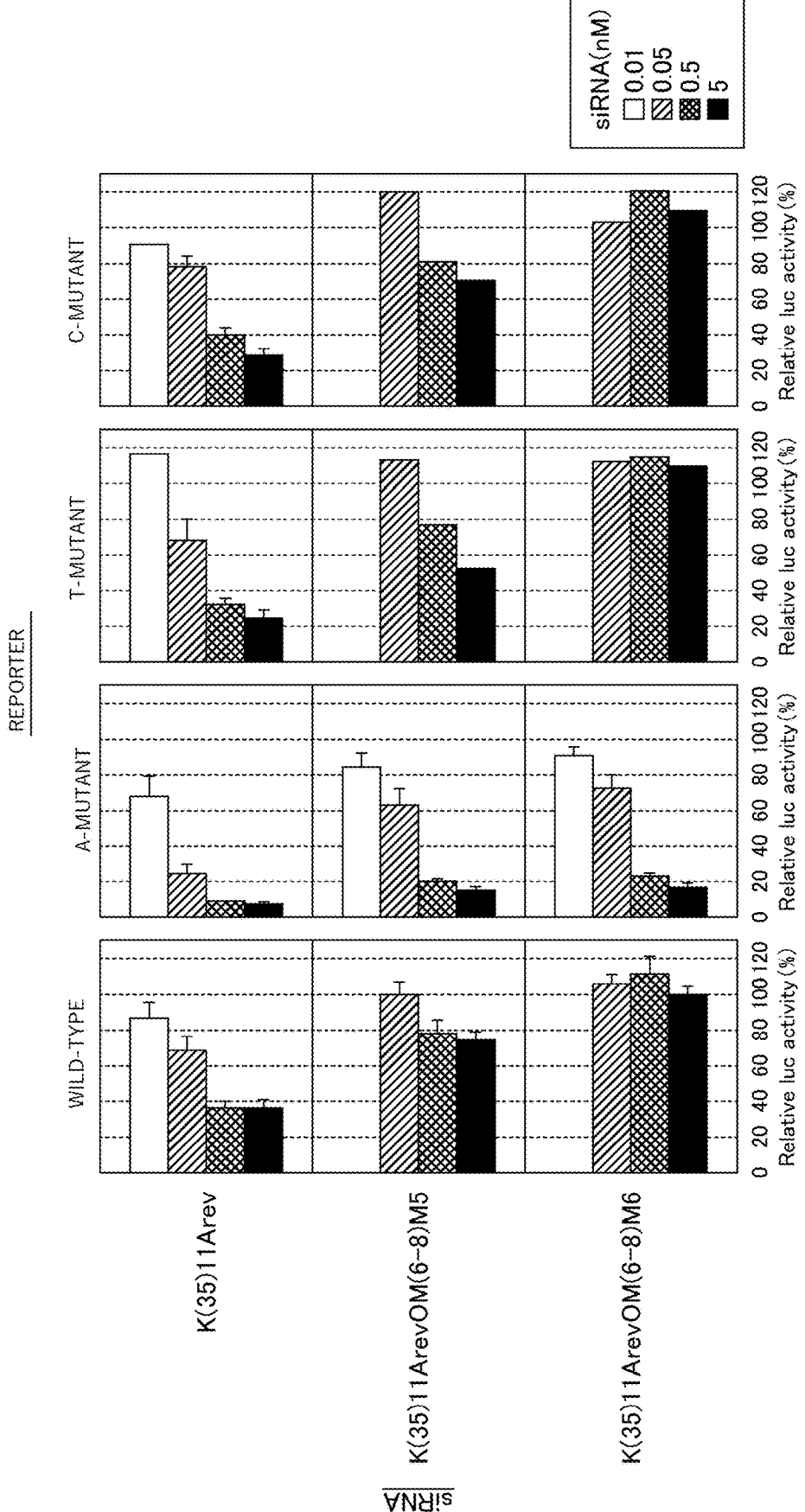
FIG. 6 shows graphs of results for silencing abilities of siRNAs specific for the A-mutant allele of K-ms gene, to the wild-type allele, the T-mutant K-ms (c. 35G>T) allele, and the C-mutant K-ms (c. 35 G>C) allele, in one example of the present invention.

FIG. 6 shows gene silencing effects on each reporter.

All siRNAs had the strongest silencing effect on the A-mutant K reporter; especially K(35)11ArevOM(6-8)M5 and K(35)11ArevOM(6-8)M6 had weak silencing effects on the T-mutant and C-mutant K reporters.

Example 1A-7

This example shows that siRNAs specific for the T-mutant allele exhibit weak silencing abilities not only to the wild-type allele, but also the A-mutant and C-mutant alleles.

The wild-type reporter, the A-mutant K reporter, the T-mutant K reporter, and the C-mutant K reporter, which are all K-ms reporters, were used as reporters for examining gene silencing effects. K(35)11TrevOM(6-8)M5 and K(35) 11TrevOM(6-8)M6 were used as siRNAs, and K(35)11Trev was used as a control. In the following sequences, the base pairs corresponding to the position of the point mutation, the pairs of the replaced bases at the 5'-ends of the guide and passenger strands, and the base pairs with the mismatched base are enclosed in rectangles. The nucleotides in which the group at 2'-position of the pentose was replaced by OCH₃ are hatched.

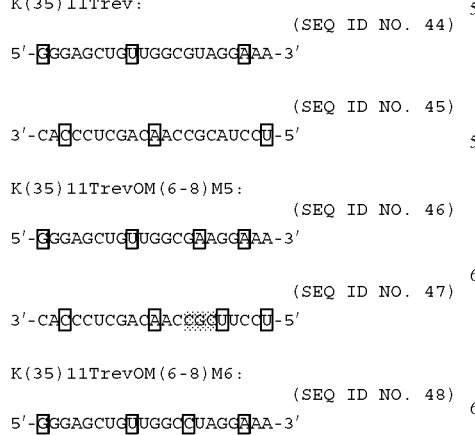

```
K(35)11Trev:
                                    (SEQ ID NO. 44)
5'-ΔGGGAGCUGΔUGGCGUAGGΔAA-3'

(SEQ ID NO. 45)
3'-CAΔCCUCGACΔACCGCAUCCΔU-5'

K(35)11TrevOM(6-8)M5:
                                    (SEQ ID NO. 46)
5'-ΔGGGAGCUGΔUGGCGΔAGGΔAA-3'

(SEQ ID NO. 47)
3'-CAΔCCUCGACΔACCΔCΔUCCΔU-5'

K(35)11TrevOM(6-8)M6:
                                    (SEQ ID NO. 48)
5'-ΔGGGAGCUGΔUGGCΔUAGGΔAA-3'
```

---

```
                                    (SEQ ID NO. 49)
3'-CAΔCCUCGACΔACΔCΔAUCCΔU-5'
```

Figure 7:
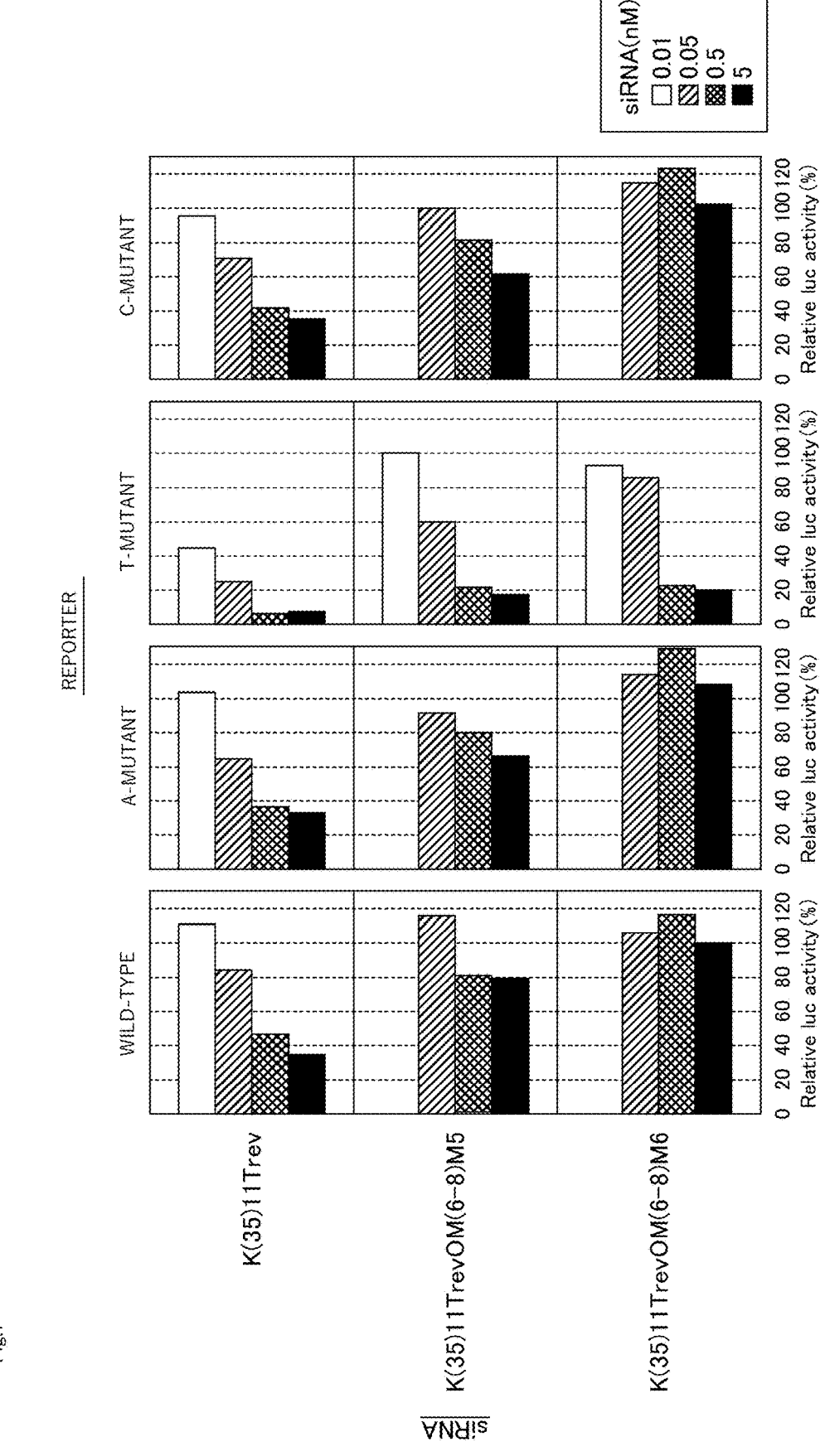
FIG. 7 shows graphs of results for silencing abilities of siRNAs specific for a T-mutant allele of K-ms gene, to the wild-type allele, and the A- and C-mutant K-ms alleles, in one example of the present invention.

FIG. 7 shows gene silencing effects on each reporter.

All siRNAs had the strongest silencing effect on the T-mutant K reporter; especially K(35)11TrevOM(6-8)M5 and K(35)11TrevOM(6-8)M6 had weak silencing effects on the T-mutant and C-mutant K reporters.

Example 1A-8

This example shows that siRNAs specific for the C-mutant allele exhibit weak silencing abilities not only to the wild-type allele, but also the A-mutant and T-mutant alleles.

The wild-type reporter, the A-mutant K reporter, the T-mutant K reporter, and the C-mutant K reporter, which are all K-ms reporters were used as reporters for examining gene silencing effects. K(35)11CrevOM(6-8)M5 and K(35) 11CrevOM(6-8)M6 were used as siRNAs, and K(35)11Crev was used as a control. In the following sequences, the base pairs corresponding to the position of the point mutation, the pairs of the replaced bases at the 5'-ends of the guide and passenger strands, and the base pairs with the mismatched base are enclosed in rectangles. The nucleotides in which the group at the 2'-position of the pentose was replaced by OCH₃ are hatched.

```
K(35)11Crev:
                                    (SEQ ID NO. 50)
5'-ΔGGGAGCUGΔUGGCGUAGGΔAA-3'

(SEQ ID NO. 51)
3'-CAΔCCUCGACΔACCGCAUCCΔU-5'

K(35)11CrevOM(6-8)M5:
                                    (SEQ ID NO. 52)
5'-ΔGGGAGCUGΔUGGCGΔAGGΔAA-3'

(SEQ ID NO. 53)
3'-CAΔCCUCGACΔACΔCΔUCCΔU-5'

K(35)11CrevOM(6-8)M6:
                                    (SEQ ID NO. 54)
5'-ΔGGGAGCUGΔUGGCΔUAGGΔAA-3'

(SEQ ID NO. 55)
3'-CAΔCCUCGACΔACΔCΔAUCCΔU-5'
```

Figure 8:
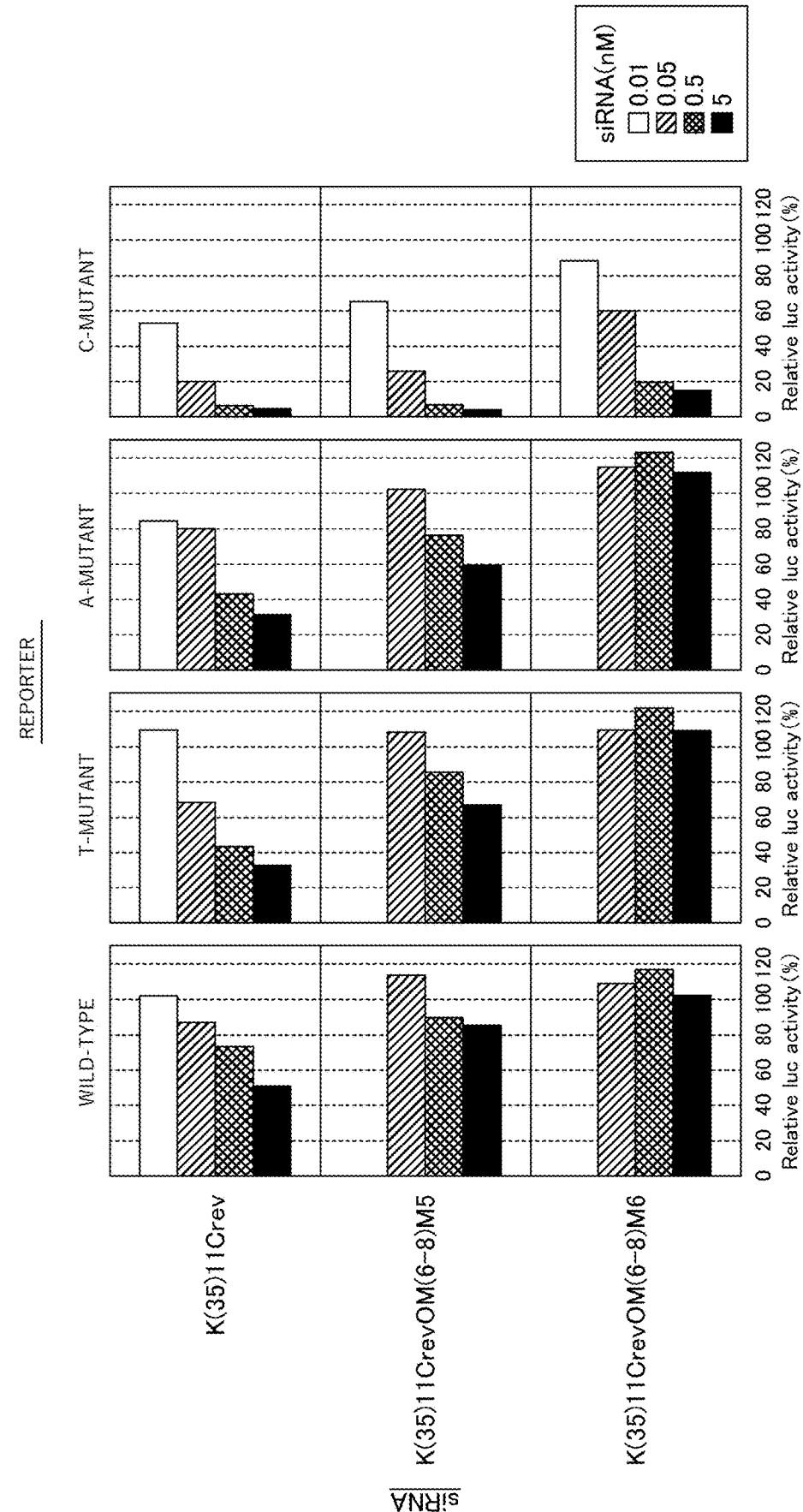
FIG. 8 shows graphs of results for silencing abilities of siRNAs specific for a C-mutant allele of K-ms gene, to the wild-type allele, and the A- and T-mutant K-ms alleles, in one example of the present invention.

FIG. 8 shows gene silencing effects on each reporter.

All siRNAs had the strongest silencing effect on the C-mutant K reporter; especially K(35)11CrevOM(6-8) M5 and K(35)11CrevOM(6-8)M6 had weak silencing effect on the A-mutant and T-mutant K reporters.

Example 1B

In this example, the N-ms gene was chosen as a target to be silenced.

Example 1B-1

This example in which a point mutation in nt 35 of cDNA of the N-ms gene is targeted shows that by matching position 11 of an siRNA with the position of the point mutation in the A-mutant N-ms (c. 35G>A) allele (hereinafter, referred to as the "A-mutant N35 allele"), replacing the base at the 5'-end of the guide strand of the siRNA from cytosine to uracil, replacing the base at the 5'-end of the passenger strand thereof from adenine to guanine, replacing the group at the 2'-position of a pentose in each of ribonucleotides at positions 6-8 of the guide strand by OCH₃, and mismatching the base at position 5 of the guide strand of the siRNA with the base of the A-mutant N35 allele, the siRNA suppresses the expression of the A-mutant N35 allele more specifically than that of the wild-type N-ras (wt) allele (hereinafter, referred to as the "wild-type N allele").

First, as reporters for examining gene silencing effects, DNAs having the same nucleotide sequences as the wild-type N allele and the A-mutant N35 allele were inserted into the 3'-UTR of the luciferase gene in an expression vector (psiCHECK) to construct wild-type N35 and A-mutant N reporters, respectively. The sequences of the segments chemically synthesized and incorporated into the vectors are indicated below. In the following sequences, the base pairs in the location corresponding to the position of the point mutation are enclosed in rectangles.

Wild-type N35 reporter:
(SEQ ID NO. 56)
5'-ACTGGTGGTGGTTGGAGCAG[G]TGGTGTTGGGAAAAGCGCA-3'

(SEQ ID NO. 57)
3'-TGACCACCACCAACCTCGAC[C]ACCACAACCCTTTTCGCGT-5'

A-mutant N35 reporter:
(SEQ ID NO. 58)
5'-ACTGGTGGTGGTTGGAGCAG[A]TGGTGTTGGGAAAAGCGCA-3'

(SEQ ID NO. 59)
3'-TGACCACCACCAACCTCGAC[T]ACCACAACCCTTTTCGCGT-5'

Double-stranded RNAs with the following sequence were chemically synthesized as siRNAs. N(35)11G has a sequence complementary to that of the wild-type N allele. N(35)11A is an siRNA in which position 11 corresponded to the position of the point mutation in the A-mutant N35 allele. N(35)11ArevOM(6-8)M5 is an siRNA in which position 11 corresponded to the position of the point mutation in the A-mutant N35 allele, the base at the 5'-end of the guide strand was replaced from cytosine to uracil, the base at the 5'-end of the passenger strand was replaced from uracil to cytosine, the group at the 2'-position of a pentose in each of ribonucleotides at positions 6-8 of the guide strand was replaced by OCH₃, and the base at position 5 of the guide strand is mismatched with the base of the A-mutant N35 allele. In the following sequences, the base pairs corresponding to the position of the point mutation, the base pairs of the replaced bases at the 5'-ends of the guide and passenger strands, and the base pair with the mismatched base are enclosed in rectangles. The nucleotides in which the group at the 2'-position of the pentose was replaced with OCH₃ are hatched.

N(35)11G:
(SEQ ID NO. 60)
5'-UGGAGCAG[G]UGGUGUUGGGAA-3'

-continued
(SEQ ID NO. 61)
3'-CAACCUCGUC[C]ACCACAACCC-5'

N(35)11A:
(SEQ ID NO. 62)
5'-UGGAGCAG[A]UGGUGUUGGGAA-3'

(SEQ ID NO. 63)
3'-CAACCUCGUC[U]ACCACAACCC-5'

N(35)11ArevOM(6-8)M5:
(SEQ ID NO. 64)
5'-[C]GGAGCAG[A]UGGUC[A]UGG[A]AA-3'

(SEQ ID NO. 65)
3'-CA[G]CCUCGUC[U]ACCAC[U]ACC[U]-5'

Figure 9:
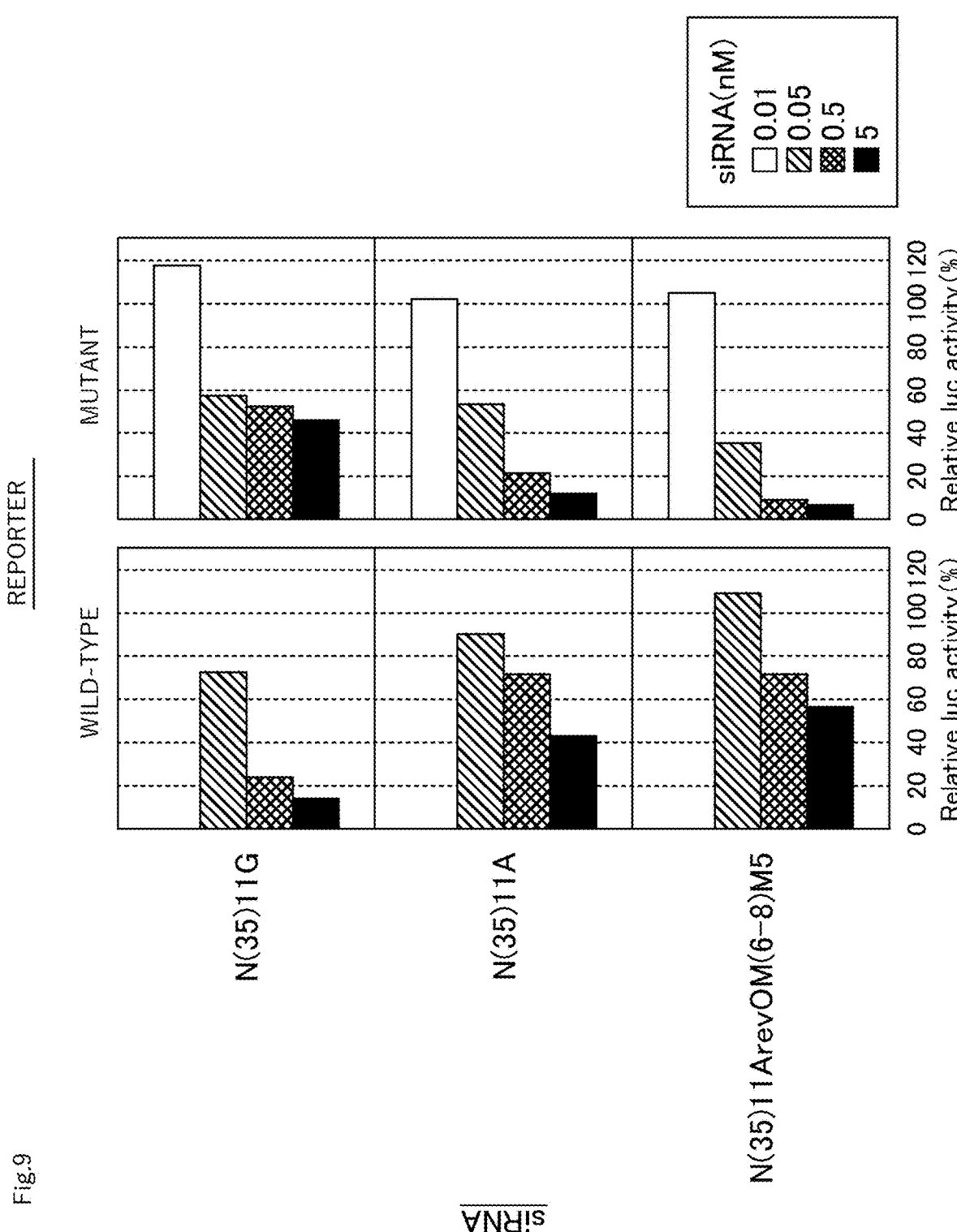
FIG. 9 shows graphs of results for silencing abilities of an siRNA, which targeted the point mutation in nt 35 of cDNA of an N-ms gene, and in which position 11 corresponded to the position of the point mutation in the A-mutant N-ms (c. 35G>A) allele (hereinafter, referred to as "A-mutant N35 allele"), the base at the 5'-end of the guide strand was replaced from cytosine to uracil, the base at the 5'-end of the passenger strand was replaced from adenine to guanine, the group at the 2'-position of a pentose in each of ribonucle-otides at positions 6-8 of the guide strand was replaced by $OCH_3$, and the base at position 5 of the guide strand was mismatched with that of the A-mutant N35 allele, in one example of the present invention.

FIG. 9 shows gene silencing effects of each siRNA.

N(35)11G effectively suppressed the expression of the wild-type N allele more than that of the A-mutant N35 allele. In contrast, N(35)11A effectively suppressed the expression of the A-mutant N35 allele more than that of the wild-type N allele. N(35)11ArevOM(6-8)M5 had very weak silencing abilities to the wild-type allele and strong silencing abilities to the A-mutant N35 allele; as a result, specificity for the A-mutant N35 allele was increased.

Example 1B-2

This example in which the point mutation in nt 182 of cDNA of the N-ms gene is targeted shows that, by matching position 11 in an siRNA with the position of the point mutation in an A-mutant N-ms (c. 182A>G) allele (hereinafter, referred to as a "G-mutant N182 allele"), replacing the base at the 5'-end of the guide strand of the siRNA from guanine to uracil, replacing the base at the 5'-end of the passenger strand thereof from adenine to guanine, replacing the group at the 2'-position of a pentose in each of ribonucleotides at positions 6-8 of the guide strand with OCH₃, and by mismatching the base at position 5 of the guide strand of the siRNA with the base of the G-mutant N182 allele, the siRNA suppresses the expression of the G-mutant N182 allele more specifically than that of the wild-type N-ms (wt) allele (hereinafter, referred to as the "wild-type N allele").

First, as reporters for examining gene silencing effects, DNA having the same nucleotide sequence as the G-mutant N182 allele was inserted into the 3'-UTR of the luciferase gene in an expression vector (psiCHECK) to construct a G-mutant N182 reporter. The sequences of the segments chemically synthesized and incorporated into the vector are indicated below.

Wild-type N182 reporter:
(SEQ ID NO. 66)
5'-CATACTGGATACAGCTGGAC[A]AGAAGAGTACAGTGCCA-3'

(SEQ ID NO. 67)
3'-GTATGACCTATGTCGACCTG[T]TCTTCTCATGTCACGGT-5'

G-mutant N182 reporter:
(SEQ ID NO. 68)
5'-CATACTGGATACAGCTGGAC[G]AGAAGAGTACAGTGCCA-3'

-continued (SEQ ID NO. 69)
```
3'-GTATGACCTATGTCGACCTG C TCTTCTCATGTCACGGT-5'
```

Double-stranded RNA with the following sequence were chemically synthesized as siRNAs. N(182)11A has a sequence complementary to that of the wild-type N allele. N(182)11G is an siRNA whose position 11 was matched with the position of the point mutation in the G-mutant N182 allele. N(182)11GrevOM(6-8)M5 is an siRNA whose position 11 was matched with the position of the point mutation in the A182-mutant N allele, and in which the base at the 5'-end of the guide strand was replaced from guanine to uracil, the base at the 5'-end of the passenger strand was replaced from adenine to guanine, the group at the 2'-position of a pentose in each of ribonucleotides at positions 6-8 of the guide strand was replaced with $OCH_3$, and a base at position 5 of the guide strand is mismatched with that of the G-mutant 182N allele. In the following sequences, the base pairs of the position of the point mutation, the base pairs of the replaced bases at the 5'-ends of the guide and passenger strands, and a base pair with the mismatched base are enclosed in rectangles. The nucleotides in which the group at the 2'-position of the pentose was replaced by $OCH_3$ are hatched.

```
N(182)11A:
                              (SEQ ID NO. 70)
5'-AGCUGGAC A AGAAGAGUACAG-3'

(SEQ ID NO. 71)
3'-UGUCGACCUG U UCUUCUCAUG-5'

N(182)11G:
                              (SEQ ID NO. 72)
5'-AGCUGGAC G AGAAGAGUACAG-3'

(SEQ ID NO. 73)
3'-UGUCGACCUG C UCUUCUCAUG-5'

N(182)11GrevOM(6-8)M5:
                              (SEQ ID NO. 74)
5'- G GCUGGAC G AGAAG U GUA A AG-3'

(SEQ ID NO. 75)
3'-UG C CGACCUG C UC UUC A CAU U -5'
```

Figure 10:
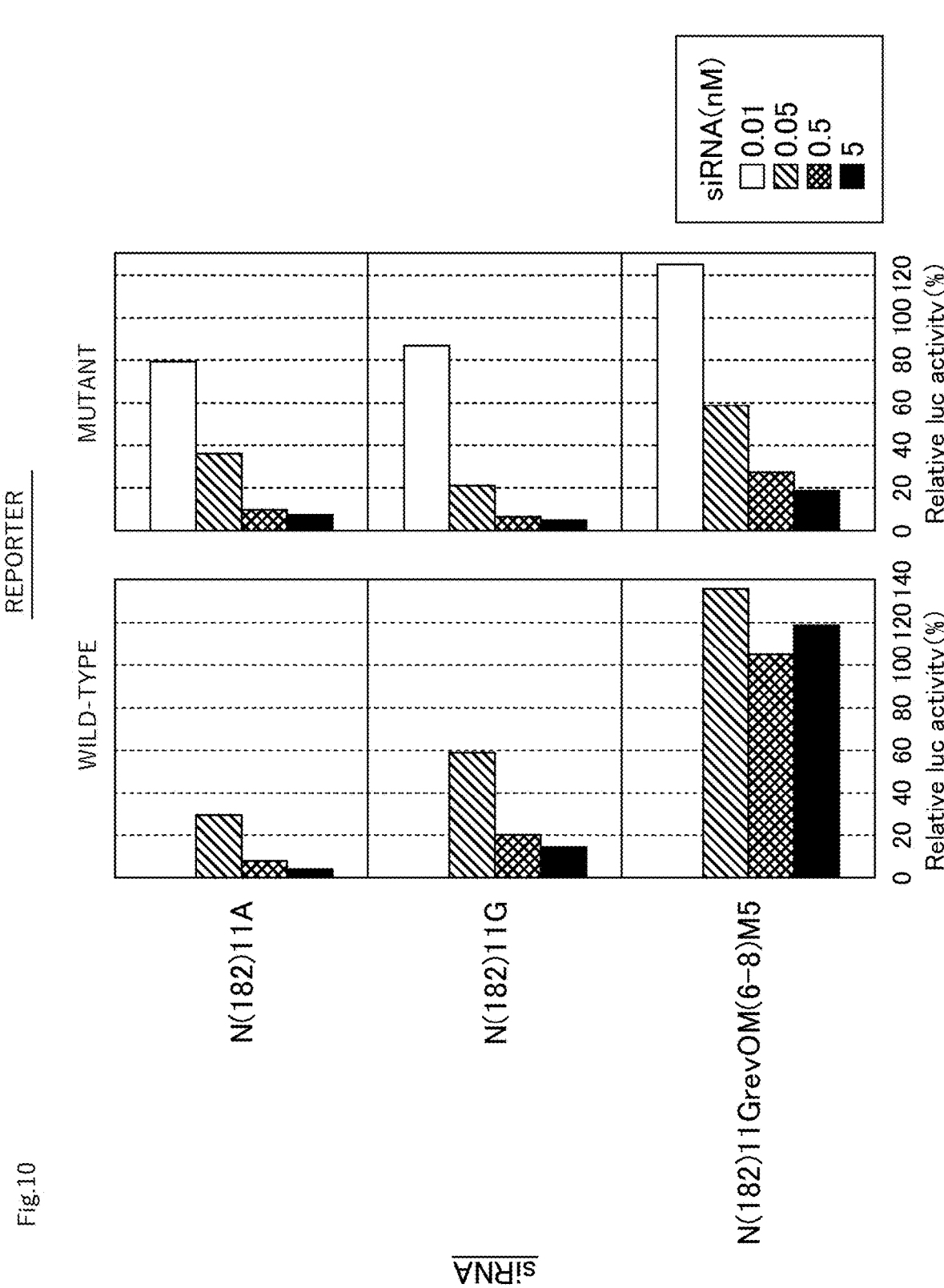
FIG. 10 shows graphs of results for silencing abilities of an siRNA, which targeted the point mutation in nt 182 of cDNA of the N-ms gene, and in which position 11 corresponded to a position of the point mutation in the A-mutant N-ms (c. 182A>G) allele (hereinafter, referred to as a "G-mutant N182 allele"), the base at the 5'-end of the guide strand was replaced from guanine to uracil, the base at the 5'-end of the passenger strand was replaced from adenine to guanine, the group at the 2'-position of a pentose in each of ribonucleotides at positions 6-8 of the guide strand was replaced by $OCH_3$, and the base at position 5 of the guide strand is mismatched with that of the G-mutant N182 allele, in one example of the present invention.
Figure 11A:
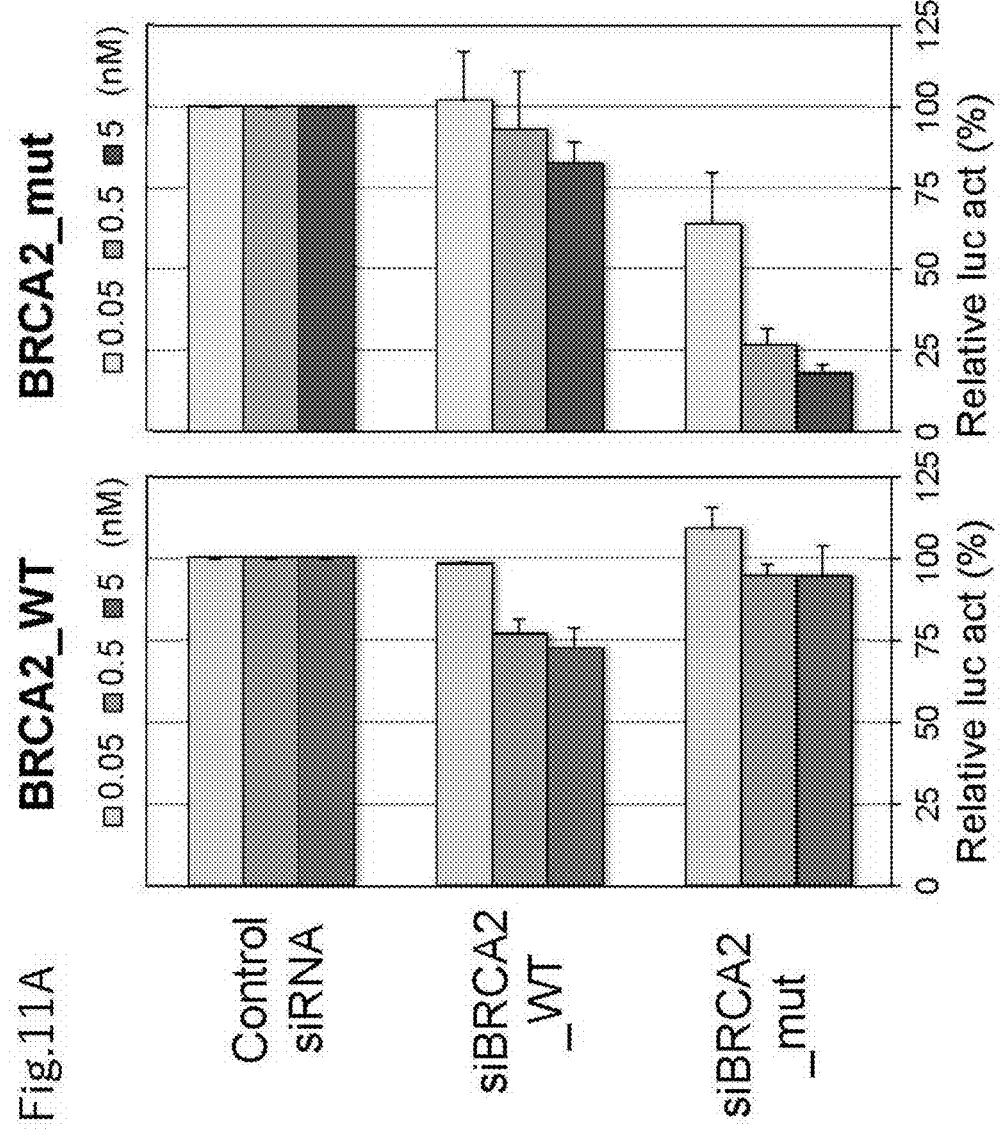
FIG. 11A shows graphs of the results indicating that the siRNA with the sequence of the present disclosure hardly suppresses the expression of the wild-type allele but strongly suppress the expression of the mutant allele, when the wild-type and A1114C mutant alleles of a BRCA2 gene are used in one example of the present invention.
Figure 11B:
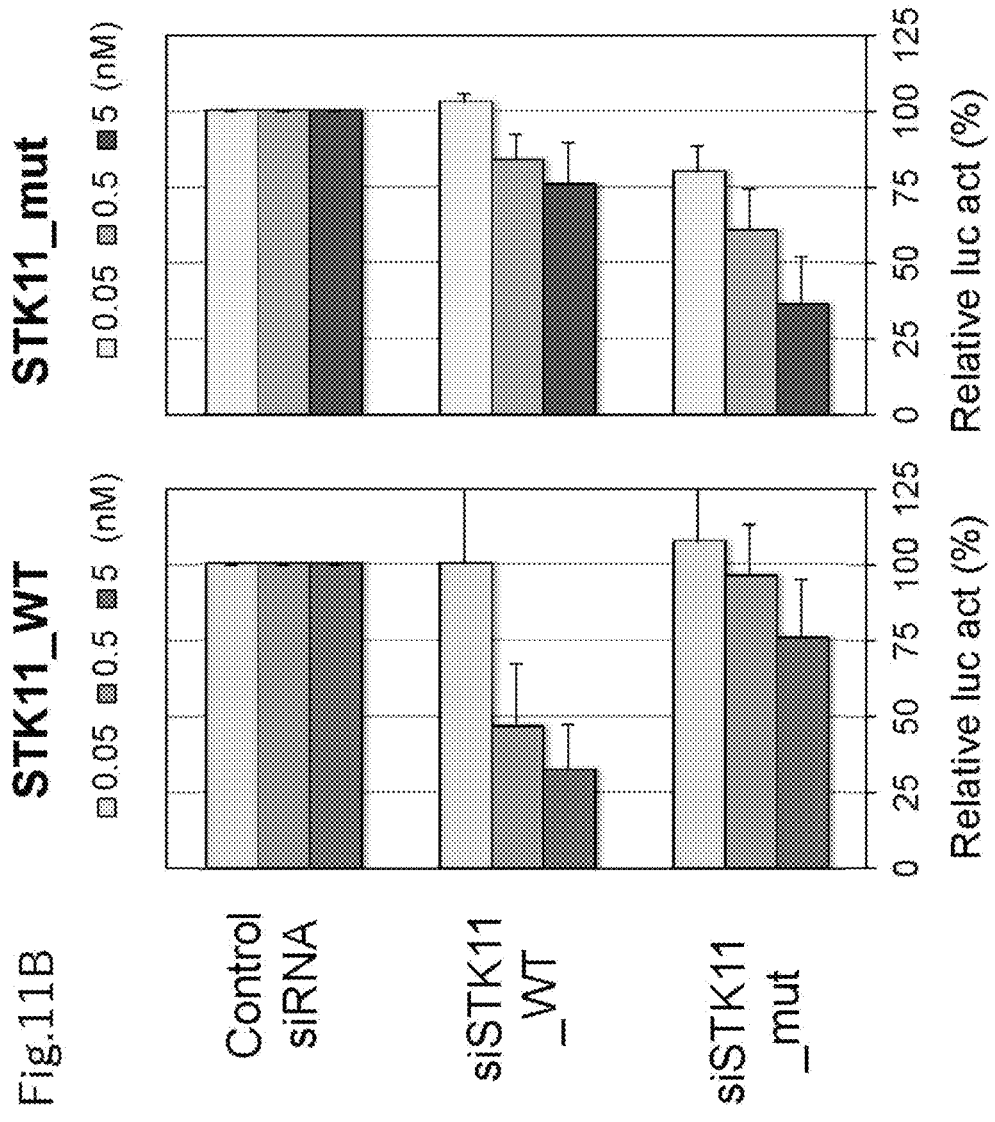
FIG. 11B shows graphs of the results indicating that the siRNA with the sequence of the present disclosure hardly suppresses the expression of the wild-type allele but strongly suppress the expression of the mutant allele, when the wild-type and C1062G mutant alleles of an STK11 gene are used.
Figure 11C:
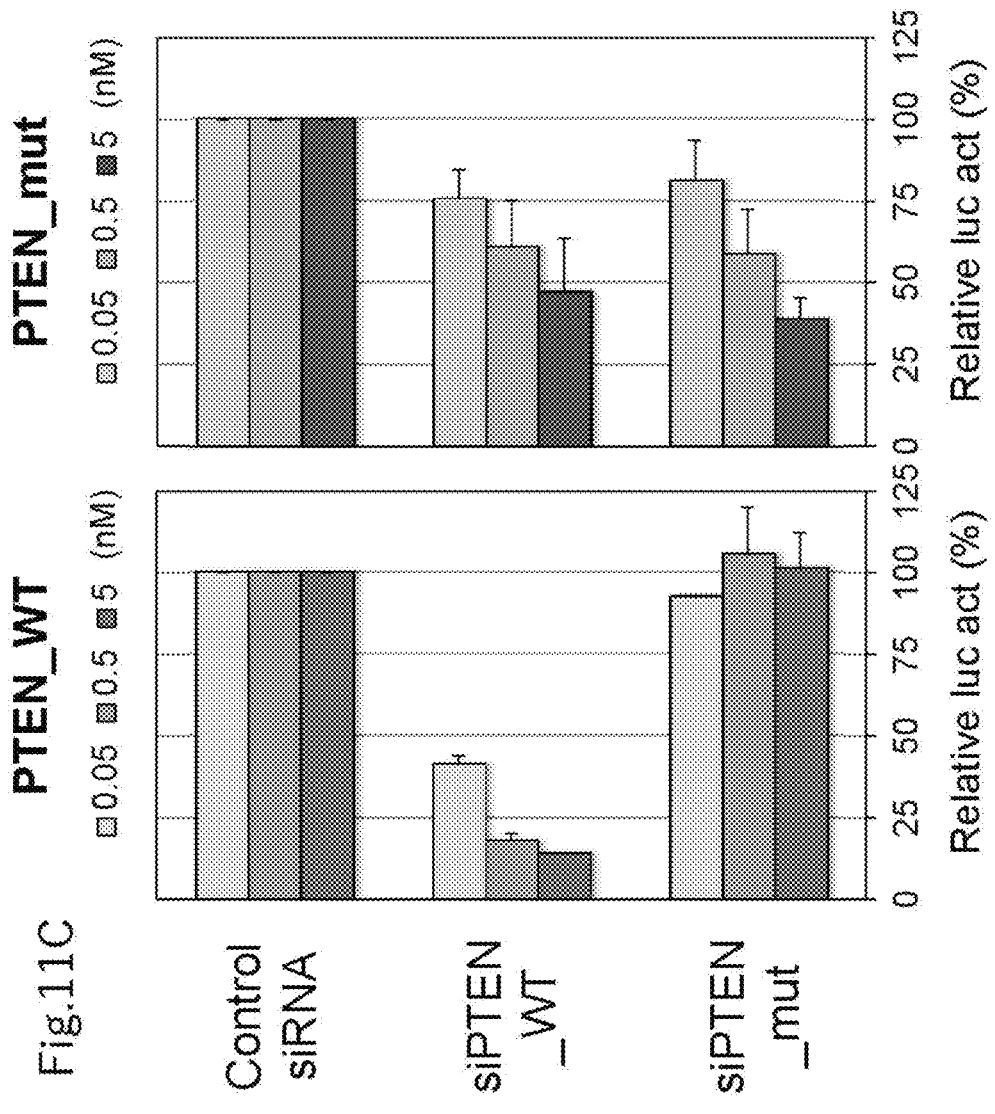
FIG. 11C shows graphs of the results indicating that the siRNA with the sequence of the present disclosure hardly suppresses the expression of the wild-type allele but strongly suppress the expression of the mutant allele, when the wild-type and C388G mutant alleles of a PTEN gene are used.
Figure 11D:
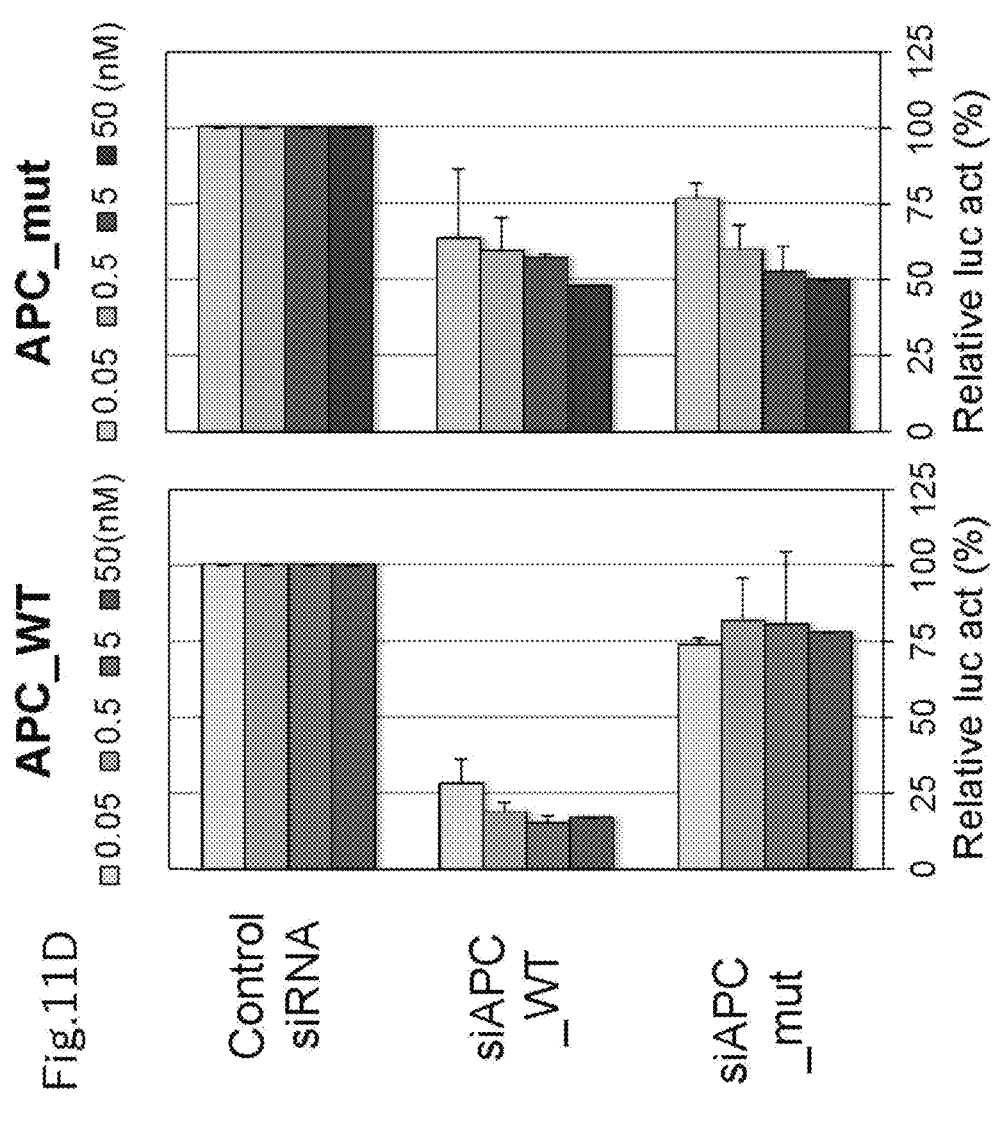
FIG. 11D shows graphs of the results indicating that the siRNA with the sequence of the present disclosure hardly suppresses the expression of the wild-type allele but strongly suppress the expression of the mutant allele, when the wild-type and C4348T mutant alleles of an APC gene are used.
Figure 11E:
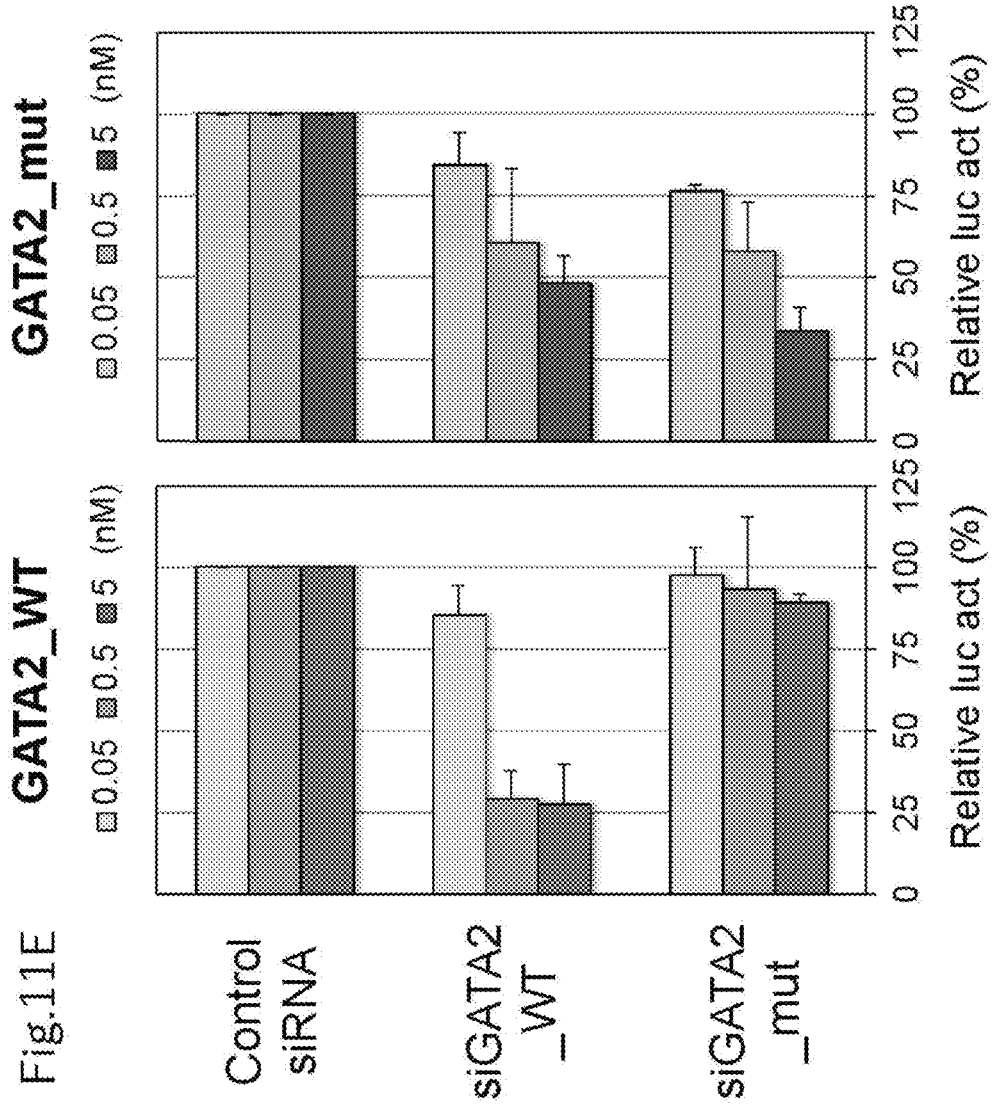
FIG. 11E shows graphs of the results indicating that the siRNA with the sequence of the present disclosure hardly suppresses the expression of the wild-type allele but strongly suppress the expression of the mutant allele, when the wild-type and C953T mutant alleles of a GATA2 gene are used.
Figure 11F:
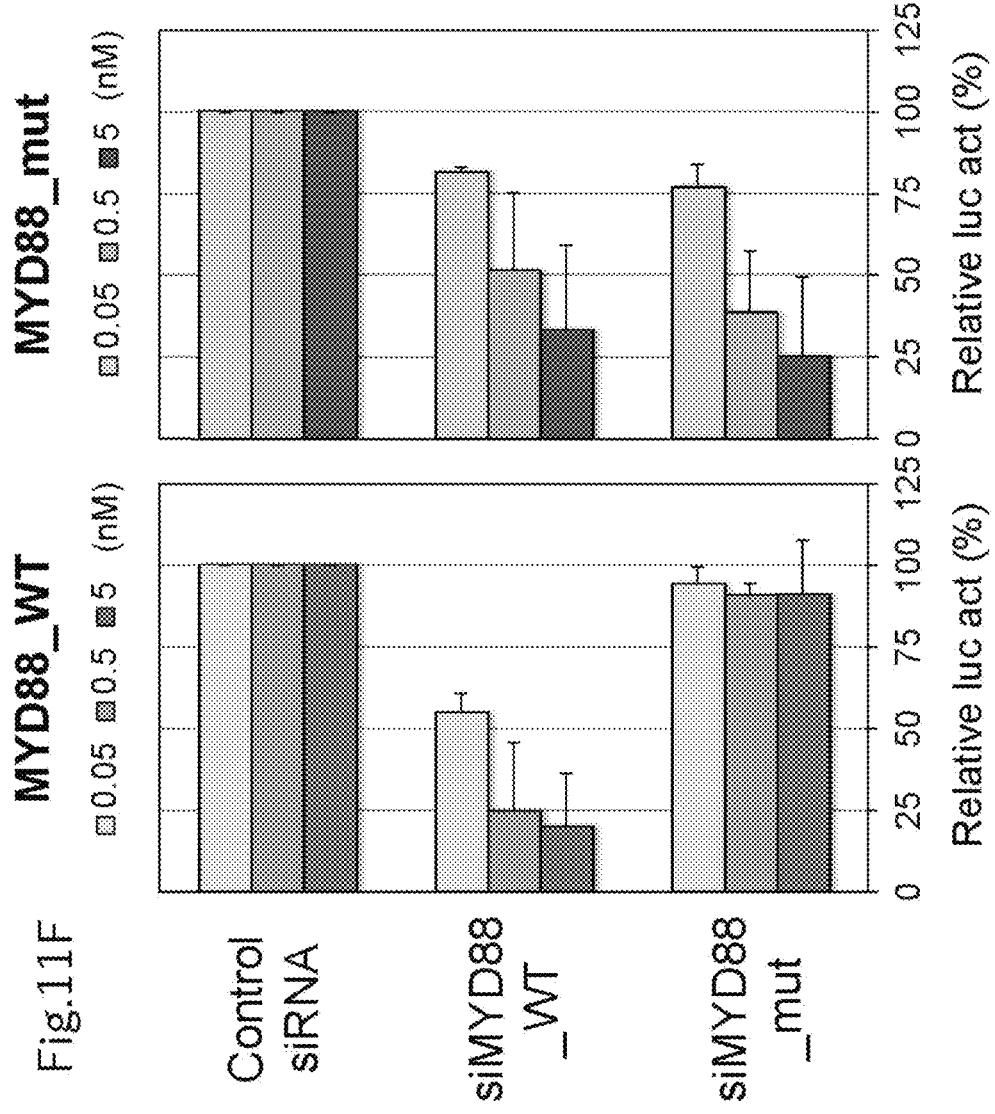
FIG. 11F shows graphs of the results indicating that the siRNA with the sequence of the present disclosure hardly suppresses the expression of the wild-type allele but strongly suppress the expression of the mutant allele, when the wild-type and T818C mutant alleles of an MYD88 gene are used.
Figure 11G:
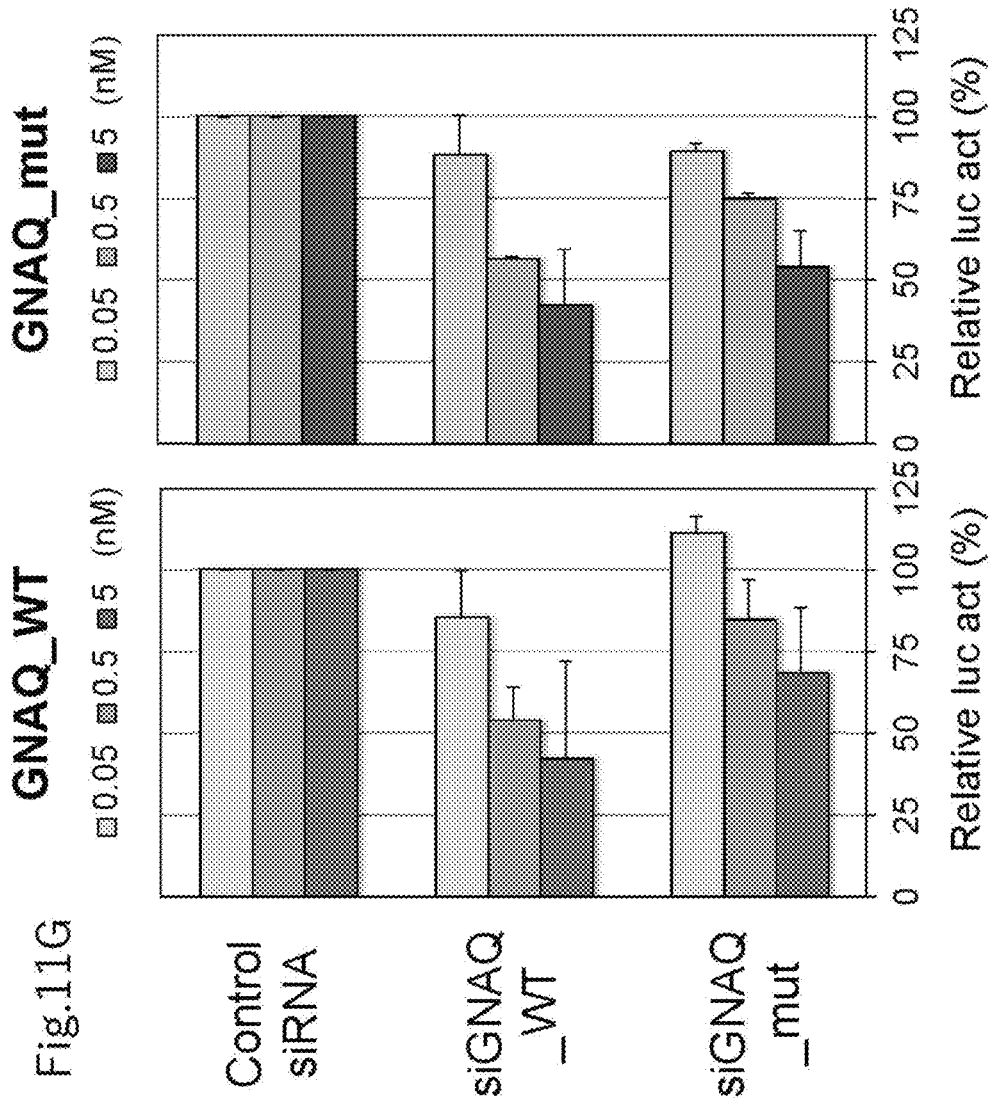
FIG. 11G shows graphs of the results indicating that the siRNA with the sequence of the present disclosure hardly suppresses the expression of the wild-type allele but strongly suppress the expression of the mutant allele, when the wild-type and A626T mutant alleles of a GNAQ gene are used.
Figure 11H:
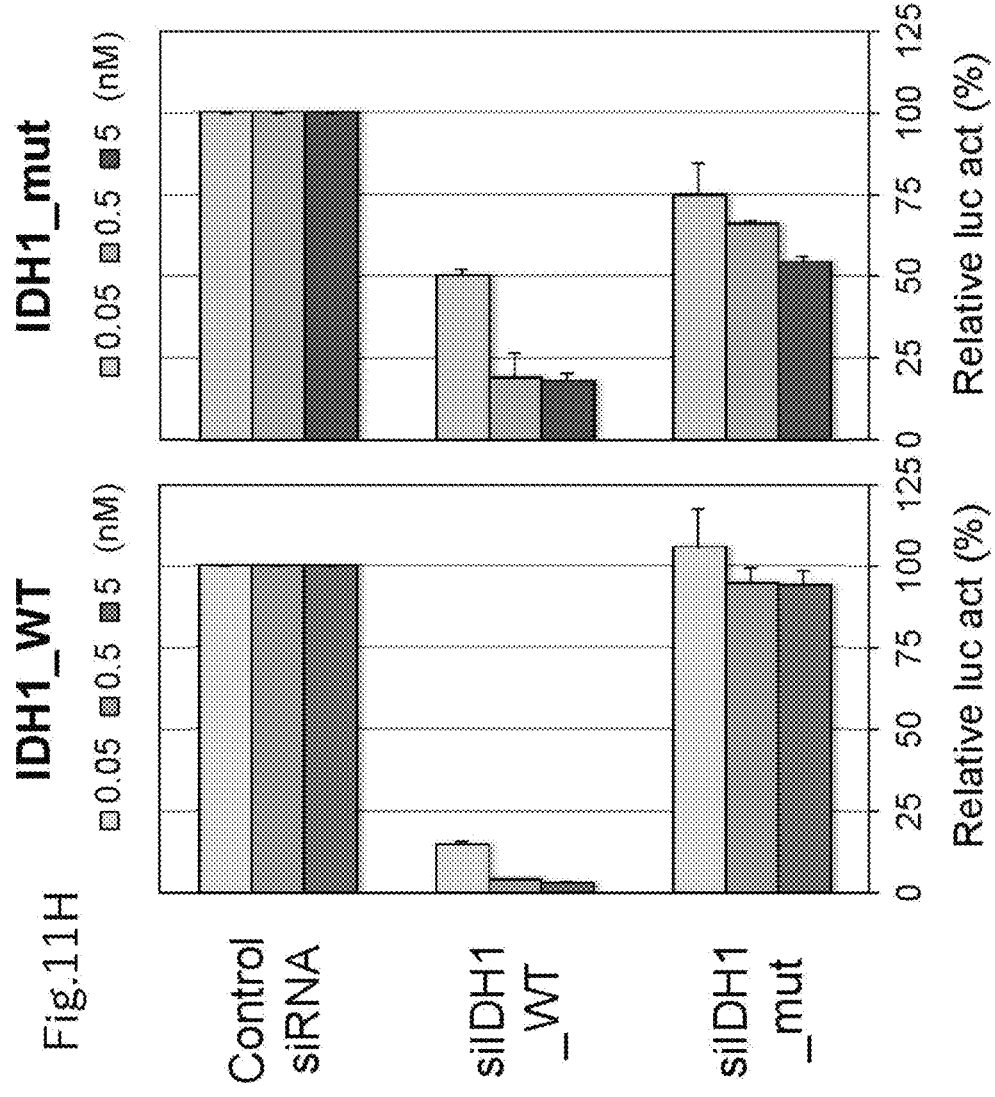
FIG. 11H shows graphs of the results indicating that the siRNA with the sequence of the present disclosure hardly suppresses the expression of the wild-type allele but strongly suppress the expression of the mutant allele, when the wild-type and G395A mutant alleles of an IDH1 gene are used.

FIG. 10 shows gene silencing effects of each siRNA.

N(182)11A more effectively suppressed the expression of the wild-type N182 allele than that of the G-mutant N182 allele. In contrast, N(182)11G more effectively suppressed the expression of the A-mutant N182 allele than that of the wild-type N182 allele. N(182)11ArevOM(6-8)M5 lost silencing abilities to the wild-type allele and exhibited slightly reduced silencing abilities to the G-mutant N182 allele, resulting in an higher specificity for the G-mutant N182 allele.

Example 1C

This example shows that siRNAs with sequences of the present disclosure hardly suppress the expression of the expression of a wild-type allele but strongly suppress the expression of a mutant allele to pairs of: the wild-type allele and the A1114C mutant allele (with a mutation from A to C at position 1114 in cDNA (GENE ID: 675)) of the BRCA2 gene, the wild-type allele and the C1062G mutant allele (with a mutation from C to G at position 1062 in cDNA (GENE ID: 6794)) of the STK11 gene, the wild-type allele and the C388G mutant allele (with a mutation from C to G at position 388 in cDNA (GENE ID: 5728)) of the PTEN gene, the wild-type allele and the C4348T mutant allele (with a mutation from C to T at position 4348 in cDNA (GENE ID: 324)) of the APC gene, the wild-type allele and the C953T mutant allele (with a mutation from C to T at position 953 in cDNA (GENE ID: 2624)) of the GATA2 gene, the wild-type allele and the T818C mutant allele (with a mutation from T to C at position 818 in cDNA (GENE ID: 4615)) of the MYD88 gene, the wild-type allele and the A626T mutant allele (with a mutation from A to T at position 626 in cDNA (GENE ID: 2776)) of the GNAQ gene, the wild-type allele and the G395A mutant allele (with a mutation from G to A at position 395 in cDNA (GENE ID: 3417)) of the IDH1 gene.

First, as reporters for examining gene silencing effects, DNAs having the same nucleotide sequence as the respective alleles were chemically synthesized and inserted into the 3'-UTR of the luciferase gene in an expression vector (psiCHECK) to construct wild-type and A-mutant K reporters. The sequences of the segments incorporated into the vectors are indicated below.

```
BRCA2_wt reporter:
                                        (SEQ ID NO. 76)
5'-CATTAGATTCAAATGTAGCA A ATCAGAAGCCCTTTGAGAGT-3'

(SEQ ID NO. 77)
3'-GTAATCTAAGTTTACATCGT T TAGTCTTCGGGAAACTCTCA-5'

BRCA2_mut reporter:
                                        (SEQ ID NO. 78)
5'-CATTAGATTCAAATGTAGCA C ATCAGAAGCCCTTTGAGAGT-3'

(SEQ ID NO. 79)
3'-GTAATCTAAGTTTACATCGT G TAGTCTTCGGGAAACTCTCA-5'

STK11_wt reporter:
                                        (SEQ ID NO. 80)
5'-GACGAGGACGAGGACCTCTT C GACATCGAGGATGACATCAT-3'

(SEQ ID NO. 81)
3'-CTGCTCCTGCTCCTGGAGAA G CTGTAGCTCCTACTGTAGTA-5'

STK11_mut reporter:
                                        (SEQ ID NO. 82)
5'-GACGAGGACGAGGACCTCTT G GACATCGAGGATGACATCAT-3'

(SEQ ID NO. 83)
3'-CTGCTCCTGCTCCTGGAGAA C CTGTAGCTCCTACTGTAGTA-5'

PTEN_wt reporter:
                                        (SEQ ID NO. 84)
5'-ACTGTAAAGCTGGAAAGGGA C GAACTGGTGTAATGATATGT-3'

(SEQ ID NO. 85)
3'-TGACATTTCGACCTTTCCCT G CTTGACCACATTACTATACA-5'
```

-continued

PTEN_mut reporter:

(SEQ ID NO. 86)

5'-ACTGTAAAGCTGGAAAGGGAGGAACTGGTGTAATGATATGT-3'

(SEQ ID NO. 87)

3'-TGACATTTCGACCTTTCCCTCCTTGACCACATTACTATACA-5'

APC_wt reporter:

(SEQ ID NO. 88)

5'-CTCAAACAGCTCAAACCAAGCGAGAAGTACCTAAAAATAAA-3'

(SEQ ID NO. 89)

3'-GAGTTTGTCGAGTTTGGTTCGCTCTTCATGGATTTTTATTT-5'

APC_mut reporter:

(SEQ ID NO. 90)

5'-CTCAAACAGCTCAAACCAAGTGAGAAGTACCTAAAAATAAA-3'

(SEQ ID NO. 91)

3'-GAGTTTGTCGAGTTTGGTTCACTCTTCATGGATTTTTATTT-5'

GATA2_wt reporter:

(SEQ ID NO. 92)

5'-CGGCCACTACCTGTGCAATGCCTGTGGCCTCTACCACAAGA-3'

(SEQ ID NO. 93)

3'-GCCGGTGATGGACACGTTACGGACACCGGAGATGGTGTTCT-5'

GATA2_mut reporter:

(SEQ ID NO. 94)

5'-CGGCCACTACCTGTGCAATGTCTGTGGCCTCTACCACAAGA-3'

(SEQ ID NO. 95)

3'-GCCGGTGATGGACACGTTACAGACACCGGAGATGGTGTTCT-5'

MYD88_wt reporter:

(SEQ ID NO. 96)

5'-AGGTGCCCATCAGAAGCGACTGATCCCCATCAAGTACAAGG-3'

(SEQ ID NO. 97)

3'-TCCACGGGTAGTCTTCGCTGACTAGGGGTAGTTCATGTTCC-5'

MYD88_mut reporter:

(SEQ ID NO. 98)

5'-AGGTGCCCATCAGAAGCGACGGATCCCCATCAAGTACAAGG-3'

(SEQ ID NO. 99)

3'-TCCACGGGTAGTCTTCGCTGCCTAGGGGTAGTTCATGTTCC-5'

GNAQ_wt reporter:

(SEQ ID NO. 100)

5'-AATGGTCGATGTAGGGGGCCAAAGGTCAGAGAGAAGAAAAT-3'

(SEQ ID NO. 101)

3'-TTACCAGCTACATCCCCCGGTTTCCAGTCTCTCTTCTTTTA-5'

GNAQ_mut reporter:

(SEQ ID NO. 102)

5'-AATGGTCGATGTAGGGGGCCTAAGGTCAGAGAGAAGAAAAT-3'

(SEQ ID NO. 103)

3'-TTACCAGCTACATCCCCCGGATTCCAGTCTCTCTTCTTTTA-5'

-continued

IDH1_wt reporter:

(SEQ ID NO. 104)

5'-AAAACCTATCATCATAGGTCGTCATGCTTATGGGGATC-3'

(SEQ ID NO. 105)

3'-TTTTGGATAGTAGTATCCAGCAGTACGAATACCCCTAG-5'

IDH1_mut reporter:

(SEQ ID NO. 106)

5'-AAAACCTATCATCATAGGTCATCATGCTTATGGGGATC-3'

(SEQ ID NO. 107)

3'-TTTTGGATAGTAGTATCCAGTAGTACGAATACCCCTAG-5'

Next, double-stranded RNAs with the following sequences were chemically synthesized as siRNAs. These reporters and siRNAs were used to perform reporter assays in the same way as in Example 1A. The results are shown in FIG. 11. As a control siRNA, siBRCA2_wt was introduced and the measurements obtained for the double-stranded siRNAs were presented as graphs in FIG. 11, relative to those for siBRCA2_wt which were set to 100%.

In each of the following sequences, "wt" indicates an siRNA constructed based on the sequence of a wild-type gene. The base pairs corresponding to the position of the point mutation, the pairs of the replaced bases at the 5'-ends of the guide and passenger strands, and base pairs with a mismached base are enclosed in rectangles. The nucleotides in which the 2'-position of the pentose was replaced by $OCH_3$ are hatched.

siBRCA2_wt:

(SEQ ID NO. 108)

5'-AUGUAGCAAAUCAGAAGCCCU-3'

(SEQ ID NO. 109)

3'-UUUACAUCGUUUAGUCUUCGG-5' siBRCA2_mut:

(SEQ ID NO. 110)

5'-GUGUAGCACAUCACAAGCACU-3'

(SEQ ID NO. 111)

3'-UUCACAUCGUGUAGUGUUCGU-5' siSTK11_wt:

(SEQ ID NO. 112)

5'-GACCUCUUCGACAUCGAGGAU-3'

(SEQ ID NO. 113)

3'-UCCUGGAGAAGCUGUAGCUCC-5' siSTK11_mut:

(SEQ ID NO. 114)

5'-GACCUCUUGGACAACGAGAAU-3'

(SEQ ID NO. 115)

3'-UCCUGGAGAACCUGUUGCUCU-5' siPTEN_wt:

(SEQ ID NO. 116)

5'-GAAAGGGACGAACUGGUGUAA-3'

(SEQ ID NO. 117)

3'-ACCUUUCCCUGCUUGACCACA-5'

-continued siPTEN_mut:

(SEQ ID NO. 118)

5'-GAAAGGGA[G]GAAC[A]GGUC[A]AA-3'

(SEQ ID NO. 119)

3'-ACCUUUCCCU[C]CU[U][C][G]CCAC[U]-5' siAPC_wt:

(SEQ ID NO. 120)

5'-AAACCAAGCGAGAAGUACCUA-3'

(SEQ ID NO. 121)

3'-AGUUUGGUUCGCUCUUCAUGG-5' siAPC_mut:

(SEQ ID NO. 122)

5'-[G]AACCAA[C][U]GAGA[U]GUAC[A]UA-3'

(SEQ ID NO. 123)

3'-AG[G]UUGGUU[C]ACU[C][U][A]CAUG[U]-5' siGATA2_wt:

(SEQ ID NO. 124)

5'-GUGCAAUGCCUGUGGCCUCUA-3'

(SEQ ID NO. 125)

3'-GACACGUUACGGACACCGGAG-5' siGATA2_mut:

(SEQ ID NO. 126)

5'-GUGCAAU[G][U]CUGU[C]GCCU[A]UA-3'

(SEQ ID NO. 127)

3'-GACACGUUAC[A]GAC[A][C][G]CGGA[U]-5' siMYD88_wt:

(SEQ ID NO. 128)

5'-GAAGCGACUGAUCCCCAUCAA-3'

(SEQ ID NO. 129)

3'-GUCUUCGCUGACUAGGGGUAG-5' siMYD88_mut:

(SEQ ID NO. 130)

5'-GAAGCGAC[C]GAUC[G]CCAU[A]AA-3'

(SEQ ID NO. 131)

3'-GUCUUCGCUG[G]CUA[G][C][G]GGUA[U]-5' siGNAQ_wt:

(SEQ ID NO. 132)

5'-AGGGGGCCAAAGGUCAGAGAG-3'

(SEQ ID NO. 133)

3'-CAUCCCCCGGUUUCCAGUCUC-5' siGNAQ_mut:

(SEQ ID NO. 134)

5'-[G]GGGGGC[C][U]AAGG[A]CAGA[A]AG-3'

(SEQ ID NO. 135)

3'-CA[G]CCCCCGG[A]UU[C][C][U]GUCU[U]-5' siIDH1_wt:

(SEQ ID NO. 136)

5'-CAUAGGUCGUCAUGCUUAUGG-3'

(SEQ ID NO. 137)

3'-UAGUAUCCAGCAGUACGAAUA-5'

-continued siIDH1_mut:

(SEQ ID NO. 138)

5'-CAUAGGUC[A]UCAUG[G]UUAUGG-3'

(SEQ ID NO. 139)

3'-UAGUAUCCAG[U]AGUA[C][G][C]AAUA-5'

As is apparent from the graphs in FIG. 11, the siRNAs corresponding to the wild-type sequences suppress the expression of both wild-type and mutant alleles, whereas the siRNAs disclosed herein hardly suppress the expression of the wild-type alleles but strongly suppress the expression of the mutant alleles.

Example 2

This example shows that siRNAs that specifically suppress the expression of a mutant allele have similar specificities for the expression of endogenous genes in terms of the expression of exogenous reporters in culture cells.

Figure 12:
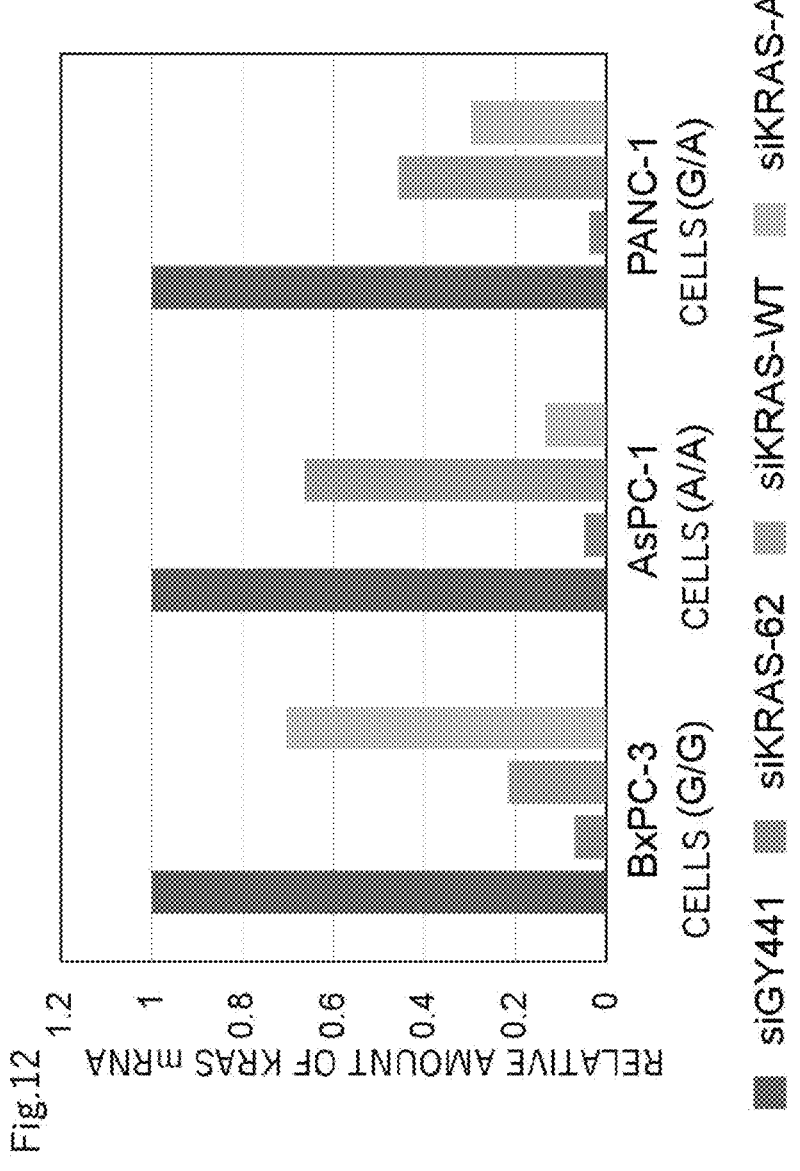
FIG. 12 shows a graph of the results indicating that siRNAs that suppress the expression of specific mutant alleles, when evaluated on the expression of exogenous reporters in culture cells, exhibit similar specificities for the expression of endogenous genes.

First, BxPC-3 (bases at position 35 are G/G: a wild-type homozygous), AsPC-1 (bases at position 35 are A/A: an A-mutant homozygous), and PANC-1 (bases at position 35 are G/A: A-mutant heterozygous), all of which were cell lines derived from pancreatic adenocarcinoma, were adherently cultured and using Lipofectamine RNAiMAX (Thermo Fisher Scientific), siGY441 (negative control), siKRAS-62 (positive control: siRNA that suppresses all K-ms mRNAs), siKRAS-WT (siRNA specific for the wild-type K-ras), or siKRAS-A (siRNA specific for the A-mutant: K(35)11ArevOM(6-8)M6) were transfected at a concentration of 50 nM, once a day for three consecutive days. On the day after the third transfection, mRNAs were isolated from a part of the cells and cDNAs were generated by reverse transcription. The K-ms mRNA was then quantified by a quantitative PCR. For each of the cells, the expression levels observed when the respective siRNAs were introduced were represented as relative values, with the expression level for siGY441 which is set to 100. The results are shown in FIG. 12.

The nucleotide sequences used in this example are indicated below. In the following sequences, "wt" indicates an siRNA constructed based on the sequence of a wild-type gene. The base pairs corresponding to the position of the point mutation, the base pairs of the replaced bases at the 5'-ends of the guide and passenger strands, and base pairs with a mismatched base are enclosed in rectangles. The nucleotides in which the group at the 2'-position of the pentose was replaced by $OCH_3$ are hatched.

siGY441:

(SEQ ID NO. 140)

5'-GCCACAACGUCUAUAUCAUGG-3'

(SEQ ID NO. 141)

3'-GUCGGUGUUGCAGAUAUAGUA-5' siKRAS-62:

(SEQ ID NO. 142)

5'-CAGCUAAUUCAGAAUCAUUUU-3'

(SEQ ID NO. 143)

3'-AUGUCGAUUAAGUCUUAGUAA-5'

-continued

```
siKRAS-WT:
                                 (SEQ ID NO. 144)
5'-UGGAGCUGGUGGCGUAGGCAA-3'

(SEQ ID NO. 145)
3'-CAACCUCGACCACCGCAUCCG-5' siKRAS-A(K(35)11ArevOM(6-8)M6):
                                 (SEQ ID NO. 36)
5'-GGGAGCUGAUGGCGUAGGAAA-3'

(SEQ ID NO. 37)
3'-CACCCUCGACUACCGGAUCCU-5'
```

As shown in the graphs, in BxPC-3 which is homozygous for the wild-type, siKRAS-62 and siKRAS-WT strongly suppressed the expression; in AsPC-1 which is homozygous for the A-type mutation, siKRAS-62 and siKRAS-A strongly suppressed the expression; and in PANC-1 which is heterozygous for the A-type mutation, siKRAS-62 strongly suppressed the expression and siKRAS-WT and siKRAS-A weakly suppressed the expression. The genotypes of the cells correlated to the specificities of the siRNAs for endogenous genes as well.

Thus, each siRNA can suppress the expressions of endogenous genes with similar specificities to those for exogenous genes such as reporter.

Example 3

This example shows that siKRAS-A can inhibit tumor cell growth in vivo.

Figure 13:
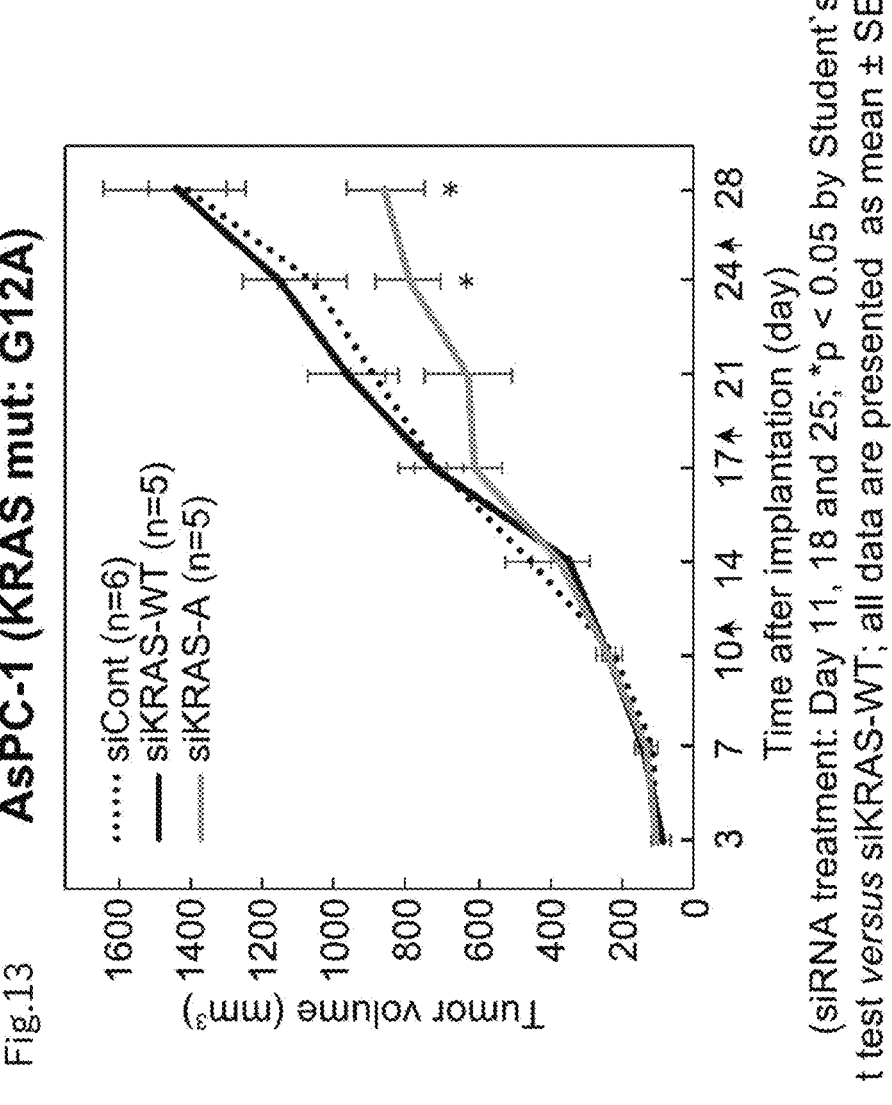
FIG. 13 shows a graph of the results indicating that siKRAS-A can inhibit tumor cell growth in vivo, in one example of the present invention.

$1.0 \times 10^6$ AsPC-1 cells were implanted subcutaneously into three nude mice (BALB/cAJcl Foxn1$^{null}$) at 5-6 sites each. Proliferation ability of each tumor was evaluated by measuring tumor volume using a caliper twice a week. Tumor size on Day 10 after implantation increased to about 2-fold compared to that on Day 3 after implantation; thus, the tumor was considered to be in the growth phase. Starting on Day 11, a mixture of 5 µg of siRNA (siCont, siKRAS-WT or siKRAS-A) and in vivo JET PEI transfection reagent (Polyplus Transfection) was directly administered to each tumor using a 27G needle every other week. Each animal received either one of siRNAs. The results are shown as a graph in FIG. 13.

In the group that received siKRAS-A, the tumor sizes were significantly reduced on Day 24 after implantation and afterwards, compared with those in the siCont and siKRAS-WT groups.

Thus, siKRAS-A can inhibit the growth of the cells which grow in a mutant K-ras-dependent manner.

INDUSTRIAL APPLICABILITY

The present invention allowed to provide novel RNA molecules, novel chimeric NA molecules, novel double-stranded RNA molecules, and novel double-stranded chimeric NA molecules.

---

The invention claimed is:

1. An RNA molecule for use in RNA interference to target a mutant allele of a gene, the mutant allele having a point mutation relative to a wild-type allele of the gene, the RNA molecule satisfying the following conditions:

(1) the molecule has a nucleotide sequence complementary to a nucleotide sequence of a coding region of the mutant allele except for a base specified in (2-1) below; and (2) when counted from the base at the 5'-end in a nucleotide sequence complementary to the nucleotide sequence of the mutant allele, (2-1) a base at position 5 or 6 is mismatched to a base in the mutant allele;

(2-2) a position 10 or 11 corresponds to the position of the point mutation, and the base at position 10 or 11 is complementary to the base at the position of the point mutation in the mutant allele; and (2-3) a group at the 2'-position of a pentose in each of ribonucleotides at positions 6-8 or positions 7 and 8 is modified with $OCH_3$ or fluorine.

2. The RNA molecule according to claim 1, wherein, when a base at the 5'-end of the nucleotide sequence specified in (1) of claim 1 is cytosine or guanine, it is replaced by adenine or uracil.

3. The RNA molecule according to claim 1, wherein, when a base at the 3'-end of the nucleotide sequence specified in (1) of claim 1 is adenine or uracil, it is replaced by cytosine or guanine.

4. The RNA molecule according to claim 1, wherein the RNA molecule comprises 13-28 nucleotides.

5. The RNA molecule according to claim 1, further comprising 1-3 nucleotide(s) at the 3'-end of the nucleotide sequence specified in (1) of claim 1.

6. A chimeric NA molecule, wherein one or more ribonucleotides in an RNA molecule according to claim 1 are replaced by a deoxyribonucleotide, an artificial nucleic acid, or a nucleic acid analog.

7. A double-stranded RNA molecule comprising a guide strand and a passenger strand, the guide strand being an RNA molecule according to claim 1, and the passenger strand being an RNA molecule with a sequence complementary to that of the RNA molecule of the guide strand.

8. The double-stranded RNA molecule according to claim 7, wherein the RNA molecule comprises an overhang at the 3'-end of the guide strand and/or an overhang at the 3'-end of the passenger strand.

9. The double-stranded RNA molecule according to claim 8, wherein the overhang(s) comprise 1-3 nucleotides.

10. A double-stranded chimeric NA molecule, wherein one or more ribonucleotides in a double-stranded RNA molecule according to claim 7 is by a deoxyribonucleotide, an artificial nucleic acid, or a nucleic acid analog.

11. A method for producing the RNA molecule according to claim 1, comprising making a RNA molecule having a nucleotide sequence complementary to a nucleotide sequence of a coding region of a mutant allele of a gene, wherein the mutant allele has a point mutation relative to a wild-type allele of the gene, except the method comprises making the RNA molecule sequence have a base at position 5 or 6 that is mismatched to a base in the mutant allele from the 5'-end of the RNA molecule sequence; and further comprising making position 10 or 11 from the 5'-end of the RNA molecule sequence correspond to the position of the point mutation, and the base at position 10 or 11 complementary to the base at the position of the point mutation in the mutant allele, and a group at the 2'-position of a pentose in each of ribonucleotides at positions 6-8 or positions 7 and 8 modified with $OCH_3$ or fluorine.

12. A method for producing the chimeric NA molecule according to claim 6, comprising making a RNA molecule having a nucleotide sequence complementary to a nucleotide sequence of a coding region of a mutant allele of a gene, wherein the mutant allele has a point mutation relative to a wild-type allele of the gene, except the method comprises making the RNA molecule sequence have a base at position 5 or 6 that is mismatched to a base in the mutant allele from the 5'-end of the RNA molecule sequence;

further comprising making position 10 or 11 from the 5'-end of the RNA molecule sequence correspond to the position of the point mutation, and the base at position 10 or 11 complementary to the base at the position of the point mutation in the mutant allele, and a group at the 2'-position of a pentose in each of ribonucleotides at positions 6-8 or positions 7 and 8 modified with $OCH_3$ or fluorine; and wherein one or more ribonucleotides in the RNA molecule are replaced with a deoxyribonucleotide, an artificial nucleic acid, or a nucleic acid analog.

13. A method for performing RNA interference in a cell containing a wild-type allele of a gene and a mutant allele of the gene, by targeting the mutant allele with an RNA molecule, the mutant allele having a point mutation, wherein the method comprises the step of:

introducing the RNA molecule according to claim 1 into the cell.

* * * * *

SEQUENCE LISTING

```
<160> NUMBER OF SEQ ID NOS: 155

<210> SEQ ID NO 1
<211> LENGTH: 19
<212> TYPE: RNA
<213> ORGANISM: Artificial Sequence
<220> FEATURE:
<223> OTHER INFORMATION: siRNA

<400> SEQUENCE: 1
uccuacgcca ucagcucca                                          19

<210> SEQ ID NO 2
<211> LENGTH: 19
<212> TYPE: RNA
<213> ORGANISM: Artificial Sequence
<220> FEATURE:
<223> OTHER INFORMATION: siRNA

<400> SEQUENCE: 2
uccuacgcca acagcucca                                          19

<210> SEQ ID NO 3
<211> LENGTH: 19
<212> TYPE: RNA
<213> ORGANISM: Artificial Sequence
<220> FEATURE:
<223> OTHER INFORMATION: siRNA

<400> SEQUENCE: 3
uccuacgcca gcagcucca                                          19

<210> SEQ ID NO 4
<211> LENGTH: 33
<212> TYPE: DNA
```

-continued

```
<213> ORGANISM: Artificial Sequence
<220> FEATURE:
<223> OTHER INFORMATION: reporter

<400> SEQUENCE: 4
tggtagttgg agctggtggc gtaggcaaga gtg                                    33

<210> SEQ ID NO 5
<211> LENGTH: 33
<212> TYPE: DNA
<213> ORGANISM: Artificial Sequence
<220> FEATURE:
<223> OTHER INFORMATION: reporter

<400> SEQUENCE: 5
cactcttgcc tacgccacca gctccaacta cca                                    33

<210> SEQ ID NO 6
<211> LENGTH: 33
<212> TYPE: DNA
<213> ORGANISM: Artificial Sequence
<220> FEATURE:
<223> OTHER INFORMATION: reporter

<400> SEQUENCE: 6
tggtagttgg agctgatggc gtaggcaaga gtg                                    33

<210> SEQ ID NO 7
<211> LENGTH: 33
<212> TYPE: DNA
<213> ORGANISM: Artificial Sequence
<220> FEATURE:
<223> OTHER INFORMATION: reporter

<400> SEQUENCE: 7
cactcttgcc tacgccatca gctccaacta cca                                    33

<210> SEQ ID NO 8
<211> LENGTH: 21
<212> TYPE: DNA
<213> ORGANISM: Artificial Sequence
<220> FEATURE:
<223> OTHER INFORMATION: siRNA

<400> SEQUENCE: 8
guuggagcug auggcguagt t                                                 21

<210> SEQ ID NO 9
<211> LENGTH: 21
<212> TYPE: DNA
<213> ORGANISM: Artificial Sequence
<220> FEATURE:
<223> OTHER INFORMATION: siRNA

<400> SEQUENCE: 9
cuacgccauc agcuccaact t                                                 21

<210> SEQ ID NO 10
<211> LENGTH: 21
<212> TYPE: RNA
<213> ORGANISM: Artificial Sequence
<220> FEATURE:
<223> OTHER INFORMATION: siRNA

<400> SEQUENCE: 10
uuggagcuga uggcguaggc a                                                 21
```

```
<210> SEQ ID NO 11
<211> LENGTH: 21
<212> TYPE: RNA
<213> ORGANISM: Artificial Sequence
<220> FEATURE:
<223> OTHER INFORMATION: siRNA

<400> SEQUENCE: 11
ccuacgccau cagcuccaac u                                              21

<210> SEQ ID NO 12
<211> LENGTH: 21
<212> TYPE: RNA
<213> ORGANISM: Artificial Sequence
<220> FEATURE:
<223> OTHER INFORMATION: siRNA

<400> SEQUENCE: 12
uggagcugau ggcguaggca a                                              21

<210> SEQ ID NO 13
<211> LENGTH: 21
<212> TYPE: RNA
<213> ORGANISM: Artificial Sequence
<220> FEATURE:
<223> OTHER INFORMATION: siRNA

<400> SEQUENCE: 13
gccuacgcca ucagcuccaa c                                              21

<210> SEQ ID NO 14
<211> LENGTH: 21
<212> TYPE: RNA
<213> ORGANISM: Artificial Sequence
<220> FEATURE:
<223> OTHER INFORMATION: siRNA

<400> SEQUENCE: 14
gggagcugau ggcguaggaa a                                              21

<210> SEQ ID NO 15
<211> LENGTH: 21
<212> TYPE: RNA
<213> ORGANISM: Artificial Sequence
<220> FEATURE:
<223> OTHER INFORMATION: siRNA

<400> SEQUENCE: 15
uccuacgcca ucagcuccca c                                              21

<210> SEQ ID NO 16
<211> LENGTH: 21
<212> TYPE: RNA
<213> ORGANISM: Artificial Sequence
<220> FEATURE:
<223> OTHER INFORMATION: siRNA

<400> SEQUENCE: 16
gggagcugau ggcguaggaa a                                              21

<210> SEQ ID NO 17
<211> LENGTH: 21
<212> TYPE: RNA
<213> ORGANISM: Artificial Sequence
<220> FEATURE:
```

```
<223> OTHER INFORMATION: siRNA

<400> SEQUENCE: 17
uccuacgcca ucagcuccca c                                               21

<210> SEQ ID NO 18
<211> LENGTH: 21
<212> TYPE: RNA
<213> ORGANISM: Artificial Sequence
<220> FEATURE:
<223> OTHER INFORMATION: siRNA

<400> SEQUENCE: 18
gggagcugau ggcguaggaa a                                               21

<210> SEQ ID NO 19
<211> LENGTH: 21
<212> TYPE: RNA
<213> ORGANISM: Artificial Sequence
<220> FEATURE:
<223> OTHER INFORMATION: siRNA

<400> SEQUENCE: 19
uccuacgcca ucagcuccca c                                               21

<210> SEQ ID NO 20
<211> LENGTH: 21
<212> TYPE: RNA
<213> ORGANISM: Artificial Sequence
<220> FEATURE:
<223> OTHER INFORMATION: siRNA

<400> SEQUENCE: 20
gggagcugau ggcguacgaa a                                               21

<210> SEQ ID NO 21
<211> LENGTH: 21
<212> TYPE: RNA
<213> ORGANISM: Artificial Sequence
<220> FEATURE:
<223> OTHER INFORMATION: siRNA

<400> SEQUENCE: 21
ucguacgcca ucagcuccca c                                               21

<210> SEQ ID NO 22
<211> LENGTH: 21
<212> TYPE: RNA
<213> ORGANISM: Artificial Sequence
<220> FEATURE:
<223> OTHER INFORMATION: siRNA

<400> SEQUENCE: 22
gggagcugau ggcguuggaa a                                               21

<210> SEQ ID NO 23
<211> LENGTH: 21
<212> TYPE: RNA
<213> ORGANISM: Artificial Sequence
<220> FEATURE:
<223> OTHER INFORMATION: siRNA

<400> SEQUENCE: 23
uccaacgcca ucagcuccca c                                               21
```

-continued

```
<210> SEQ ID NO 24
<211> LENGTH: 21
<212> TYPE: RNA
<213> ORGANISM: Artificial Sequence
<220> FEATURE:
<223> OTHER INFORMATION: siRNA

<400> SEQUENCE: 24
gggagcugau ggcgaaggaa a                                                    21

<210> SEQ ID NO 25
<211> LENGTH: 21
<212> TYPE: RNA
<213> ORGANISM: Artificial Sequence
<220> FEATURE:
<223> OTHER INFORMATION: siRNA

<400> SEQUENCE: 25
uccuucgcca ucagcuccca c                                                    21

<210> SEQ ID NO 26
<211> LENGTH: 21
<212> TYPE: RNA
<213> ORGANISM: Artificial Sequence
<220> FEATURE:
<223> OTHER INFORMATION: siRNA

<400> SEQUENCE: 26
gggagcugau ggccuaggaa a                                                    21

<210> SEQ ID NO 27
<211> LENGTH: 21
<212> TYPE: RNA
<213> ORGANISM: Artificial Sequence
<220> FEATURE:
<223> OTHER INFORMATION: siRNA

<400> SEQUENCE: 27
uccuaggcca ucagcuccca c                                                    21

<210> SEQ ID NO 28
<211> LENGTH: 21
<212> TYPE: RNA
<213> ORGANISM: Artificial Sequence
<220> FEATURE:
<223> OTHER INFORMATION: siRNA

<400> SEQUENCE: 28
gggagcugau gggguaggaa a                                                    21

<210> SEQ ID NO 29
<211> LENGTH: 21
<212> TYPE: RNA
<213> ORGANISM: Artificial Sequence
<220> FEATURE:
<223> OTHER INFORMATION: siRNA

<400> SEQUENCE: 29
uccuacccca ucagcuccca c                                                    21

<210> SEQ ID NO 30
<211> LENGTH: 21
<212> TYPE: RNA
<213> ORGANISM: Artificial Sequence
<220> FEATURE:
<223> OTHER INFORMATION: siRNA
```

-continued

<400> SEQUENCE: 30
gggagcugau ggcguacgaa a                                                    21

<210> SEQ ID NO 31
<211> LENGTH: 21
<212> TYPE: RNA
<213> ORGANISM: Artificial Sequence
<220> FEATURE:
<223> OTHER INFORMATION: siRNA

<400> SEQUENCE: 31
ucguacgcca ucagcuccca c                                                    21

<210> SEQ ID NO 32
<211> LENGTH: 21
<212> TYPE: RNA
<213> ORGANISM: Artificial Sequence
<220> FEATURE:
<223> OTHER INFORMATION: siRNA

<400> SEQUENCE: 32
gggagcugau ggcguuggaa a                                                    21

<210> SEQ ID NO 33
<211> LENGTH: 21
<212> TYPE: RNA
<213> ORGANISM: Artificial Sequence
<220> FEATURE:
<223> OTHER INFORMATION: siRNA

<400> SEQUENCE: 33
uccaacgcca ucagcuccca c                                                    21

<210> SEQ ID NO 34
<211> LENGTH: 21
<212> TYPE: RNA
<213> ORGANISM: Artificial Sequence
<220> FEATURE:
<223> OTHER INFORMATION: siRNA

<400> SEQUENCE: 34
gggagcugau ggcgaaggaa a                                                    21

<210> SEQ ID NO 35
<211> LENGTH: 21
<212> TYPE: RNA
<213> ORGANISM: Artificial Sequence
<220> FEATURE:
<223> OTHER INFORMATION: siRNA

<400> SEQUENCE: 35
uccuucgcca ucagcuccca c                                                    21

<210> SEQ ID NO 36
<211> LENGTH: 21
<212> TYPE: RNA
<213> ORGANISM: Artificial Sequence
<220> FEATURE:
<223> OTHER INFORMATION: siRNA

<400> SEQUENCE: 36
gggagcugau ggccuaggaa a                                                    21

<210> SEQ ID NO 37
<211> LENGTH: 21

-continued

```
<212> TYPE: RNA
<213> ORGANISM: Artificial Sequence
<220> FEATURE:
<223> OTHER INFORMATION: siRNA

<400> SEQUENCE: 37
uccuaggcca ucagcuccca c                                            21

<210> SEQ ID NO 38
<211> LENGTH: 21
<212> TYPE: RNA
<213> ORGANISM: Artificial Sequence
<220> FEATURE:
<223> OTHER INFORMATION: siRNA

<400> SEQUENCE: 38
gggagcugau gggguaggaa a                                            21

<210> SEQ ID NO 39
<211> LENGTH: 21
<212> TYPE: RNA
<213> ORGANISM: Artificial Sequence
<220> FEATURE:
<223> OTHER INFORMATION: siRNA

<400> SEQUENCE: 39
uccuacccca ucagcuccca c                                            21

<210> SEQ ID NO 40
<211> LENGTH: 33
<212> TYPE: DNA
<213> ORGANISM: Artificial Sequence
<220> FEATURE:
<223> OTHER INFORMATION: reporter

<400> SEQUENCE: 40
tggtagttgg agctgttggc gtaggcaaga gtg                               33

<210> SEQ ID NO 41
<211> LENGTH: 33
<212> TYPE: DNA
<213> ORGANISM: Artificial Sequence
<220> FEATURE:
<223> OTHER INFORMATION: reporter

<400> SEQUENCE: 41
cactcttgcc tacgccaaca gctccaacta cca                               33

<210> SEQ ID NO 42
<211> LENGTH: 33
<212> TYPE: DNA
<213> ORGANISM: Artificial Sequence
<220> FEATURE:
<223> OTHER INFORMATION: reporter

<400> SEQUENCE: 42
tggtagttgg agctgctggc gtaggcaaga gtg                               33

<210> SEQ ID NO 43
<211> LENGTH: 33
<212> TYPE: DNA
<213> ORGANISM: Artificial Sequence
<220> FEATURE:
<223> OTHER INFORMATION: reporter

<400> SEQUENCE: 43
```

-continued cactcttgcc tacgccagca gctccaacta cca                                33

<210> SEQ ID NO 44
<211> LENGTH: 21
<212> TYPE: RNA
<213> ORGANISM: Artificial Sequence
<220> FEATURE:
<223> OTHER INFORMATION: siRNA

<400> SEQUENCE: 44
gggagcuguu ggcguaggaa a                                             21

<210> SEQ ID NO 45
<211> LENGTH: 21
<212> TYPE: RNA
<213> ORGANISM: Artificial Sequence
<220> FEATURE:
<223> OTHER INFORMATION: siRNA

<400> SEQUENCE: 45
uccuacgcca acagcuccca c                                             21

<210> SEQ ID NO 46
<211> LENGTH: 21
<212> TYPE: RNA
<213> ORGANISM: Artificial Sequence
<220> FEATURE:
<223> OTHER INFORMATION: siRNA

<400> SEQUENCE: 46
gggagcuguu ggcgaaggaa a                                             21

<210> SEQ ID NO 47
<211> LENGTH: 21
<212> TYPE: RNA
<213> ORGANISM: Artificial Sequence
<220> FEATURE:
<223> OTHER INFORMATION: siRNA

<400> SEQUENCE: 47
uccuucgcca acagcuccca c                                             21

<210> SEQ ID NO 48
<211> LENGTH: 21
<212> TYPE: RNA
<213> ORGANISM: Artificial Sequence
<220> FEATURE:
<223> OTHER INFORMATION: siRNA

<400> SEQUENCE: 48
gggagcuguu ggccuaggaa a                                             21

<210> SEQ ID NO 49
<211> LENGTH: 21
<212> TYPE: RNA
<213> ORGANISM: Artificial Sequence
<220> FEATURE:
<223> OTHER INFORMATION: siRNA

<400> SEQUENCE: 49
uccuaggcca acagcuccca c                                             21

<210> SEQ ID NO 50
<211> LENGTH: 21
<212> TYPE: RNA
<213> ORGANISM: Artificial Sequence -continued

```
<220> FEATURE:
<223> OTHER INFORMATION: siRNA

<400> SEQUENCE: 50
gggagcugcu ggcguaggaa a                                              21

<210> SEQ ID NO 51
<211> LENGTH: 21
<212> TYPE: RNA
<213> ORGANISM: Artificial Sequence
<220> FEATURE:
<223> OTHER INFORMATION: siRNA

<400> SEQUENCE: 51
uccuacgcca gcagcuccca c                                              21

<210> SEQ ID NO 52
<211> LENGTH: 21
<212> TYPE: RNA
<213> ORGANISM: Artificial Sequence
<220> FEATURE:
<223> OTHER INFORMATION: siRNA

<400> SEQUENCE: 52
gggagcugcu ggcgaaggaa a                                              21

<210> SEQ ID NO 53
<211> LENGTH: 21
<212> TYPE: RNA
<213> ORGANISM: Artificial Sequence
<220> FEATURE:
<223> OTHER INFORMATION: siRNA

<400> SEQUENCE: 53
uccuucgcca gcagcuccca c                                              21

<210> SEQ ID NO 54
<211> LENGTH: 21
<212> TYPE: RNA
<213> ORGANISM: Artificial Sequence
<220> FEATURE:
<223> OTHER INFORMATION: siRNA

<400> SEQUENCE: 54
gggagcugcu ggccuaggaa a                                              21

<210> SEQ ID NO 55
<211> LENGTH: 20
<212> TYPE: RNA
<213> ORGANISM: Artificial Sequence
<220> FEATURE:
<223> OTHER INFORMATION: siRNA

<400> SEQUENCE: 55
uccuaggcca gcagcuccca                                                20

<210> SEQ ID NO 56
<211> LENGTH: 40
<212> TYPE: DNA
<213> ORGANISM: Artificial Sequence
<220> FEATURE:
<223> OTHER INFORMATION: reporter

<400> SEQUENCE: 56
actggtggtg gttggagcag gtggtgttgg gaaaagcgca                          40
```

-continued

```
<210> SEQ ID NO 57
<211> LENGTH: 40
<212> TYPE: DNA
<213> ORGANISM: Artificial Sequence
<220> FEATURE:
<223> OTHER INFORMATION: reporter

<400> SEQUENCE: 57
tgcgcttttc ccaacaccac cagctccaac caccaccagt                             40

<210> SEQ ID NO 58
<211> LENGTH: 40
<212> TYPE: DNA
<213> ORGANISM: Artificial Sequence
<220> FEATURE:
<223> OTHER INFORMATION: reporter

<400> SEQUENCE: 58
actggtggtg gttggagcag atggtgttgg gaaaagcgca                             40

<210> SEQ ID NO 59
<211> LENGTH: 40
<212> TYPE: DNA
<213> ORGANISM: Artificial Sequence
<220> FEATURE:
<223> OTHER INFORMATION: reporter

<400> SEQUENCE: 59
tgcgcttttc ccaacaccat cagctccaac caccaccagt                             40

<210> SEQ ID NO 60
<211> LENGTH: 21
<212> TYPE: RNA
<213> ORGANISM: Artificial Sequence
<220> FEATURE:
<223> OTHER INFORMATION: primer

<400> SEQUENCE: 60
uggagcaggu gguguuggga a                                                 21

<210> SEQ ID NO 61
<211> LENGTH: 21
<212> TYPE: RNA
<213> ORGANISM: Artificial Sequence
<220> FEATURE:
<223> OTHER INFORMATION: primer

<400> SEQUENCE: 61
cccaacacca ccugcuccaa c                                                 21

<210> SEQ ID NO 62
<211> LENGTH: 21
<212> TYPE: RNA
<213> ORGANISM: Artificial Sequence
<220> FEATURE:
<223> OTHER INFORMATION: primer

<400> SEQUENCE: 62
uggagcagau gguguuggga a                                                 21

<210> SEQ ID NO 63
<211> LENGTH: 21
<212> TYPE: RNA
<213> ORGANISM: Artificial Sequence
<220> FEATURE:
<223> OTHER INFORMATION: primer
```

<400> SEQUENCE: 63
cccaacacca ucugcuccaa c                                              21

<210> SEQ ID NO 64
<211> LENGTH: 21
<212> TYPE: RNA
<213> ORGANISM: Artificial Sequence
<220> FEATURE:
<223> OTHER INFORMATION: primer

<400> SEQUENCE: 64
cggagcagau ggugauggaa a                                              21

<210> SEQ ID NO 65
<211> LENGTH: 21
<212> TYPE: RNA
<213> ORGANISM: Artificial Sequence
<220> FEATURE:
<223> OTHER INFORMATION: primer

<400> SEQUENCE: 65
uccaucacca ucugcuccga c                                              21

<210> SEQ ID NO 66
<211> LENGTH: 38
<212> TYPE: DNA
<213> ORGANISM: Artificial Sequence
<220> FEATURE:
<223> OTHER INFORMATION: reporter

<400> SEQUENCE: 66
catactggat acagctggac aagaagagta cagtgcca                            38

<210> SEQ ID NO 67
<211> LENGTH: 38
<212> TYPE: DNA
<213> ORGANISM: Artificial Sequence
<220> FEATURE:
<223> OTHER INFORMATION: reporter

<400> SEQUENCE: 67
tggcactgta ctcttcttgt ccagctgtat ccagtatg                            38

<210> SEQ ID NO 68
<211> LENGTH: 38
<212> TYPE: DNA
<213> ORGANISM: Artificial Sequence
<220> FEATURE:
<223> OTHER INFORMATION: reporter

<400> SEQUENCE: 68
catactggat acagctggac gagaagagta cagtgcca                            38

<210> SEQ ID NO 69
<211> LENGTH: 38
<212> TYPE: DNA
<213> ORGANISM: Artificial Sequence
<220> FEATURE:
<223> OTHER INFORMATION: reporter

<400> SEQUENCE: 69
tggcactgta ctcttctcgt ccagctgtat ccagtatg                            38

<210> SEQ ID NO 70

```
<211> LENGTH: 21
<212> TYPE: RNA
<213> ORGANISM: Artificial Sequence
<220> FEATURE:
<223> OTHER INFORMATION: siRNA

<400> SEQUENCE: 70
agcuggacaa gaagaguaca g                                                21

<210> SEQ ID NO 71
<211> LENGTH: 21
<212> TYPE: RNA
<213> ORGANISM: Artificial Sequence
<220> FEATURE:
<223> OTHER INFORMATION: siRNA

<400> SEQUENCE: 71
guacucuucu uguccagcug u                                                21

<210> SEQ ID NO 72
<211> LENGTH: 21
<212> TYPE: RNA
<213> ORGANISM: Artificial Sequence
<220> FEATURE:
<223> OTHER INFORMATION: siRNA

<400> SEQUENCE: 72
agcuggacga gaagaguaca g                                                21

<210> SEQ ID NO 73
<211> LENGTH: 21
<212> TYPE: RNA
<213> ORGANISM: Artificial Sequence
<220> FEATURE:
<223> OTHER INFORMATION: siRNA

<400> SEQUENCE: 73
guacucuucu cguccagcug u                                                21

<210> SEQ ID NO 74
<211> LENGTH: 21
<212> TYPE: RNA
<213> ORGANISM: Artificial Sequence
<220> FEATURE:
<223> OTHER INFORMATION: siRNA

<400> SEQUENCE: 74
ggcuggacga gaaguguaaa g                                                21

<210> SEQ ID NO 75
<211> LENGTH: 21
<212> TYPE: RNA
<213> ORGANISM: Artificial Sequence
<220> FEATURE:
<223> OTHER INFORMATION: siRNA

<400> SEQUENCE: 75
uuacacuucu cguccagccg u                                                21

<210> SEQ ID NO 76
<211> LENGTH: 41
<212> TYPE: DNA
<213> ORGANISM: Artificial Sequence
<220> FEATURE:
<223> OTHER INFORMATION: reporter

<400> SEQUENCE: 76
```

-continued

```
cattagattc aaatgtagca aatcagaagc cctttgagag t                     41

<210> SEQ ID NO 77
<211> LENGTH: 41
<212> TYPE: DNA
<213> ORGANISM: Artificial Sequence
<220> FEATURE:
<223> OTHER INFORMATION: reporter

<400> SEQUENCE: 77
actctcaaag ggcttctgat ttgctacatt tgaatctaat g                     41

<210> SEQ ID NO 78
<211> LENGTH: 41
<212> TYPE: DNA
<213> ORGANISM: Artificial Sequence
<220> FEATURE:
<223> OTHER INFORMATION: reporter

<400> SEQUENCE: 78
cattagattc aaatgtagca catcagaagc cctttgagag t                     41

<210> SEQ ID NO 79
<211> LENGTH: 41
<212> TYPE: DNA
<213> ORGANISM: Artificial Sequence
<220> FEATURE:
<223> OTHER INFORMATION: reporter

<400> SEQUENCE: 79
actctcaaag ggcttctgat gtgctacatt tgaatctaat g                     41

<210> SEQ ID NO 80
<211> LENGTH: 41
<212> TYPE: DNA
<213> ORGANISM: Artificial Sequence
<220> FEATURE:
<223> OTHER INFORMATION: reporter

<400> SEQUENCE: 80
gacgaggacg aggacctctt cgacatcgag gatgacatca t                     41

<210> SEQ ID NO 81
<211> LENGTH: 41
<212> TYPE: DNA
<213> ORGANISM: Artificial Sequence
<220> FEATURE:
<223> OTHER INFORMATION: reporter

<400> SEQUENCE: 81
atgatgtcat cctcgatgtc gaagaggtcc tcgtcctcgt c                     41

<210> SEQ ID NO 82
<211> LENGTH: 41
<212> TYPE: DNA
<213> ORGANISM: Artificial Sequence
<220> FEATURE:
<223> OTHER INFORMATION: reporter

<400> SEQUENCE: 82
gacgaggacg aggacctctt ggacatcgag gatgacatca t                     41

<210> SEQ ID NO 83
<211> LENGTH: 41
<212> TYPE: DNA
```

```
<213> ORGANISM: Artificial Sequence
<220> FEATURE:
<223> OTHER INFORMATION: reporter

<400> SEQUENCE: 83
atgatgtcat cctcgatgtc caagaggtcc tcgtcctcgt c                          41

<210> SEQ ID NO 84
<211> LENGTH: 41
<212> TYPE: DNA
<213> ORGANISM: Artificial Sequence
<220> FEATURE:
<223> OTHER INFORMATION: reporter

<400> SEQUENCE: 84
actgtaaagc tggaaaggga cgaactggtg taatgatatg t                          41

<210> SEQ ID NO 85
<211> LENGTH: 41
<212> TYPE: DNA
<213> ORGANISM: Artificial Sequence
<220> FEATURE:
<223> OTHER INFORMATION: reporter

<400> SEQUENCE: 85
acatatcatt acaccagttc gtccctttcc agctttacag t                          41

<210> SEQ ID NO 86
<211> LENGTH: 41
<212> TYPE: DNA
<213> ORGANISM: Artificial Sequence
<220> FEATURE:
<223> OTHER INFORMATION: reporter

<400> SEQUENCE: 86
actgtaaagc tggaaaggga ggaactggtg taatgatatg t                          41

<210> SEQ ID NO 87
<211> LENGTH: 41
<212> TYPE: DNA
<213> ORGANISM: Artificial Sequence
<220> FEATURE:
<223> OTHER INFORMATION: v

<400> SEQUENCE: 87
acatatcatt acaccagttc ctccctttcc agctttacag t                          41

<210> SEQ ID NO 88
<211> LENGTH: 41
<212> TYPE: DNA
<213> ORGANISM: Artificial Sequence
<220> FEATURE:
<223> OTHER INFORMATION: reporter

<400> SEQUENCE: 88
ctcaaacagc tcaaaccaag cgagaagtac ctaaaaataa a                          41

<210> SEQ ID NO 89
<211> LENGTH: 41
<212> TYPE: DNA
<213> ORGANISM: Artificial Sequence
<220> FEATURE:
<223> OTHER INFORMATION: reporter

<400> SEQUENCE: 89
tttattttta ggtacttctc gcttggtttg agctgtttga g                          41
```

```
<210> SEQ ID NO 90
<211> LENGTH: 41
<212> TYPE: DNA
<213> ORGANISM: Artificial Sequence
<220> FEATURE:
<223> OTHER INFORMATION: reporter

<400> SEQUENCE: 90
ctcaaacagc tcaaaccaag tgagaagtac ctaaaaataa a                         41

<210> SEQ ID NO 91
<211> LENGTH: 41
<212> TYPE: DNA
<213> ORGANISM: Artificial Sequence
<220> FEATURE:
<223> OTHER INFORMATION: reporter

<400> SEQUENCE: 91 tttatttta ggtacttctc acttggtttg agctgtttga g                          41

<210> SEQ ID NO 92
<211> LENGTH: 41
<212> TYPE: DNA
<213> ORGANISM: Artificial Sequence
<220> FEATURE:
<223> OTHER INFORMATION: reporter

<400> SEQUENCE: 92
cggccactac ctgtgcaatg cctgtggcct ctaccacaag a                         41

<210> SEQ ID NO 93
<211> LENGTH: 41
<212> TYPE: DNA
<213> ORGANISM: Artificial Sequence
<220> FEATURE:
<223> OTHER INFORMATION: reporter

<400> SEQUENCE: 93
tcttgtggta gaggccacag gcattgcaca ggtagtggcc g                         41

<210> SEQ ID NO 94
<211> LENGTH: 41
<212> TYPE: DNA
<213> ORGANISM: Artificial Sequence
<220> FEATURE:
<223> OTHER INFORMATION: reporter

<400> SEQUENCE: 94
cggccactac ctgtgcaatg tctgtggcct ctaccacaag a                         41

<210> SEQ ID NO 95
<211> LENGTH: 41
<212> TYPE: DNA
<213> ORGANISM: Artificial Sequence
<220> FEATURE:
<223> OTHER INFORMATION: reporter

<400> SEQUENCE: 95
tcttgtggta gaggccacag acattgcaca ggtagtggcc g                         41

<210> SEQ ID NO 96
<211> LENGTH: 41
<212> TYPE: DNA
<213> ORGANISM: Artificial Sequence
<220> FEATURE:
```

-continued

<223> OTHER INFORMATION: reporter

<400> SEQUENCE: 96
aggtgcccat cagaagcgac tgatccccat caagtacaag g                    41

<210> SEQ ID NO 97
<211> LENGTH: 41
<212> TYPE: DNA
<213> ORGANISM: Artificial Sequence
<220> FEATURE:
<223> OTHER INFORMATION: reporter

<400> SEQUENCE: 97
ccttgtactt gatggggatc agtcgcttct gatgggcacc t                    41

<210> SEQ ID NO 98
<211> LENGTH: 41
<212> TYPE: DNA
<213> ORGANISM: Artificial Sequence
<220> FEATURE:
<223> OTHER INFORMATION: reporter

<400> SEQUENCE: 98
aggtgcccat cagaagcgac cgatccccat caagtacaag g                    41

<210> SEQ ID NO 99
<211> LENGTH: 41
<212> TYPE: DNA
<213> ORGANISM: Artificial Sequence
<220> FEATURE:
<223> OTHER INFORMATION: reporter

<400> SEQUENCE: 99
ccttgtactt gatggggatc ggtcgcttct gatgggcacc t                    41

<210> SEQ ID NO 100
<211> LENGTH: 41
<212> TYPE: DNA
<213> ORGANISM: Artificial Sequence
<220> FEATURE:
<223> OTHER INFORMATION: reporter

<400> SEQUENCE: 100
aatggtcgat gtagggggcc aaaggtcaga gagaagaaaa t                    41

<210> SEQ ID NO 101
<211> LENGTH: 41
<212> TYPE: DNA
<213> ORGANISM: Artificial Sequence
<220> FEATURE:
<223> OTHER INFORMATION: reporter

<400> SEQUENCE: 101
attttcttct ctctgacctt tggcccccta catcgaccat t                    41

<210> SEQ ID NO 102
<211> LENGTH: 41
<212> TYPE: DNA
<213> ORGANISM: Artificial Sequence
<220> FEATURE:
<223> OTHER INFORMATION: reporter

<400> SEQUENCE: 102
aatggtcgat gtagggggcc taaggtcaga gagaagaaaa t                    41

-continued

```
<210> SEQ ID NO 103
<211> LENGTH: 41
<212> TYPE: DNA
<213> ORGANISM: Artificial Sequence
<220> FEATURE:
<223> OTHER INFORMATION: reporter

<400> SEQUENCE: 103
attttcttct ctctgacctt aggcccccta catcgaccat t                41

<210> SEQ ID NO 104
<211> LENGTH: 38
<212> TYPE: DNA
<213> ORGANISM: Artificial Sequence
<220> FEATURE:
<223> OTHER INFORMATION: reporter

<400> SEQUENCE: 104
aaaacctatc atcataggtc gtcatgctta tggggatc                    38

<210> SEQ ID NO 105
<211> LENGTH: 38
<212> TYPE: DNA
<213> ORGANISM: Artificial Sequence
<220> FEATURE:
<223> OTHER INFORMATION: reporter

<400> SEQUENCE: 105
gatccccata agcatgacga cctatgatga taggtttt                    38

<210> SEQ ID NO 106
<211> LENGTH: 38
<212> TYPE: DNA
<213> ORGANISM: Artificial Sequence
<220> FEATURE:
<223> OTHER INFORMATION: reporter

<400> SEQUENCE: 106
aaaacctatc atcataggtc atcatgctta tggggatc                    38

<210> SEQ ID NO 107
<211> LENGTH: 38
<212> TYPE: DNA
<213> ORGANISM: Artificial Sequence
<220> FEATURE:
<223> OTHER INFORMATION: reporter

<400> SEQUENCE: 107
gatccccata agcatgatga cctatgatga taggtttt                    38

<210> SEQ ID NO 108
<211> LENGTH: 21
<212> TYPE: RNA
<213> ORGANISM: Artificial Sequence
<220> FEATURE:
<223> OTHER INFORMATION: siRNA

<400> SEQUENCE: 108
auguagcaaa ucagaagccc u                                      21

<210> SEQ ID NO 109
<211> LENGTH: 21
<212> TYPE: RNA
<213> ORGANISM: Artificial Sequence
<220> FEATURE:
<223> OTHER INFORMATION: siRNA
```

-continued

```
<400> SEQUENCE: 109
ggcuucugau uugcuacauu u                                              21

<210> SEQ ID NO 110
<211> LENGTH: 21
<212> TYPE: RNA
<213> ORGANISM: Artificial Sequence
<220> FEATURE:
<223> OTHER INFORMATION: siRNA

<400> SEQUENCE: 110
guguagcaca ucacaagcac u                                              21

<210> SEQ ID NO 111
<211> LENGTH: 21
<212> TYPE: RNA
<213> ORGANISM: Artificial Sequence
<220> FEATURE:
<223> OTHER INFORMATION: siRNA

<400> SEQUENCE: 111
ugcuugugau gugcuacacu u                                              21

<210> SEQ ID NO 112
<211> LENGTH: 21
<212> TYPE: RNA
<213> ORGANISM: Artificial Sequence
<220> FEATURE:
<223> OTHER INFORMATION: siRNA

<400> SEQUENCE: 112
gaccucuucg acaucgagga u                                              21

<210> SEQ ID NO 113
<211> LENGTH: 21
<212> TYPE: RNA
<213> ORGANISM: Artificial Sequence
<220> FEATURE:
<223> OTHER INFORMATION: siRNA

<400> SEQUENCE: 113
ccucgauguc gaagaggucc u                                              21

<210> SEQ ID NO 114
<211> LENGTH: 21
<212> TYPE: RNA
<213> ORGANISM: Artificial Sequence
<220> FEATURE:
<223> OTHER INFORMATION: siRNA

<400> SEQUENCE: 114
gaccucuugg acaacgagaa u                                              21

<210> SEQ ID NO 115
<211> LENGTH: 21
<212> TYPE: RNA
<213> ORGANISM: Artificial Sequence
<220> FEATURE:
<223> OTHER INFORMATION: siRNA

<400> SEQUENCE: 115
ucucguuguc caagaggucc u                                              21

<210> SEQ ID NO 116
<211> LENGTH: 21
```

<212> TYPE: RNA
<213> ORGANISM: Artificial Sequence
<220> FEATURE:
<223> OTHER INFORMATION: siRNA

<400> SEQUENCE: 116
gaaagggacg aacuggugua a                                                          21

<210> SEQ ID NO 117
<211> LENGTH: 21
<212> TYPE: RNA
<213> ORGANISM: Artificial Sequence
<220> FEATURE:
<223> OTHER INFORMATION: siRNA

<400> SEQUENCE: 117
acaccaguuc gucccuuucc a                                                          21

<210> SEQ ID NO 118
<211> LENGTH: 21
<212> TYPE: RNA
<213> ORGANISM: Artificial Sequence
<220> FEATURE:
<223> OTHER INFORMATION: siRNA

<400> SEQUENCE: 118
gaaagggagg aacaggugaa a                                                          21

<210> SEQ ID NO 119
<211> LENGTH: 21
<212> TYPE: RNA
<213> ORGANISM: Artificial Sequence
<220> FEATURE:
<223> OTHER INFORMATION: siRNA

<400> SEQUENCE: 119
ucaccuguuc cucccuuucc a                                                          21

<210> SEQ ID NO 120
<211> LENGTH: 21
<212> TYPE: RNA
<213> ORGANISM: Artificial Sequence
<220> FEATURE:
<223> OTHER INFORMATION: siRNA

<400> SEQUENCE: 120
aaaccaagcg agaaguaccu a                                                          21

<210> SEQ ID NO 121
<211> LENGTH: 21
<212> TYPE: RNA
<213> ORGANISM: Artificial Sequence
<220> FEATURE:
<223> OTHER INFORMATION: siRNA

<400> SEQUENCE: 121
gguacuucuc gcuugguuug a                                                          21

<210> SEQ ID NO 122
<211> LENGTH: 21
<212> TYPE: RNA
<213> ORGANISM: Artificial Sequence
<220> FEATURE:
<223> OTHER INFORMATION: siRNA

<400> SEQUENCE: 122

-continued

```
gaaccaagug agauguacau a                                          21

<210> SEQ ID NO 123
<211> LENGTH: 21
<212> TYPE: RNA
<213> ORGANISM: Artificial Sequence
<220> FEATURE:
<223> OTHER INFORMATION: siRNA

<400> SEQUENCE: 123
uguacaucuc acuugguucg a                                          21

<210> SEQ ID NO 124
<211> LENGTH: 21
<212> TYPE: RNA
<213> ORGANISM: Artificial Sequence
<220> FEATURE:
<223> OTHER INFORMATION: siRNA

<400> SEQUENCE: 124
gugcaaugcc uguggccucu a                                          21

<210> SEQ ID NO 125
<211> LENGTH: 21
<212> TYPE: RNA
<213> ORGANISM: Artificial Sequence
<220> FEATURE:
<223> OTHER INFORMATION: siRNA

<400> SEQUENCE: 125
gaggccacag gcauugcaca g                                          21

<210> SEQ ID NO 126
<211> LENGTH: 21
<212> TYPE: RNA
<213> ORGANISM: Artificial Sequence
<220> FEATURE:
<223> OTHER INFORMATION: siRNA

<400> SEQUENCE: 126
gugcaauguc ugucgccuau a                                          21

<210> SEQ ID NO 127
<211> LENGTH: 21
<212> TYPE: RNA
<213> ORGANISM: Artificial Sequence
<220> FEATURE:
<223> OTHER INFORMATION: siRNA

<400> SEQUENCE: 127
uaggcgacag acauugcaca g                                          21

<210> SEQ ID NO 128
<211> LENGTH: 21
<212> TYPE: RNA
<213> ORGANISM: Artificial Sequence
<220> FEATURE:
<223> OTHER INFORMATION: siRNA

<400> SEQUENCE: 128
gaagcgacug auccccauca a                                          21

<210> SEQ ID NO 129
<211> LENGTH: 21
<212> TYPE: RNA
<213> ORGANISM: Artificial Sequence
```

-continued

```
<220> FEATURE:
<223> OTHER INFORMATION: siRNA

<400> SEQUENCE: 129
gauggggauc agucgcuucu g                                         21

<210> SEQ ID NO 130
<211> LENGTH: 21
<212> TYPE: RNA
<213> ORGANISM: Artificial Sequence
<220> FEATURE:
<223> OTHER INFORMATION: siRNA

<400> SEQUENCE: 130
gaagcgaccg aucgccauaa a                                         21

<210> SEQ ID NO 131
<211> LENGTH: 21
<212> TYPE: RNA
<213> ORGANISM: Artificial Sequence
<220> FEATURE:
<223> OTHER INFORMATION: siRNA

<400> SEQUENCE: 131
uauggcgauc ggucgcuucu g                                         21

<210> SEQ ID NO 132
<211> LENGTH: 21
<212> TYPE: RNA
<213> ORGANISM: Artificial Sequence
<220> FEATURE:
<223> OTHER INFORMATION: siRNA

<400> SEQUENCE: 132 aggggggccaa aggucagaga g                                        21

<210> SEQ ID NO 133
<211> LENGTH: 21
<212> TYPE: RNA
<213> ORGANISM: Artificial Sequence
<220> FEATURE:
<223> OTHER INFORMATION: siRNA

<400> SEQUENCE: 133
cucugaccuu uggcccccua c                                         21

<210> SEQ ID NO 134
<211> LENGTH: 21
<212> TYPE: RNA
<213> ORGANISM: Artificial Sequence
<220> FEATURE:
<223> OTHER INFORMATION: siRNA

<400> SEQUENCE: 134 gggggggccua aggacagaaa g                                        21

<210> SEQ ID NO 135
<211> LENGTH: 21
<212> TYPE: RNA
<213> ORGANISM: Artificial Sequence
<220> FEATURE:
<223> OTHER INFORMATION: siRNA

<400> SEQUENCE: 135
uucuguccuu aggcccccca c                                         21
```

<210> SEQ ID NO 136
<211> LENGTH: 21
<212> TYPE: RNA
<213> ORGANISM: Artificial Sequence
<220> FEATURE:
<223> OTHER INFORMATION: siRNA

<400> SEQUENCE: 136
cauaggucgu caugcuuaug g                                                                     21

<210> SEQ ID NO 137
<211> LENGTH: 21
<212> TYPE: RNA
<213> ORGANISM: Artificial Sequence
<220> FEATURE:
<223> OTHER INFORMATION: siRNA

<400> SEQUENCE: 137
auaagcauga cgaccuauga u                                                                     21

<210> SEQ ID NO 138
<211> LENGTH: 21
<212> TYPE: RNA
<213> ORGANISM: Artificial Sequence
<220> FEATURE:
<223> OTHER INFORMATION: siRNA

<400> SEQUENCE: 138
cauaggucau caugguuaug g                                                                     21

<210> SEQ ID NO 139
<211> LENGTH: 21
<212> TYPE: RNA
<213> ORGANISM: Artificial Sequence
<220> FEATURE:
<223> OTHER INFORMATION: siRNA

<400> SEQUENCE: 139
auaaccauga ugaccuauga u                                                                     21

<210> SEQ ID NO 140
<211> LENGTH: 21
<212> TYPE: RNA
<213> ORGANISM: Artificial Sequence
<220> FEATURE:
<223> OTHER INFORMATION: siRNA

<400> SEQUENCE: 140
gccacaacgu cuauaucaug g                                                                     21

<210> SEQ ID NO 141
<211> LENGTH: 21
<212> TYPE: RNA
<213> ORGANISM: Artificial Sequence
<220> FEATURE:
<223> OTHER INFORMATION: siRNA

<400> SEQUENCE: 141
augauauaga cguuguggcu g                                                                     21

<210> SEQ ID NO 142
<211> LENGTH: 21
<212> TYPE: RNA
<213> ORGANISM: Artificial Sequence
<220> FEATURE:
<223> OTHER INFORMATION: siRNA

<400> SEQUENCE: 142
cagcuaauuc agaaucauuu u                                          21

<210> SEQ ID NO 143
<211> LENGTH: 21
<212> TYPE: RNA
<213> ORGANISM: Artificial Sequence
<220> FEATURE:
<223> OTHER INFORMATION: siRNA

<400> SEQUENCE: 143
aaugauucug aauuagcugu a                                          21

<210> SEQ ID NO 144
<211> LENGTH: 21
<212> TYPE: RNA
<213> ORGANISM: Artificial Sequence
<220> FEATURE:
<223> OTHER INFORMATION: siRNA

<400> SEQUENCE: 144
uggagcuggu ggcguaggca a                                          21

<210> SEQ ID NO 145
<211> LENGTH: 21
<212> TYPE: RNA
<213> ORGANISM: Artificial Sequence
<220> FEATURE:
<223> OTHER INFORMATION: siRNA

<400> SEQUENCE: 145
gccuacgcca ccagcuccaa c                                          21

<210> SEQ ID NO 146
<211> LENGTH: 19
<212> TYPE: RNA
<213> ORGANISM: Artificial Sequence
<220> FEATURE:
<223> OTHER INFORMATION: siRNA

<400> SEQUENCE: 146
cccaacacca ccugcucca                                             19

<210> SEQ ID NO 147
<211> LENGTH: 19
<212> TYPE: RNA
<213> ORGANISM: Artificial Sequence
<220> FEATURE:
<223> OTHER INFORMATION: siRNA

<400> SEQUENCE: 147
guacucuucu uguccagcu                                             19

<210> SEQ ID NO 148
<211> LENGTH: 19
<212> TYPE: RNA
<213> ORGANISM: Artificial Sequence
<220> FEATURE:
<223> OTHER INFORMATION: siRNA

<400> SEQUENCE: 148
ggcuucugau uugcuacau                                             19

<210> SEQ ID NO 149

```
<211> LENGTH: 19
<212> TYPE: RNA
<213> ORGANISM: Artificial Sequence
<220> FEATURE:
<223> OTHER INFORMATION: siRNA

<400> SEQUENCE: 149
ccucgauguc gaagagguc                                                     19

<210> SEQ ID NO 150
<211> LENGTH: 19
<212> TYPE: RNA
<213> ORGANISM: Artificial Sequence
<220> FEATURE:
<223> OTHER INFORMATION: siRNA

<400> SEQUENCE: 150
acaccaguuc gucccuuuc                                                     19

<210> SEQ ID NO 151
<211> LENGTH: 19
<212> TYPE: RNA
<213> ORGANISM: Artificial Sequence
<220> FEATURE:
<223> OTHER INFORMATION: siRNA

<400> SEQUENCE: 151
gguacuucuc gcuugguuu                                                     19

<210> SEQ ID NO 152
<211> LENGTH: 19
<212> TYPE: RNA
<213> ORGANISM: Artificial Sequence
<220> FEATURE:
<223> OTHER INFORMATION: siRNA

<400> SEQUENCE: 152
gaggccacag gcauugcac                                                     19

<210> SEQ ID NO 153
<211> LENGTH: 19
<212> TYPE: RNA
<213> ORGANISM: Artificial Sequence
<220> FEATURE:
<223> OTHER INFORMATION: siRNA

<400> SEQUENCE: 153
gauggggauc agucgcuuc                                                     19

<210> SEQ ID NO 154
<211> LENGTH: 19
<212> TYPE: RNA
<213> ORGANISM: Artificial Sequence
<220> FEATURE:
<223> OTHER INFORMATION: siRNA

<400> SEQUENCE: 154
cucugaccuu uggcccccu                                                     19
```

-continued

```
<210> SEQ ID NO 155
<211> LENGTH: 19
<212> TYPE: RNA
<213> ORGANISM: Artificial Sequence
<220> FEATURE:
<223> OTHER INFORMATION: siRNA

<400> SEQUENCE: 155
auaagcauga cgaccuaug                                              19
```